US005847211A

United States Patent [19]

Fischer et al.

[11] Patent Number: 5,847,211

[45] Date of Patent: Dec. 8, 1998

[54] SUBSTITUTED 1H-3-ARYL-PYRROLIDINE-2, 4-DIONE DERIVATIVES

[75] Inventors: Reiner Fischer, Monheim; Thomas Bretschneider, Lohmar; Bernd-Wieland Krüger, Bergisch Gladbach; Michael Ruther, Monheim; Christoph Erdelen, Leichlingen; Ulrike Wachendorff-Neumann, Monheim; Hans-Joachim Santel; Markus Dollinger, both of Leverkusen, all of Germany

[73] Assignee: Bayer Aktiengesellschaft, Leverkusen, Germany

[21] Appl. No.: 759,352

[22] Filed: Dec. 3, 1996

Related U.S. Application Data

[62] Division of Ser. No. 383,801, Feb. 3, 1995, Pat. No. 5,622, 917.

[30] Foreign Application Priority Data

Feb. 9, 1994 [DE] Germany .......................... 44 04 001.6
Sep. 6, 1994 [DE] Germany .......................... 44 31 730.1

[51] Int. Cl.$^6$ .................................................. C07C 233/00

[52] U.S. Cl. ............................................................. 564/123

[58] Field of Search .............................................. 564/123

[56] References Cited

FOREIGN PATENT DOCUMENTS

| | | |
|---|---|---|
| 0 613 885 | 9/1974 | European Pat. Off. . |
| 0 377 893 | 7/1990 | European Pat. Off. . |
| 0 456 063 | 11/1991 | European Pat. Off. . |
| 456063 | 11/1991 | European Pat. Off. . |
| 0 521 334 | 1/1993 | European Pat. Off. . |
| 0 595 130 | 5/1994 | European Pat. Off. . |
| 0 596 298 | 5/1994 | European Pat. Off. . |
| 0 613 884 | 9/1994 | European Pat. Off. . |
| 9 401 401 | 1/1994 | WIPO . |

OTHER PUBLICATIONS

Takahashi et al., "Agricultural and Horticultural Herbicides . . . ", Chem. Abs., vol. 82 (1975), p. 175, Abstract #27233.

*Primary Examiner*—Richard L. Raymond
*Assistant Examiner*—Tamthom T. Ngo
*Attorney, Agent, or Firm*—Sprung Kramer Schaefer & Briscoe

[57] ABSTRACT

The invention relates to new 1H-3-aryl-pyrrolidine-2,4-dione derivatives of the formula (I)

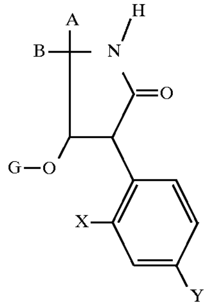

(I)

in which

A, B, X, Y and G have the meanings given in the description, to a plurality of processes for their preparation, and to their use as pesticides.

7 Claims, No Drawings

SUBSTITUTED 1H-3-ARYL-PYRROLIDINE-2,4-DIONE DERIVATIVES

This application is a divisional application of U.S. application Ser. No. 08/383,801 filed on Feb. 3, 1995, now U.S. Pat. No. 5,622,917.

The invention relates to new 1H-3-aryl-pyrrolidine-2,4-dione derivatives, to a plurality of processes for their preparation, and to their use as pesticides, in particular as insecticides, acaricides and herbicides.

Pharmaceutical properties of 3-acyl-pyrrolidine-2,4-diones have previously been described (S. Suzuki et al. Chem. Pharm. Bull. 15 1120 (1967)). Furthermore, N-phenylpyrrolidine-2,4-diones were synthesized by R. Schmierer and H. Mildenberger (Liebigs Ann. Chem. 1985 1095). A biological activity of these compounds was not described.

EP-A-0 262 399 and GB-2 266 888-A disclose compounds of a similar structure (3-aryl-pyrrolidine-2,4-diones), but no herbicidal, insecticidal or acaricidal activity has been disclosed. Known substances which have a herbicidal, insecticidal or acaricidal activity are unsubstituted, bicyclic 3-aryl-pyrrolidine-2,4-dione derivatives (EP-A-355 599 and EP-415 211) and substituted monocyclic 3-aryl-pyrrolidine-2,4-dione derivatives (EP-A-377 893 and EP-442 077).

Polycyclic 3-arylpyrrolidine-2,4-dione derivatives (EP-422 073) and 1H-3-arylpyrrolidine-dione derivatives (EP-456 063 and EP-521 334) are furthermore known.

New substituted 1H-3-aryl-pyrrolidine-2,4-dione derivatives of the formula (I) have now been found

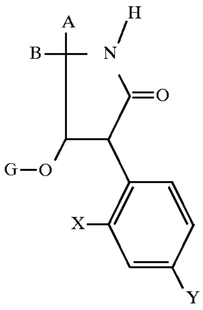

(I)

in which

A represents hydrogen, or alkyl, alkenyl, alkoxyalkyl or alkylthioalkyl, each of which is optionally substituted by halogen, or cycloalkyl which is optionally interrupted by at least one hetero atom and optionally substituted, or aryl, arylalkyl or hetaryl, each of which is optionally substituted by halogen, alkyl, halogenoalkyl, alkoxy or nitro, B represents hydrogen, alkyl or alkoxyalkyl, or A and B together with the carbon atom to which they are bonded represent a saturated or unsaturated, unsubstituted or substituted cycle which is optionally interrupted by at least one hetero atom, X represents halogen or alkyl, Y represents halogen or alkyl, G represents hydrogen (a) or one of the groups

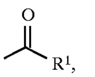

(b)

-continued

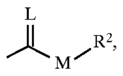

(c)

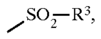

(d)

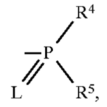

(e)

E (f)

or

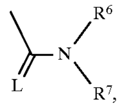

(g)

E represents a metal ion equivalent or an ammonium ion,

L and M represent in each case oxygen or sulphur, $R^1$ represents alkyl, alkenyl, alkoxyalkyl, alkylthioalkyl or polyalkoxyalkyl, each of which is optionally substituted by halogen, or cycloalkyl which is optionally substituted by halogen or alkyl and can be interrupted by at least one hetero atom, or in each case optionally substituted phenyl, phenylalkyl, hetaryl, phenoxyalkyl or hetaryloxyalkyl, $R^2$ represents alkyl, alkenyl, alkoxyalkyl or polyalkoxyalkyl, each of which is optionally substituted by halogen, or in each case optionally substituted cycloalkyl, phenyl or benzyl, $R^3$, $R^4$ and $R^5$ independently of one another represent alkyl, alkoxy, alkylamino, dialkylamino, alkylthio, alkenylthio or cycloalkylthio, each of which is optionally substituted by halogen, or in each case optionally substituted phenyl, phenoxy or phenylthio, $R^6$ and $R^7$ independently of one another represent hydrogen, or alkyl, cycloalkyl, alkenyl, alkoxy or alkoxy-alkyl, each of which is optionally substituted by halogen, or in each case optionally substituted phenyl or benzyl, or together with the N atom to which they are bonded a cycle which is optionally interrupted by oxygen or sulphur, with the proviso that X and Y do not simultaneously represent alkyl and not simultaneously halogen.

Taking into account the various meanings (a), (b), (c), (d), (e), (f) and (g) of group G, the following main structures (Ia) to (Ig) result:

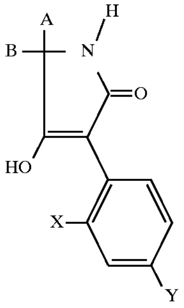

(Ia)

-continued (Ib)

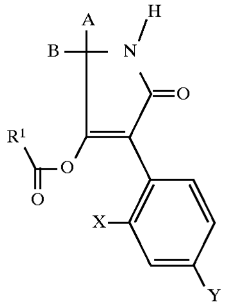

(Ic)

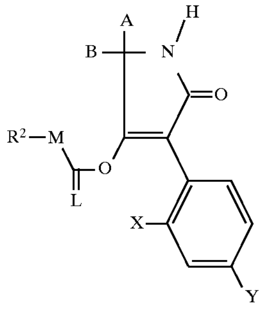

(Id)

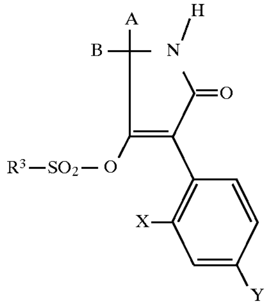

(Ie)

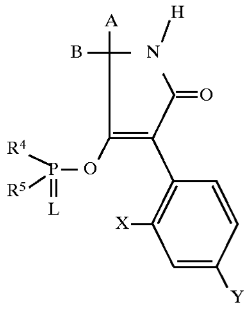

(If)

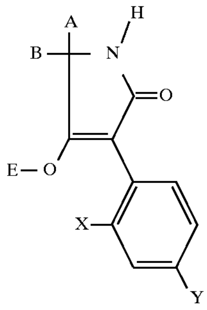

-continued (Ig)

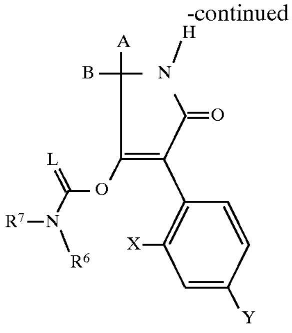

in which

A, B, E, L, M, X, Y, $R^1$, $R^2$, $R^3$, $R^4$, $R^5$, $R^6$ and $R^7$ have the abovementioned meanings.

Due to one or more chiral centres, the compounds of the formula (Ia)–(Ig) are generally obtained in the form of a mixture of stereoisomers which, if appropriate, can be separated in the customary manner. They can be used in the form of their mixtures of diastereomers and also in the form of pure diastereomers or enantiomers. For the sake of simplicity, the following text will always mention compounds of the formulae (Ia) to (Ig), even though this is to be understood as meaning the pure compounds as well as the mixtures comprising various amounts of isomeric, enantiomeric and stereomeric compounds.

Furthermore, it has been found that the new substituted 1H-3-aryl-pyrrolidine-2,4-dione derivatives of the formula (I) are obtained by one of the processes described hereinbelow.

(A) 1H-3-Aryl-pyrrolidine-2,4-diones or their enols of the formula (Ia)

(Ia)

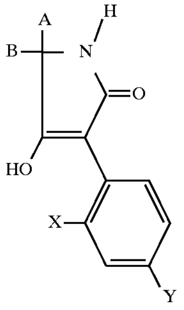

in which

A, B, X and Y have the abovementioned meanings are obtained when

N-acylamino acid esters of the formula (II)

(II)

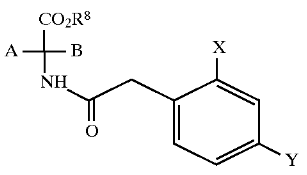

in which

A, B, X and Y have the abovementioned meanings and $R^8$ represents alkyl, in particular $C_1$–$C_{10}$-alkyl, are subjected to an intramolecular condensation reaction in the presence of a diluent and in the presence of a base; or (B) Compounds of the formula (Ib)

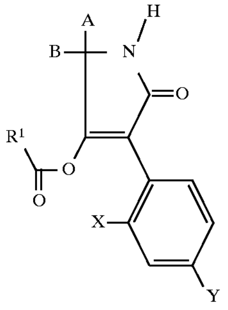

(Ib)

in which

A, B, X, Y and $R^1$ have the abovementioned meanings are obtained when compounds of the formula (Ia)

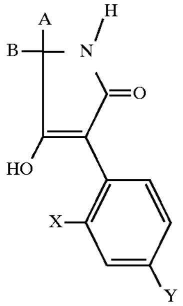

(Ia)

in which

A, B, X and Y have the abovementioned meanings

α) are reacted with acid halides of the formula (III)

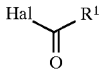

(III)

in which $R^1$ has the abovementioned meaning and

Hal represents halogen, in particular chlorine or bromine, if appropriate in the presence of a diluent and if appropriate in the presence of an acid-binding agent, or β) are reacted with carboxylic anhydrides of the formula (IV)

$$R^1—CO—O—CO—R^1 \qquad (IV)$$

in which $R^1$ has the abovementioned meaning, if appropriate in the presence of a diluent and if appropriate in the presence of an acid-binding agent; or (C) Compounds of the formula (Ic-a)

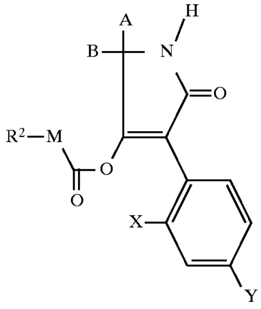

(Ic-a)

in which

A, B, X, Y and $R^2$ have the abovementioned meanings and

M represents oxygen or sulphur are obtained when compounds of the formula (Ia)

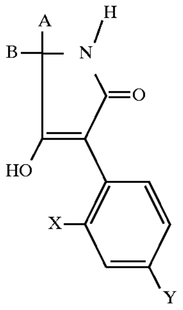

(Ia)

in which

A, B, X and Y have the abovementioned meanings, are reacted with chloroformic esters or chloroformic thioesters of the formula (V)

$$R^2—M—CO—Cl \qquad (V)$$

in which $R^2$ and M have the abovementioned meanings, if appropriate in the presence of a diluent and if appropriate in the presence of an acid-binding agent; or (D) compounds of the formula (Ic-b)

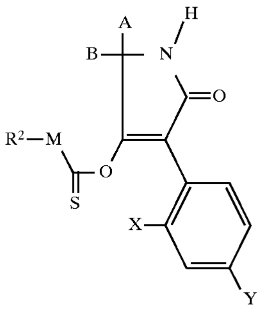

(Ic-b)

in which

A, B, $R^2$, X and Y have the abovementioned meanings and

M represents oxygen or sulphur are obtained when compounds of the formula (Ia)

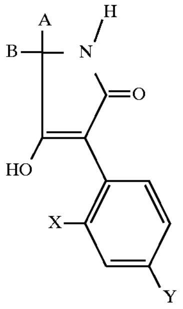

(Ia)

in which

A, B, X and Y have the abovementioned meanings

α) are reacted with chloromonothioformic esters or chlorodithioformic esters of the formula (VI)

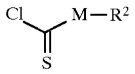

(VI)

in which

M and $R^2$ have the abovementioned meanings, if appropriate in the presence of a diluent and if appropriate in the presence of an acid-binding agent, or β) are reacted with carbon disulphide and subsequently with alkyl halides of the formula (VII)

$R^2$—Hal (VII)

in which $R^2$ has the abovementioned meaning and

Hal represents chlorine, bromine or iodine; or (E) Compounds of the formula (Id)

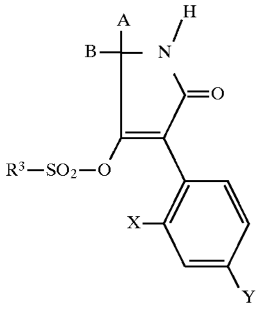

(Id)

in which

A, B, X, Y and $R^3$ have the abovementioned meanings are obtained when compounds of the formula (Ia)

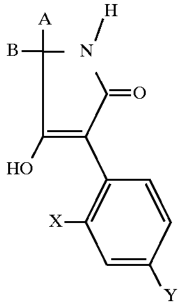

(Ia)

in which

A, B, X and Y have the abovementioned meanings are reacted with sulphonyl chlorides of the formula (VIII)

$R^3$—$SO_2$—Cl (VIII)

in which $R^3$ has the abovementioned meaning, if appropriate in the presence of a diluent and if appropriate in the presence of an acid-binding agent; or (F) 3-aryl-pyrrolidine-2,4-diones of the formula (Ie)

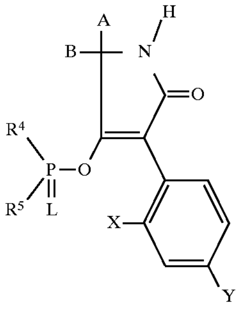

(Ie)

in which

A, B, L, X, Y, $R^4$ and $R^5$ have the abovementioned meanings are obtained when 1H-3-arylpyrrolidine-2,4-diones of the formula (Ia) or their enols

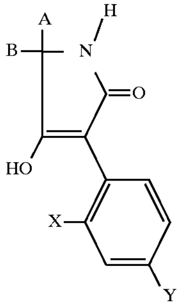

(Ia)

in which

A, B, X and Y have the abovementioned meanings are reacted with phosphorus compounds of the formula (IX)

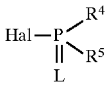

(IX)

in which

L, $R^4$ and $R^5$ have the abovementioned meanings and

Hal represents halogen, in particular chlorine or bromine, if appropriate in the presence of a diluent and if appropriate in the presence of an acid-binding agent; or (G) Compounds of the formula (If)

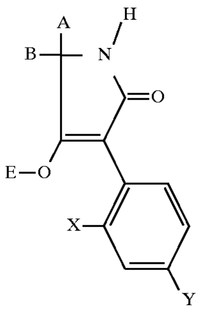

(I-f)

in which

A, B, X and Y have the abovementioned meanings and

E represents a metal ion equivalent or an ammonium ion are obtained when compounds of the formula (Ia)

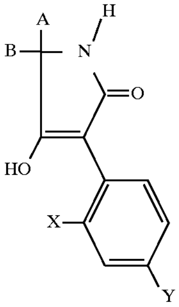

(Ia)

in which

A, B, X and Y have the abovementioned meanings are reacted with metal hydroxides, metal alkoxides or amines of the formulae (X) and (XI)

$Me(OR^{10})_t$ (X)

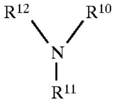

(XI)

in which

Me represents a mono- or divalent metal such as, for example, lithium, potassium, sodium, calcium or magnesium, t represents the number 1 or 2 and $R^{10}$, $R^{11}$ and $R^{12}$ independently of one another represent hydrogen and/or alkyl, if appropriate in the presence of a diluent.

(H) Furthermore, it has been found that compounds of the formula (I-g)

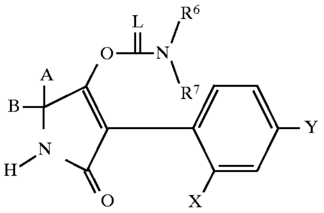

(Ig)

in which

A, B, L, X, Y, $R^6$ and $R^7$ have the abovementioned meanings are obtained when compounds of the formula (Ia)

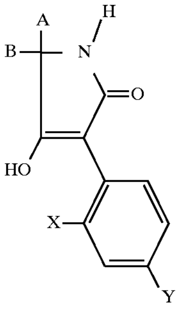

(Ia)

in which

A, B, X and Y have the abovementioned meanings are reacted

α) with isocyanates or isothiocyanates of the formula (XII)

$R^6—N=C=L$ (XII)

in which

L and $R^6$ have the abovementioned meanings, if appropriate in the presence of a diluent and if appropriate in the presence of a catalyst, or β) with carbamoyl chlorides or thiocarbamoyl chlorides of the formula (XIII)

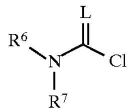

(XIII)

in which

L, $R^6$ and $R^7$ have the abovementioned meanings, if appropriate in the presence of a diluent and if appropriate in the presence of an acid-binding agent.

Furthermore, it has been found that the new 1H-3-arylpyrrolidine-2,4-dione derivatives of the formula (I) are distinguished by outstanding insecticidal, acaricidal and herbicidal activities.

The following applies to the general formulae of the present application:

A preferably represents hydrogen, or $C_1$–$C_{12}$-alkyl, $C_3$–$C_8$-alkenyl, $C_1$–$C_{10}$-alkoxy-$C_1$–$C_8$-alkyl, $C_1$–$C_8$-polyalkoxy-$C_1$–$C_8$-alkyl or $C_1$–$C_{10}$-alkylthio-$C_1$–$C_6$-alkyl, each of which is optionally substituted by halogen, or cycloalkyl having 3 to 8 ring atoms which is optionally substituted by halogen, $C_1$–$C_4$-alkyl or $C_1$–$C_4$-alkoxy and can be interrupted by oxygen and/or sulphur, or represents aryl, 5- to 6-membered hetaryl or aryl-$C_1$–$C_6$-alkyl, each of which is optionally substituted by halogen, $C_1$–$C_6$-alkyl, $C_1$–$C_6$-halogenoalkyl, $C_1$–$C_6$-alkoxy and/or nitro, B preferably represents hydrogen, $C_1$–$C_{12}$-alkyl or $C_1$–$C_8$-alkoxyalkyl, or A, B and the carbon atom to which they are bonded preferably represent a saturated or unsaturated $C_3$–$C_{10}$-spirocycle which is optionally interrupted by oxygen or sulphur and optionally monosubstituted or polysubstituted by $C_1$–$C_{10}$-alkyl, $C_3$–$C_{10}$-cycloalkyl, $C_1$–$C_6$-halogenoalkyl, $C_1$–$C_{10}$-alkoxy, $C_1$–$C_{10}$-alkylthio, halogen or phenyl, or A, B and the carbon atom to which they are bonded preferably represent a $C_3$–$C_6$-spirocycle which is substituted by an alkylenediyl group which is optionally interrupted by one or two oxygen and/or sulphur atoms, or which is substituted by an alkylenedioxy or by an alkylenedithio group, this alkylenediyl, alkylenedioxy or alkylenedithio group together with the carbon atom to which it is bonded forming a further five- to eight-membered spirocycle, or A, B and the carbon atom to which they are bonded preferably represent a $C_3$–$C_8$-spirocycle in which two substituents together represent a saturated or unsaturated 3- to 8-membered cycle which is optionally substituted by $C_1$–$C_6$-alkyl, $C_1$–$C_6$-alkoxy or halogen and which can be interrupted by oxygen or sulphur.

A particularly preferably represents hydrogen, or $C_1$–$C_{10}$-alkyl, $C_3$–$C_6$-alkenyl, $C_1$–$C_8$-alkoxy-$C_1$–$C_6$-alkyl, $C_1$–$C_6$-polyalkoxy-$C_1$–$C_6$-alkyl or $C_1$–$C_8$-alkylthio-$C_1$–$C_6$-alkyl, each of which is optionally substituted by fluorine and/or chlorine, or cycloalkyl having 3 to 7 ring atoms which is optionally substituted by fluorine, chlorine, $C_1$–$C_3$-alkyl or $C_1$–$C_3$-alkoxy and which can be interrupted by 1 or 2 oxygen and/or sulphur atoms, or represents phenyl, furanyl, pyridyl, imidazolyl, triazolyl, pyrazolyl, indolyl, thiazolyl, thienyl or phenyl-$C_1$–$C_4$-alkyl, each of which is optionally substituted by fluorine, chlorine, bromine, $C_1$–$C_4$-alkyl, $C_1$–$C_4$-halogenoalkyl, $C_1$–$C_4$-alkoxy and/or nitro.

B particularly preferably represents hydrogen, $C_1$–$C_{10}$-alkyl or $C_1$–$C_6$-alkoxyalkyl, or A, B and the carbon atom to which they are bonded particularly preferably represent a saturated or unsaturated $C_3$–$C_9$-spirocycle which is optionally interrupted by oxygen or sulphur and optionally monosubstituted or polysubstituted by $C_1$–$C_6$-alkyl, $C_3$–$C_8$-cycloalkyl, $C_1$–$C_3$-haloalkyl, $C_1$–$C_6$-alkoxy, $C_1$–$C_6$-alkylthio, fluorine, chlorine or phenyl, or A, B and the carbon atom to which they are bonded particularly preferably represent a $C_3$–$C_6$-spirocycle which is substituted by an alkylenediyl group which is optionally interrupted by one or two oxygen or sulphur atoms or which is substituted by an alkylenedioxy or by an alkylenedithio group, this alkylenediyl, alkylenedioxy or alkylenedithio group together with the carbon atom to which it is bonded forming a further five- to seven-membered spirocycle, or A, B and the carbon atom to which they are bonded particularly preferably represent a $C_3$–$C_6$-spirocycle in which two substituents together represent a saturated or unsaturated 5- to 8-membered cycle which is optionally substituted by $C_3$–$C_3$-alkyl, $C_1$–$C_3$-alkoxy, fluorine, chlorine or bromine and which can be interrupted by oxygen or sulphur.

A very particularly preferably represents hydrogen, or $C_1$–$C_8$-alkyl, $C_3$–$C_4$-alkenyl, $C_1$–$C_6$-alkoxy-$C_1$–$C_4$-alkyl, $C_1$–$C_4$-polyalkoxy-$C_1$–$C_4$-alkyl or $C_1$–$C_6$-alkylthio-$C_1$–$C_4$-alkyl, each of which is optionally substituted by fluorine and/or chlorine, or cycloalkyl having 3 to 6 ring atoms which is optionally substituted by fluorine, chlorine, methyl, ethyl, methoxy or ethoxy and which can be interrupted by 1 or 2 oxygen and/or sulphur atoms, or represents phenyl, furanyl, pyridyl, imidazolyl, pyrazolyl, triazolyl, indolyl, thiazolyl, thienyl or benzyl, each of which is optionally substituted by fluorine, chlorine, bromine, methyl, ethyl, propyl, iso-propyl, methoxy, ethoxy, trifluoromethyl and/or nitro.

B very particularly preferably represents hydrogen, $C_1$–$C_8$-alkyl or $C_1$–$C_4$-alkoxyalkyl, or A, B and the carbon atom to which they are bonded very particularly preferably represent a saturated or unsaturated $C_3$–$C_8$-spirocycle which is optionally interrupted by oxygen or sulphur and optionally monosubstituted or polysubstituted by methyl, ethyl, propyl, isopropyl, butyl, iso-butyl, sec-butyl, tert-butyl, cyclohexyl, trifluoromethyl, methoxy, ethoxy, propoxy, iso-propoxy, butoxy, iso-butoxy, sec-butoxy, tert-butoxy, methylthio, ethylthio, fluorine, chlorine or phenyl, or A, B and the carbon atom to which they are bonded very particularly preferably represent a $C_3$–$C_6$-spirocycle which is substituted by an alkylenediyl group which is optionally interrupted by an oxygen or sulphur atom, or which is substituted by an alkylenedioxy group, this alkylenediyl or alkylenedioxy group together with the carbon atom to which it is bonded forming a further five- to seven-membered spirocycle, or A, B and the carbon atom to which they are bonded very particularly preferably represent a $C_3$–$C_6$-spirocycle in which two substituents together represent a saturated or unsaturated five- or six-membered cycle which can be interrupted by oxygen or sulphur.

X preferably represents halogen or $C_1$–$C_6$-alkyl.

X particularly preferably represents fluorine, chlorine, bromine or $C_1$–$C_4$-alkyl.

X very particularly preferably represents chlorine, bromine, methyl, ethyl, propyl or iso-propyl.

Y preferably represents halogen or $C_1$–$C_6$-alkyl.

Y particularly preferably represents fluorine, chlorine, bromine or $C_1$–$C_4$-alkyl.

Y very particularly preferably represents chlorine, bromine, methyl, ethyl, propyl or iso-propyl.

In these formulae, X and Y do not simultaneously represent alkyl and not simultaneously halogen.

G preferably represents hydrogen (a) or one of the groups

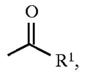 (b)

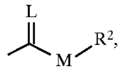 (c)

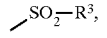 (d)

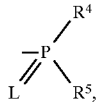 (e)

E (f)

or

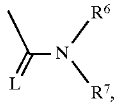 (g)

in which

E represents a metal ion equivalent or an ammonium ion and

L and M in each case represent oxygen or sulphur.

$R^1$ preferably represents $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl or $C_1$–$C_8$-polyalkoxy-$C_1$–$C_8$-alkyl, each of which is optionally substituted by halogen, or cycloalkyl having 3 to 8 ring atoms which is optionally substituted by halogen or $C_1$–$C_6$-alkyl and which can be interrupted by at least one oxygen and/or sulphur atom, phenyl which is optionally substituted by halogen, nitro, $C_1$–$C_6$-alkyl, $C_1$–$C_6$-alkoxy, $C_1$–$C_6$-halogenoalkyl, $C_1$–$C_6$-halogenoalkoxy, $C_1$–$C_6$-alkylthio or $C_1$–$C_6$alkylsulphonyl, phenyl-$C_1$–$C_6$-alkyl which is optionally substituted by halogen, $C_1$–$C_6$-alkyl, $C_1$–$C_6$-alkoxy, $C_1$–$C_6$-halogenoalkyl or $C_1$–$C_6$-halogenoalkoxy, 5- or 6-membered hetaryl which is optionally substituted by halogen and/or $C_1$–$C_6$-alkyl, phenoxy-$C_1$–$C_6$-alkyl which is optionally substituted by halogen and/or $C_1$–$C_6$-alkyl, or 5- or 6-membered hetaryloxy-$C_1$–$C_6$-alkyl which is optionally substituted by halogen, amino and/or $C_1$–$C_6$-alkyl.

$R^2$ preferably represents $C_1$–$C_{20}$-alkyl, $C_3$–$C_{20}$-alkenyl, $C_1$–$C_8$-alkoxy-$C_1$–$C_8$-alkyl or $C_1$–$C_8$-polyalkoxy-$C_1$–$C_8$-alkyl, each of which is optionally substituted by halogen, $C_3$–$C_8$-cycloalkyl which is optionally substituted by halogen, $C_1$–$C_4$-alkyl and/or $C_1$–$C_4$-alkoxy, or phenyl or benzyl, each of which is optionally substituted by halogen, nitro, $C_1$–$C_6$-alkyl, $C_1$–$C_6$-alkoxy and/or $C_1$–$C_6$-halogenoalkyl.

$R^3$, $R^4$ and $R^5$ independently of one another preferably represent $C_1$–$C_8$-alkyl, $C_1$–$C_8$-alkoxy, $C_1$–$C_8$-alkylamino, di($C_1$–$C_8$)-alkylamino, $C_1$–$C_8$-alkylthio, $C_2$–$C_8$-alkenylthio or $C_3$–$C_7$-cycloalkylthio, each of which is optionally substituted by halogen, or represent phenyl, phenoxy or phenylthio, each of which is optionally substituted by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl.

$R^6$ and $R^7$ independently of one another preferably represent hydrogen, or represent $C_1$–$C_8$-alkyl, $C_3$–$C_8$-cycloalkyl, $C_1$–$C_8$-alkoxy, $C_3$–$C_8$-alkenyl or $C_1$–$C_8$-alkoxy-$C_1$–$C_8$-alkyl, each of which is optionally substituted by halogen, or represent phenyl which is optionally substituted by halogen, $C_1$–$C_8$-halogenoalkyl, $C_1$–$C_8$-alkyl and/or $C_1$–$C_8$-alkoxy, or represent benzyl which is optionally substituted by halogen, $C_1$–$C_6$-alkyl, $C_1$–$C_8$-halogenoalkyl and/or $C_1$–$C_8$-alkoxy, or together represent a $C_3$–$C_6$-alkylene ring which is optionally interrupted by oxygen or sulphur.

G particularly preferably represents hydrogen (a) or one of the groups

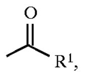 (b)

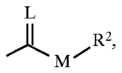 (c)

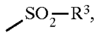 (d)

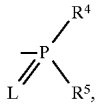 (e)

E (f)

or

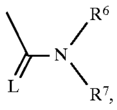 (g)

in which

E represents a metal ion equivalent or an ammonium ion,

L and M in each case represent oxygen or sulphur.

$R^1$ particularly preferably represents $C_1$–$C_{16}$-alkyl, $C_2$–$C_{16}$-alkenyl, $C_1$–$C_6$-alkoxy-$C_1$–$C_6$-alkyl, $C_1$–$C_{16}$-alkylthio-$C_1$–$C_6$-alkyl or $C_1$–$C_6$-polyalkoxy-$C_1$–$C_6$-alkyl, each of which is optionally substituted by fluorine and/or chlorine, or cycloalkyl having 3 to 7 ring atoms which is optionally substituted by halogen or $C_1$–$C_5$-alkyl and which can be interrupted by 1 or 2 oxygen and/or sulphur atoms, phenyl which is optionally substituted by halogen, nitro, $C_1$–$C_4$-alkyl, $C_1$–$C_4$-alkoxy, $C_1$–$C_3$-halogenoalkyl, $C_1$–$C_3$-halogenoalkoxy, $C_1$–$C_4$-alkylthio or $C_1$–$C_4$-alkylsulphonyl, phenyl-$C_1$–$C_4$-alkyl which is optionally substituted by halogen, $C_1$–$C_4$-alkyl, $C_1$–$C_4$-alkoxy, $C_1$–$C_3$-halogenoalkyl or $C_1$–$C_3$-halogenoalkoxy, pyrazolyl, thiazolyl, pyridyl, pyrimidyl, furanyl or thienyl, each of which is optionally substituted by fluorine, chlorine, bromine and/or $C_1$–$C_4$-alkyl, phenoxy-$C_1$–$C_5$-alkyl which is optionally substituted by fluorine, chlorine, bromine and/or $C_1$–$C_4$-alkyl, or pyridyloxy-$C_1$–$C_5$-alkyl, pyrimidyloxy-$C_1$–$C_5$-alkyl or thiazolyloxy-$C_1$–$C_5$-alkyl, each of which is optionally substituted by fluorine, chlorine, bromine, amino and/or $C_1$–$C_4$-alkyl.

$R^2$ particularly preferably represents $C_1$–$C_{16}$-alkyl, $C_3$–$C_{16}$-alkenyl, $C_1$–$C_6$-alkoxy-$C_1$–$C_6$-alkyl or $C_1$–$C_6$-polyalkoxy-$C_1$–$C_6$-alkyl, each of which is optionally substituted by halogen, $C_3$–$C_7$-cycloalkyl which is optionally substituted by halogen, $C_1$–$C_3$-alkyl and/or $C_1$–$C_3$-alkoxy, or phenyl or benzyl, each of which is optionally substituted by halogen, nitro, $C_1$–$C_4$-alkyl, $C_1$–$C_3$-alkoxy and/or $C_1$–$C_3$-halogenoalkyl.

$R^3$, $R^4$ and $R^5$ independently of one another particularly preferably represent $C_1$–$C_6$-alkyl, $C_1$–$C_6$-alkoxy, $C_1$–$C_6$-alkylamino, di-($C_1$–$C_6$)-alkylamino, $C_1$–$C_6$-alkylthio, $C_3$–$C_4$-alkenylthio or $C_3$–$C_6$-cycloalkylthio, each of which is optionally substituted by halogen, or represent phenyl, phenoxy or phenylthio, each of which is optionally substituted by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogenoalkyl.

$R^6$ and $R^7$ independently of one another particularly preferably represent hydrogen, or represent $C_1$–$C_6$-alkyl, $C_3$–$C_6$-cycloalkyl, $C_3$–$C_6$-alkoxy, $C_3$–$C_6$-alkenyl or $C_1$–$C_6$-alkoxy-$C_1$–$C_6$-alkyl, each of which is optionally substituted by halogen, or represent phenyl which is optionally substituted by halogen, $C_1$–$C_5$-halogenoalkyl, $C_1$–$C_5$-alkyl and/or $C_1$–$C_5$-alkoxy, or represent benzyl which is optionally substituted by halogen, $C_1$–$C_5$-alkyl, $C_1$–$C_5$-halogenoalkyl and/or $C_1$–$C_5$-alkoxy, or together represent a $C_3$–$C_6$-alkylene ring which is optionally interrupted by oxygen or sulphur.

G very particularly preferably represents hydrogen (a) or one of the groups

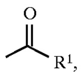 (b)

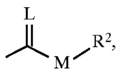 (c)

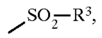 (d)

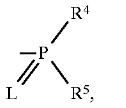 (e)

E (f)

or

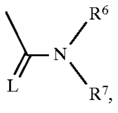 (g)

in which

E represents a metal ion equivalent or an ammonium ion and

L and M in each case represent oxygen or sulphur.

$R^1$ very particularly preferably represents $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl or $C_1$–$C_4$-polyalkoxy-$C_1$–$C_4$-alkyl, each of which is optionally substituted by fluorine and/or chlorine, or cycloalkyl having 3 to 6 ring atoms which is optionally substituted by fluorine, chlorine, methyl, ethyl, propyl, i-propyl, butyl, i-butyl or tert-butyl and which can be interrupted by 1 or 2 oxygen and/or sulphur atoms, phenyl which is optionally substituted by fluorine, chlorine, bromine, nitro, methyl, ethyl, propyl, i-propyl, methoxy, ethoxy, trifluoromethyl, trifluoromethoxy, methylthio, ethylthio, methylsulphonyl or ethylsulphonyl, phenyl-$C_1$–$C_3$-alkyl which is optionally substituted by fluorine, chlorine, bromine, methyl, ethyl, propyl, i-propyl, methoxy, ethoxy, trifluoromethyl or trifluoromethoxy, furanyl, thienyl, pyridyl, pyrimidyl, thiazolyl or pyrazolyl, each of which is optionally substituted by fluorine, chlorine, bromine, methyl or ethyl, phenoxy-$C_1$–$C_4$-alkyl, each of which is optionally substituted by fluorine, chlorine, methyl and/or ethyl, or pyridyloxy-$C_1$–$C_4$-alkyl, pyrimidyloxy-$C_1$–$C_4$-alkyl or thiazolyloxy-$C_1$–$C_4$-alkyl, each of which is optionally substituted by fluorine, chlorine, amino, methyl or ethyl.

$R^2$ very particularly preferably represents $C_1$–$C_{14}$-alkyl, $C_3$–$C_{14}$-alkenyl, $C_1$–$C_4$-alkoxy-$C_1$–$C_6$-alkyl or $C_1$–$C_4$-polyalkoxy-$C_1$–$C_6$-alkyl, each of which is optionally substituted by fluorine and/or chlorine, $C_3$–$C_6$-cycloalkyl which is optionally substituted by fluorine, chlorine, methyl, ethyl, propyl, isopropyl or methoxy, or phenyl or benzyl, each of which is optionally substituted by fluorine, chlorine, nitro, methyl, ethyl, propyl, i-propyl, methoxy, ethoxy or trifluoromethyl.

$R^3$, $R^4$ and $R^5$ independently of one another very particularly preferably represent $C_1$–$C_4$-alkyl, $C_1$–$C_4$-alkoxy, $C_1$–$C_4$-alkylamino, di-($C_1$–$C_4$)-alkylamino or $C_1$–$C_4$-alkylthio, each of which is optionally substituted by fluorine and/or chlorine, or represent phenyl, phenoxy or phenylthio, each of which is optionally substituted by fluorine, chlorine, bromine, nitro, cyano, $C_1$–$C_2$-alkoxy, $C_1$–$C_2$-fluoroalkoxy, $C_1$–$C_2$-alkylthio, $C_1$–$C_2$-fluoroalkylthio or $C_1$–$C_3$-alkyl.

$R^6$ and $R^7$ independently of one another very particularly preferably represent hydrogen, or represent $C_1$–$C_4$-alkyl, $C_3$–$C_6$-cycloalkyl, $C_1$–$C_4$-alkoxy, $C_3$–$C_4$-alkenyl or $C_1$–$C_4$-alkoxy-$C_1$–$C_4$-alkyl, each of which is optionally substituted by fluorine, chlorine, bromine, or represent phenyl which is optionally substituted by fluorine, chlorine, bromine, $C_1$–$C_4$-halogenoalkyl, $C_1$–$C_4$-alkyl and/or $C_1$–$C_4$-alkoxy, or represent benzyl which is optionally substituted by fluorine, chlorine, bromine, $C_1$–$C_4$-alkyl, $C_1$–$C_4$-halogenoalkyl and/or $C_1$–$C_4$-alkoxy, or together represent a $C_4$–$C_6$-alkylene ring which is optionally interrupted by oxygen or sulphur.

In the abovementioned definitions, saturated or unsaturated alkyl radicals, also in connection with hetero atoms such as, for example, alkoxy or alkylthio, can be in each case straight-chain or branched if this is possible.

The abovementioned definitions of radicals or illustrations, in general or where preferred ranges have been mentioned, can be combined with each other as desired, that is to say combinations between the respective ranges and preferred ranges are also possible. They apply to the end products and analogously to the precursors and intermediates.

Preferred according to the invention are those compounds of the general formula (I) in which a combination of the meanings mentioned above as being preferred (preferable) exists.

Particularly preferred according to the invention are those compounds of the general formula (I) in which a combination of the meanings mentioned above as being particularly preferred exists.

Very particularly preferred according to the invention are those compounds of the general formula (I) in which a combination of those meanings mentioned above as being very particularly preferred exists.

The following compounds of the formula (Ia) may be mentioned individually in addition to the compounds mentioned in the preparation examples:

TABLE 1

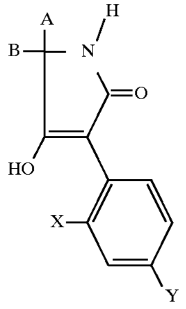

(Ia)

| X | Y | A | B |
|---|---|---|---|
| Cl | $CH_3$ | $CH_3$ | H |
| Cl | $CH_3$ | $C_2H_5$ | H |
| Cl | $CH_3$ | $C_3H_7$ | H |
| Cl | $CH_3$ | i-$C_3H_7$ | H |
| Cl | $CH_3$ | $C_4H_9$ | H |
| Cl | $CH_3$ | i-$C_4H_9$ | H |
| Cl | $CH_3$ | s-$C_4H_9$ | H |
| Cl | $CH_3$ | t-$C_4H_9$ | H |
| Cl | $CH_3$ | $CH_3$ | $CH_3$ |
| Cl | $CH_3$ | $C_2H_5$ | $CH_3$ |
| Cl | $CH_3$ | $C_3H_7$ | $CH_3$ |
| Cl | $CH_3$ | i-$C_3H_7$ | $CH_3$ |
| Cl | $CH_3$ | $C_4H_9$ | $CH_3$ |
| Cl | $CH_3$ | i-$C_4H_9$ | $CH_3$ |
| Cl | $CH_3$ | s-$C_4H_9$ | $CH_3$ |
| Cl | $CH_3$ | t-$C_4H_9$ | $CH_3$ |
| Cl | $CH_3$ | $C_2H_5$ | $C_2H_5$ |
| Cl | $CH_3$ | $C_3H_7$ | $C_3H_7$ |
| Cl | $CH_3$ | 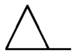 | $CH_3$ |
| Cl | $CH_3$ | 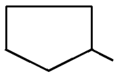 | $CH_3$ |
| Cl | $CH_3$ | 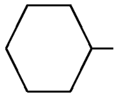 | $CH_3$ |
| $CH_3$ | Cl | $CH_3$ | H |
| $CH_3$ | Cl | $C_2H_5$ | H |
| $CH_3$ | Cl | $C_3H_7$ | H |
| $CH_3$ | Cl | i-$C_3H_7$ | H |
| $CH_3$ | Cl | $C_4H_9$ | H |
| $CH_3$ | Cl | i-$C_4H_9$ | H |
| $CH_3$ | Cl | s-$C_4H_9$ | H |
| $CH_3$ | Cl | t-$C_4H_9$ | H |
| $CH_3$ | Cl | $CH_3$ | $CH_3$ |
| $CH_3$ | Cl | $C_2H_5$ | $CH_3$ |
| $CH_3$ | Cl | $C_3H_7$ | $CH_3$ |
| $CH_3$ | Cl | i-$C_3H_7$ | $CH_3$ |
| $CH_3$ | Cl | $C_4H_9$ | $CH_3$ |
| $CH_3$ | Cl | i-$C_4H_9$ | $CH_3$ |
| $CH_3$ | Cl | s-$C_4H_9$ | $CH_3$ |
| $CH_3$ | Cl | t-$C_4H_9$ | $CH_3$ |

TABLE 1-continued

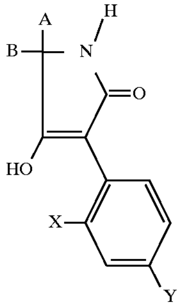

(Ia)

| X | Y | A | B |
|---|---|---|---|
| $CH_3$ | Cl | $C_2H_5$ | $C_2H_5$ |
| $CH_3$ | Cl | $C_3H_7$ | $C_3H_7$ |
| $CH_3$ | Cl | 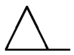 | $CH_3$ |
| $CH_3$ | Cl | 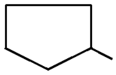 | $CH_3$ |
| $CH_3$ | Cl | 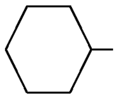 | $CH_3$ |
| Cl | $CH_3$ | $-(CH_2)_2-$ | |
| Cl | $CH_3$ | $-(CH_2)_4-$ | |
| Cl | $CH_3$ | $-(CH_2)_5-$ | |
| Cl | $CH_3$ | $-(CH_2)_6-$ | |
| Cl | $CH_3$ | $-(CH_2)_7-$ | |
| Cl | $CH_3$ | $-(CH_2)_2-O-(CH_2)_2-$ | |
| Cl | $CH_3$ | $-(CH_2)_2-S-(CH_2)_2-$ | |
| Cl | $CH_3$ | $-CH_2-CHCH_3-(CH_2)_3-$ | |
| Cl | $CH_3$ | $-(CH_2)_2-CHCH_3-(CH_2)_2-$ | |
| Cl | $CH_3$ | $-(CH_2)_2-CHC_2H_5-(CH_2)_2-$ | |
| Cl | $CH_3$ | $-(CH_2)_2-CHC_3H_7-(CH_2)_2-$ | |
| Cl | $CH_3$ | $-(CH_2)_2-CHi\text{-}C_3H_7-(CH_2)_2-$ | |
| Cl | $CH_3$ | $-(CH_2)_2-CHOCH_3-(CH_2)_2-$ | |
| Cl | $CH_3$ | $-(CH_2)_2-CHOC_2H_5-(CH_2)_2-$ | |
| Cl | $CH_3$ | $-(CH_2)_2-CHOC_3H_7-(CH_2)_2-$ | |
| Cl | $CH_3$ | $-(CH_2)_2-CHi\text{-}OC_3H_7-(CH_2)_2-$ | |
| Cl | $CH_3$ | $-(CH_2)_2-C(CH_3)_2-(CH_2)_2-$ | |
| Cl | $CH_3$ | $-CH_2-(CHCH_3)_2-(CH_2)_2-$ | |
| Cl | $CH_3$ | $-CH_2-CH-(CH_2)_2-CH-$<br>$CH_2$ | |
| Cl | $CH_3$ | $-CH_2-CH$——$CH-CH_2-$<br>$(CH_2)_4$ | |
| Cl | $CH_3$ | $-CH_2-CH$——$CH-(CH_2)_2-$<br>$(CH_2)_3$ | |
| $CH_3$ | Cl | $-(CH_2)_2-$ | |
| $CH_3$ | Cl | $-(CH_2)_4-$ | |
| $CH_3$ | Cl | $-(CH_2)_5-$ | |
| $CH_3$ | Cl | $-(CH_2)_6-$ | |
| $CH_3$ | Cl | $-(CH_2)_7-$ | |
| $CH_3$ | Cl | $-(CH_2)_2-O-(CH_2)_2-$ | |
| $CH_3$ | Cl | $-(CH_2)_2-S-(CH_2)_2-$ | |
| $CH_3$ | Cl | $-CH_2-CHCH_3-(CH_2)_3-$ | |
| $CH_3$ | Cl | $-(CH_2)_2-CHCH_3-(CH_2)_2-$ | |
| $CH_3$ | Cl | $-(CH_2)_2-CHC_2H_5-(CH_2)_2-$ | |
| $CH_3$ | Cl | $-(CH_2)_2-CHC_3H_7-(CH_2)_2-$ | |
| $CH_3$ | Cl | $-(CH_2)_2-CHi\text{-}C_3H_7-(CH_2)_2-$ | |
| $CH_3$ | Cl | $-(CH_2)_2-CHOCH_3-(CH_2)_2-$ | |
| $CH_3$ | Cl | $-(CH_2)_2-CHOC_2H_5-(CH_2)_2-$ | |
| $CH_3$ | Cl | $-(CH_2)_2-CHOC_3H_7-(CH_2)_2-$ | |
| $CH_3$ | Cl | $-(CH_2)_2-CHi\text{-}OC_3H_7-(CH_2)_2-$ | |
| $CH_3$ | Cl | $-(CH_2)_2-C(CH_3)_2-(CH_2)_2-$ | |

TABLE 1-continued

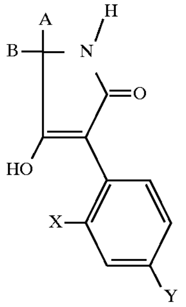

(Ia)

| X | Y | A | B |
|---|---|---|---|
| $CH_3$ | Cl | $-CH_2-(CHCH_3)_2-(CH_2)_2-$ | |
| $CH_3$ | Cl | $-CH_2-CH-(CH_2)_2-CH-$<br>$CH_2$ | |
| $CH_3$ | Cl | $-CH_2-CH$——$CH-CH_2-$<br>$(CH_2)_4$ | |
| $CH_3$ | Cl | $-CH_2-CH$——$CH-(CH_2)_2-$<br>$(CH_2)_3$ | |

The following compounds of the formula (Ib) may be mentioned individually in addition to the compounds mentioned in the preparation examples:

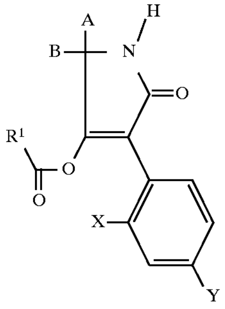

(Ib)

| X | Y | A | B | $R^1$ |
|---|---|---|---|---|
| Cl | $CH_3$ | $CH_3$ | H | $CH_3$ |
| Cl | $CH_3$ | $C_2H_5$ | H | $CH_3$ |
| Cl | $CH_3$ | $C_3H_7$ | H | $CH_3$ |
| Cl | $CH_3$ | $i\text{-}C_3H_7$ | H | $CH_3$ |
| Cl | $CH_3$ | $C_4H_9$ | H | $CH_3$ |
| Cl | $CH_3$ | $i\text{-}C_4H_9$ | H | $CH_3$ |
| Cl | $CH_3$ | $s\text{-}C_4H_9$ | H | $CH_3$ |
| Cl | $CH_3$ | $t\text{-}C_4H_9$ | H | $CH_3$ |
| Cl | $CH_3$ | $CH_3$ | $CH_3$ | $CH_3$ |
| Cl | $CH_3$ | $C_2H_5$ | $CH_3$ | $CH_3$ |
| Cl | $CH_3$ | $C_3H_7$ | $CH_3$ | $CH_3$ |
| Cl | $CH_3$ | $i\text{-}C_3H_7$ | $CH_3$ | $CH_3$ |
| Cl | $CH_3$ | $C_4H_9$ | $CH_3$ | $CH_3$ |
| Cl | $CH_3$ | $i\text{-}C_4H_9$ | $CH_3$ | $CH_3$ |
| Cl | $CH_3$ | $s\text{-}C_4H_9$ | $CH_3$ | $CH_3$ |
| Cl | $CH_3$ | $t\text{-}C_4H_9$ | $CH_3$ | $CH_3$ |
| Cl | $CH_3$ | $C_2H_5$ | $C_2H_5$ | $CH_3$ |
| Cl | $CH_3$ | $C_3H_7$ | $C_3H_7$ | $CH_3$ |
| Cl | $CH_3$ | 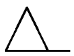 | $CH_3$ | $CH_3$ |
| Cl | $CH_3$ | 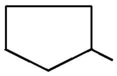 | $CH_3$ | $CH_3$ |

-continued

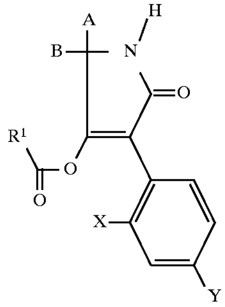

(Ib)

| X | Y | A | B | $R^1$ |
|---|---|---|---|---|
| Cl | $CH_3$ | 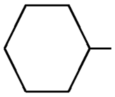 | $CH_3$ | $CH_3$ |
| $CH_3$ | Cl | $CH_3$ | H | $CH_3$ |
| $CH_3$ | Cl | $C_2H_5$ | H | $CH_3$ |
| $CH_3$ | Cl | $C_3H_7$ | H | $CH_3$ |
| $CH_3$ | Cl | $i\text{-}C_3H_7$ | H | $CH_3$ |
| $CH_3$ | Cl | $C_4H_9$ | H | $CH_3$ |
| $CH_3$ | Cl | $i\text{-}C_4H_9$ | H | $CH_3$ |
| $CH_3$ | Cl | $s\text{-}C_4H_9$ | H | $CH_3$ |
| $CH_3$ | Cl | $t\text{-}C_4H_9$ | H | $CH_3$ |
| $CH_3$ | Cl | $CH_3$ | $CH_3$ | $CH_3$ |
| $CH_3$ | Cl | $C_2H_5$ | $CH_3$ | $CH_3$ |
| $CH_3$ | Cl | $C_3H_7$ | $CH_3$ | $CH_3$ |
| $CH_3$ | Cl | $i\text{-}C_3H_7$ | $CH_3$ | $CH_3$ |
| $CH_3$ | Cl | $C_4H_9$ | $CH_3$ | $CH_3$ |
| $CH_3$ | Cl | $i\text{-}C_4H_9$ | $CH_3$ | $CH_3$ |
| $CH_3$ | Cl | $s\text{-}C_4H_9$ | $CH_3$ | $CH_3$ |
| $CH_3$ | Cl | $t\text{-}C_4H_9$ | $CH_3$ | $CH_3$ |
| $CH_3$ | Cl | $C_2H_5$ | $C_2H_5$ | $CH_3$ |
| $CH_3$ | Cl | $C_3H_7$ | $C_3H_7$ | $CH_3$ |
| $CH_3$ | Cl | 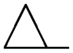 | $CH_3$ | $CH_3$ |
| $CH_3$ | Cl | 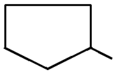 | $CH_3$ | $CH_3$ |
| $CH_3$ | Cl | 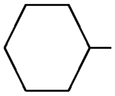 | $CH_3$ | $CH_3$ |
| Cl | $CH_3$ | $-(CH_2)_2-$ | | $CH_3$ |
| Cl | $CH_3$ | $-(CH_2)_4-$ | | $CH_3$ |
| Cl | $CH_3$ | $-(CH_2)_5-$ | | $CH_3$ |
| Cl | $CH_3$ | $-(CH_2)_6-$ | | $CH_3$ |
| Cl | $CH_3$ | $-(CH_2)_7-$ | | $CH_3$ |
| Cl | $CH_3$ | $-(CH_2)_2-O-(CH_2)_2-$ | | $CH_3$ |
| Cl | $CH_3$ | $-(CH_2)_2-S-(CH_2)_2-$ | | $CH_3$ |
| Cl | $CH_3$ | $-CH_2-CHCH_3-(CH_2)_3-$ | | $CH_3$ |
| Cl | $CH_3$ | $-(CH_2)_2-CHCH_3-(CH_2)_2-$ | | $CH_3$ |
| Cl | $CH_3$ | $-(CH_2)_2-CHC_2H_5-(CH_2)_2-$ | | $CH_3$ |
| Cl | $CH_3$ | $-(CH_2)_2-CHC_3H_7-(CH_2)_2-$ | | $CH_3$ |
| Cl | $CH_3$ | $-(CH_2)_2-CHi\text{-}C_3H_7-(CH_2)_2-$ | | $CH_3$ |
| Cl | $CH_3$ | $-(CH_2)_2-CHOCH_3-(CH_2)_2-$ | | $CH_3$ |
| Cl | $CH_3$ | $-(CH_2)_2-CHOC_2H_5-(CH_2)_2-$ | | $CH_3$ |
| Cl | $CH_3$ | $-(CH_2)_2-CHOC_3H_7-(CH_2)_2-$ | | $CH_3$ |
| Cl | $CH_3$ | $-(CH_2)_2-CHi\text{-}OC_3H_7-(CH_2)_2-$ | | $CH_3$ |
| Cl | $CH_3$ | $-(CH_2)_2-C(CH_3)_2-(CH_2)_2-$ | | $CH_3$ |
| Cl | $CH_3$ | $-CH_2-(CHCH_3)_2-(CH_2)_2-$ | | $CH_3$ |
| Cl | $CH_3$ | $-CH_2-CH-(CH_2)_2-CH-$<br>$CH_2$ | | $CH_3$ |
| Cl | $CH_3$ | $-CH_2-CH-CH-CH_2-$<br>$(CH_2)_4$ | | $CH_3$ |

-continued

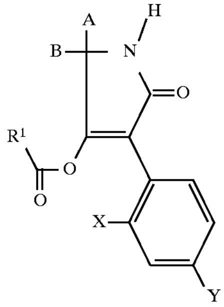

(Ib)

| X | Y | A | B | $R^1$ |
|---|---|---|---|---|
| Cl | $CH_3$ | $-CH_2-CH-CH-(CH_2)_2-$<br>$(CH_2)_3$ | | $CH_3$ |
| $CH_3$ | Cl | $-(CH_2)_2-$ | | $CH_3$ |
| $CH_3$ | Cl | $-(CH_2)_4-$ | | $CH_3$ |
| $CH_3$ | Cl | $-(CH_2)_5-$ | | $CH_3$ |
| $CH_3$ | Cl | $-(CH_2)_6-$ | | $CH_3$ |
| $CH_3$ | Cl | $-(CH_2)_7-$ | | $CH_3$ |
| $CH_3$ | Cl | $-(CH_2)_2-O-(CH_2)_2-$ | | $CH_3$ |
| $CH_3$ | Cl | $-(CH_2)_2-S-(CH_2)_2-$ | | $CH_3$ |
| $CH_3$ | Cl | $-CH_2-CHCH_3-(CH_2)_3-$ | | $CH_3$ |
| $CH_3$ | Cl | $-(CH_2)_2-CHCH_3-(CH_2)_2-$ | | $CH_3$ |
| $CH_3$ | Cl | $-(CH_2)_2-CHC_2H_5-(CH_2)_2-$ | | $CH_3$ |
| $CH_3$ | Cl | $-(CH_2)_2-CHC_3H_7-(CH_2)_2-$ | | $CH_3$ |
| $CH_3$ | Cl | $-(CH_2)_2-CHi\text{-}C_3H_7-(CH_2)_2-$ | | $CH_3$ |
| $CH_3$ | Cl | $-(CH_2)_2-CHOCH_3-(CH_2)_2-$ | | $CH_3$ |
| $CH_3$ | Cl | $-(CH_2)_2-CHOC_2H_5-(CH_2)_2-$ | | $CH_3$ |
| $CH_3$ | Cl | $-(CH_2)_2-CHOC_3H_7-(CH_2)_2-$ | | $CH_3$ |
| $CH_3$ | Cl | $-(CH_2)_2-CHi\text{-}OC_3H_7-(CH_2)_2-$ | | $CH_3$ |
| $CH_3$ | Cl | $-(CH_2)_2-C(CH_3)_2-(CH_2)_2-$ | | $CH_3$ |
| $CH_3$ | Cl | $-CH_2-(CHCH_3)_2-(CH_2)_2-$ | | $CH_3$ |
| $CH_3$ | Cl | $-CH_2-CH-(CH_2)_2-CH-$<br>$CH_2$ | | $CH_3$ |
| $CH_3$ | Cl | $-CH_2-CH-CH-CH_2-$<br>$(CH_2)_4$ | | $CH_3$ |
| $CH_3$ | Cl | $-CH_2-CH-CH-(CH_2)_2-$<br>$(CH_2)_3$ | | $CH_3$ |
| Cl | $CH_3$ | $CH_3$ | H | $i\text{-}C_3H_7$ |
| Cl | $CH_3$ | $C_2H_5$ | H | $i\text{-}C_3H_7$ |
| Cl | $CH_3$ | $C_3H_7$ | H | $i\text{-}C_3H_7$ |
| Cl | $CH_3$ | $i\text{-}C_3H_7$ | H | $i\text{-}C_3H_7$ |
| Cl | $CH_3$ | $C_4H_9$ | H | $i\text{-}C_3H_7$ |
| Cl | $CH_3$ | $i\text{-}C_4H_9$ | H | $i\text{-}C_3H_7$ |
| Cl | $CH_3$ | $s\text{-}C_4H_9$ | H | $i\text{-}C_3H_7$ |
| Cl | $CH_3$ | $t\text{-}C_4H_9$ | H | $i\text{-}C_3H_7$ |
| Cl | $CH_3$ | $CH_3$ | $CH_3$ | $i\text{-}C_3H_7$ |
| Cl | $CH_3$ | $C_2H_5$ | $CH_3$ | $i\text{-}C_3H_7$ |
| Cl | $CH_3$ | $C_3H_7$ | $CH_3$ | $i\text{-}C_3H_7$ |
| Cl | $CH_3$ | $i\text{-}C_3H_7$ | $CH_3$ | $i\text{-}C_3H_7$ |
| Cl | $CH_3$ | $C_4H_9$ | $CH_3$ | $i\text{-}C_3H_7$ |
| Cl | $CH_3$ | $i\text{-}C_4H_9$ | $CH_3$ | $i\text{-}C_3H_7$ |
| Cl | $CH_3$ | $s\text{-}C_4H_9$ | $CH_3$ | $i\text{-}C_3H_7$ |
| Cl | $CH_3$ | $t\text{-}C_4H_9$ | $CH_3$ | $i\text{-}C_3H_7$ |
| Cl | $CH_3$ | $C_2H_5$ | $C_2H_5$ | $i\text{-}C_3H_7$ |
| Cl | $CH_3$ | $C_3H_7$ | $C_3H_7$ | $i\text{-}C_3H_7$ |
| Cl | $CH_3$ | 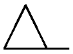 | $CH_3$ | $i\text{-}C_3H_7$ |
| Cl | $CH_3$ | 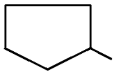 | $CH_3$ | $i\text{-}C_3H_7$ |

-continued (Ib)

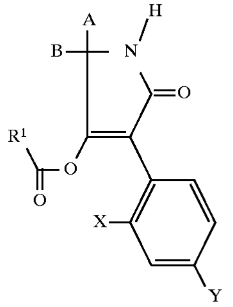

| X | Y | A | B | $R^1$ |
|---|---|---|---|---|
| Cl | $CH_3$ | 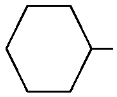 | $CH_3$ | i-$C_3H_7$ |
| $CH_3$ | Cl | $CH_3$ | H | i-$C_3H_7$ |
| $CH_3$ | Cl | $C_2H_5$ | H | i-$C_3H_7$ |
| $CH_3$ | Cl | $C_3H_7$ | H | i-$C_3H_7$ |
| $CH_3$ | Cl | i-$C_3H_7$ | H | i-$C_3H_7$ |
| $CH_3$ | Cl | $C_4H_9$ | H | i-$C_3H_7$ |
| $CH_3$ | Cl | i-$C_4H_9$ | H | i-$C_3H_7$ |
| $CH_3$ | Cl | s-$C_4H_9$ | H | i-$C_3H_7$ |
| $CH_3$ | Cl | t-$C_4H_9$ | H | i-$C_3H_7$ |
| $CH_3$ | Cl | $CH_3$ | $CH_3$ | i-$C_3H_7$ |
| $CH_3$ | Cl | $C_2H_5$ | $CH_3$ | i-$C_3H_7$ |
| $CH_3$ | Cl | $C_3H_7$ | $CH_3$ | i-$C_3H_7$ |
| $CH_3$ | Cl | i-$C_3H_7$ | $CH_3$ | i-$C_3H_7$ |
| $CH_3$ | Cl | $C_4H_9$ | $CH_3$ | i-$C_3H_7$ |
| $CH_3$ | Cl | i-$C_4H_9$ | $CH_3$ | i-$C_3H_7$ |
| $CH_3$ | Cl | s-$C_4H_9$ | $CH_3$ | i-$C_3H_7$ |
| $CH_3$ | Cl | t-$C_4H_9$ | $CH_3$ | i-$C_3H_7$ |
| $CH_3$ | Cl | $C_2H_5$ | $C_2H_5$ | i-$C_3H_7$ |
| $CH_3$ | Cl | $C_3H_7$ | $C_3H_7$ | i-$C_3H_7$ |
| $CH_3$ | Cl | 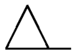 | $CH_3$ | i-$C_3H_7$ |
| $CH_3$ | Cl | 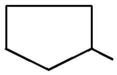 | $CH_3$ | i-$C_3H_7$ |
| $CH_3$ | Cl | 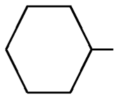 | $CH_3$ | i-$C_3H_7$ |
| Cl | $CH_3$ | $-(CH_2)_2-$ | | i-$C_3H_7$ |
| Cl | $CH_3$ | $-(CH_2)_4-$ | | i-$C_3H_7$ |
| Cl | $CH_3$ | $-(CH_2)_5-$ | | i-$C_3H_7$ |
| Cl | $CH_3$ | $-(CH_2)_6-$ | | i-$C_3H_7$ |
| Cl | $CH_3$ | $-(CH_2)_7-$ | | i-$C_3H_7$ |
| Cl | $CH_3$ | $-(CH_2)_2-O-(CH_2)_2-$ | | i-$C_3H_7$ |
| Cl | $CH_3$ | $-(CH_2)_2-S-(CH_2)_2-$ | | i-$C_3H_7$ |
| Cl | $CH_3$ | $-CH_2-CHCH_3-(CH_2)_3-$ | | i-$C_3H_7$ |
| Cl | $CH_3$ | $-(CH_2)_2-CHCH_3-(CH_2)_2-$ | | i-$C_3H_7$ |
| Cl | $CH_3$ | $-(CH_2)_2-CHC_2H_5-(CH_2)_2-$ | | i-$C_3H_7$ |
| Cl | $CH_3$ | $-(CH_2)_2-CHC_3H_7-(CH_2)_2-$ | | i-$C_3H_7$ |
| Cl | $CH_3$ | $-(CH_2)_2-$CHi-$C_3H_7-(CH_2)_2-$ | | i-$C_3H_7$ |
| Cl | $CH_3$ | $-(CH_2)_2-CHOCH_3-(CH_2)_2-$ | | i-$C_3H_7$ |
| Cl | $CH_3$ | $-(CH_2)_2-CHOC_2H_5-(CH_2)_2-$ | | i-$C_3H_7$ |
| Cl | $CH_3$ | $-(CH_2)_2-CHOC_3H_7-(CH_2)_2-$ | | i-$C_3H_7$ |
| Cl | $CH_3$ | $-(CH_2)_2-$CHi-$OC_3H_7-(CH_2)_2-$ | | i-$C_3H_7$ |
| Cl | $CH_3$ | $-(CH_2)_2-C(CH_3)_2-(CH_2)_2-$ | | i-$C_3H_7$ |
| Cl | $CH_3$ | $-CH_2-(CHCH_3)_2-(CH_2)_2-$ | | i-$C_3H_7$ |
| Cl | $CH_3$ | $-CH_2-CH-(CH_2)_2-CH-$<br>$CH_2$ | | i-$C_3H_7$ |
| Cl | $CH_3$ | $-CH_2-CH-CH-CH_2-$<br>$(CH_2)_4$ | | i-$C_3H_7$ |

-continued (Ib)

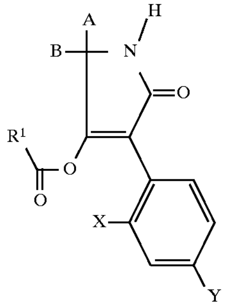

| X | Y | A | B | $R^1$ |
|---|---|---|---|---|
| Cl | $CH_3$ | $-CH_2-CH-CH-(CH_2)_2-$<br>$(CH_2)_3$ | | i-$C_3H_7$ |
| $CH_3$ | Cl | $-(CH_2)_2-$ | | i-$C_3H_7$ |
| $CH_3$ | Cl | $-(CH_2)_4-$ | | i-$C_3H_7$ |
| $CH_3$ | Cl | $-(CH_2)_5-$ | | i-$C_3H_7$ |
| $CH_3$ | Cl | $-(CH_2)_6-$ | | i-$C_3H_7$ |
| $CH_3$ | Cl | $-(CH_2)_7-$ | | i-$C_3H_7$ |
| $CH_3$ | Cl | $-(CH_2)_2-O-(CH_2)_2-$ | | i-$C_3H_7$ |
| $CH_3$ | Cl | $-(CH_2)_2-S-(CH_2)_2-$ | | i-$C_3H_7$ |
| $CH_3$ | Cl | $-CH_2-CHCH_3-(CH_2)_3-$ | | i-$C_3H_7$ |
| $CH_3$ | Cl | $-(CH_2)_2-CHCH_3-(CH_2)_2-$ | | i-$C_3H_7$ |
| $CH_3$ | Cl | $-(CH_2)_2-CHC_2H_5-(CH_2)_2-$ | | i-$C_3H_7$ |
| $CH_3$ | Cl | $-(CH_2)_2-CHC_3H_7-(CH_2)_2-$ | | i-$C_3H_7$ |
| $CH_3$ | Cl | $-(CH_2)_2-$CHi-$C_3H_7-(CH_2)_2-$ | | i-$C_3H_7$ |
| $CH_3$ | Cl | $-(CH_2)_2-CHOCH_3-(CH_2)_2-$ | | i-$C_3H_7$ |
| $CH_3$ | Cl | $-(CH_2)_2-CHOC_2H_5-(CH_2)_2-$ | | i-$C_3H_7$ |
| $CH_3$ | Cl | $-(CH_2)_2-CHOC_3H_7-(CH_2)_2-$ | | i-$C_3H_7$ |
| $CH_3$ | Cl | $-(CH_2)_2-$CHi-$OC_3H_7-(CH_2)_2-$ | | i-$C_3H_7$ |
| $CH_3$ | Cl | $-(CH_2)_2-C(CH_3)_2-(CH_2)_2-$ | | i-$C_3H_7$ |
| $CH_3$ | Cl | $-CH_2-(CHCH_3)_2-(CH_2)_2-$ | | i-$C_3H_7$ |
| $CH_3$ | Cl | $-CH_2-CH-(CH_2)_2-CH-$<br>$CH_2$ | | i-$C_3H_7$ |
| $CH_3$ | Cl | $-CH_2-CH-CH-CH_2-$<br>$(CH_2)_4$ | | i-$C_3H_7$ |
| $CH_3$ | Cl | $-CH_2-CH-CH-(CH_2)_2-$<br>$(CH_2)_3$ | | i-$C_3H_7$ |
| Cl | $CH_3$ | $CH_3$ | H | t-$C_4H_9$ |
| Cl | $CH_3$ | $C_2H_5$ | H | t-$C_4H_9$ |
| Cl | $CH_3$ | $C_3H_7$ | H | t-$C_4H_9$ |
| Cl | $CH_3$ | i-$C_3H_7$ | H | t-$C_4H_9$ |
| Cl | $CH_3$ | $C_4H_9$ | H | t-$C_4H_9$ |
| Cl | $CH_3$ | i-$C_4H_9$ | H | t-$C_4H_9$ |
| Cl | $CH_3$ | s-$C_4H_9$ | H | t-$C_4H_9$ |
| Cl | $CH_3$ | t-$C_4H_9$ | H | t-$C_4H_9$ |
| Cl | $CH_3$ | $CH_3$ | $CH_3$ | t-$C_4H_9$ |
| Cl | $CH_3$ | $C_2H_5$ | $CH_3$ | t-$C_4H_9$ |
| Cl | $CH_3$ | $C_3H_7$ | $CH_3$ | t-$C_4H_9$ |
| Cl | $CH_3$ | i-$C_3H_7$ | $CH_3$ | t-$C_4H_9$ |
| Cl | $CH_3$ | $C_4H_9$ | $CH_3$ | t-$C_4H_9$ |
| Cl | $CH_3$ | i-$C_4H_9$ | $CH_3$ | t-$C_4H_9$ |
| Cl | $CH_3$ | s-$C_4H_9$ | $CH_3$ | t-$C_4H_9$ |
| Cl | $CH_3$ | t-$C_4H_9$ | $CH_3$ | t-$C_4H_9$ |
| Cl | $CH_3$ | $C_2H_5$ | $C_2H_5$ | t-$C_4H_9$ |
| Cl | $CH_3$ | $C_3H_7$ | $C_3H_7$ | t-$C_4H_9$ |
| Cl | $CH_3$ | 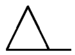 | $CH_3$ | t-$C_4H_9$ |
| Cl | $CH_3$ | 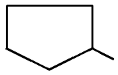 | $CH_3$ | t-$C_4H_9$ |
| Cl | $CH_3$ | 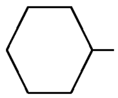 | $CH_3$ | t-$C_4H_9$ |

-continued

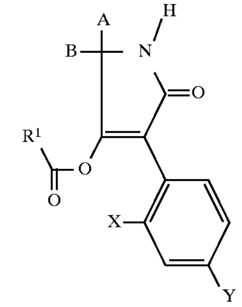

(Ib)

| X | Y | A | B | $R^1$ |
|---|---|---|---|---|
| $CH_3$ | Cl | $CH_3$ | H | t-$C_4H_9$ |
| $CH_3$ | Cl | $C_2H_5$ | H | t-$C_4H_9$ |
| $CH_3$ | Cl | $C_3H_7$ | H | t-$C_4H_9$ |
| $CH_3$ | Cl | i-$C_3H_7$ | H | t-$C_4H_9$ |
| $CH_3$ | Cl | $C_4H_9$ | H | t-$C_4H_9$ |
| $CH_3$ | Cl | i-$C_4H_9$ | H | t-$C_4H_9$ |
| $CH_3$ | Cl | s-$C_4H_9$ | H | t-$C_4H_9$ |
| $CH_3$ | Cl | t-$C_4H_9$ | H | t-$C_4H_9$ |
| $CH_3$ | Cl | $CH_3$ | $CH_3$ | t-$C_4H_9$ |
| $CH_3$ | Cl | $C_2H_5$ | $CH_3$ | t-$C_4H_9$ |
| $CH_3$ | Cl | $C_3H_7$ | $CH_3$ | t-$C_4H_9$ |
| $CH_3$ | Cl | i-$C_3H_7$ | $CH_3$ | t-$C_4H_9$ |
| $CH_3$ | Cl | $C_4H_9$ | $CH_3$ | t-$C_4H_9$ |
| $CH_3$ | Cl | i-$C_4H_9$ | $CH_3$ | t-$C_4H_9$ |
| $CH_3$ | Cl | s-$C_4H_9$ | $CH_3$ | t-$C_4H_9$ |
| $CH_3$ | Cl | t-$C_4H_9$ | $CH_3$ | t-$C_4H_9$ |
| $CH_3$ | Cl | $C_2H_5$ | $C_2H_5$ | t-$C_4H_9$ |
| $CH_3$ | Cl | $C_3H_7$ | $C_3H_7$ | t-$C_4H_9$ |
| $CH_3$ | Cl | 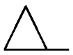 | $CH_3$ | t-$C_4H_9$ |
| $CH_3$ | Cl | 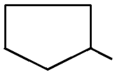 | $CH_3$ | t-$C_4H_9$ |
| $CH_3$ | Cl | 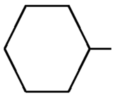 | $CH_3$ | t-$C_4H_9$ |
| Cl | $CH_3$ | | $-(CH_2)_2-$ | t-$C_4H_9$ |
| Cl | $CH_3$ | | $-(CH_2)_4-$ | t-$C_4H_9$ |
| Cl | $CH_3$ | | $-(CH_2)_5-$ | t-$C_4H_9$ |
| Cl | $CH_3$ | | $-(CH_2)_6-$ | t-$C_4H_9$ |
| Cl | $CH_3$ | | $-(CH_2)_7-$ | t-$C_4H_9$ |
| Cl | $CH_3$ | | $-(CH_2)_2-O-(CH_2)_2-$ | t-$C_4H_9$ |
| Cl | $CH_3$ | | $-(CH_2)_2-S-(CH_2)_2-$ | t-$C_4H_9$ |
| Cl | $CH_3$ | | $-CH_2-CHCH_3-(CH_2)_3-$ | t-$C_4H_9$ |
| Cl | $CH_3$ | | $-(CH_2)_2-CHCH_3-(CH_2)_2-$ | t-$C_4H_9$ |
| Cl | $CH_3$ | | $-(CH_2)_2-CHC_2H_5-(CH_2)_2-$ | t-$C_4H_9$ |
| Cl | $CH_3$ | | $-(CH_2)_2-CHC_3H_7-(CH_2)_2-$ | t-$C_4H_9$ |
| Cl | $CH_3$ | | $-(CH_2)_2-CHi\text{-}C_3H_7-(CH_2)_2-$ | t-$C_4H_9$ |
| Cl | $CH_3$ | | $-(CH_2)_2-CHOCH_3-(CH_2)_2-$ | t-$C_4H_9$ |
| Cl | $CH_3$ | | $-(CH_2)_2-CHOC_2H_5-(CH_2)_2-$ | t-$C_4H_9$ |
| Cl | $CH_3$ | | $-(CH_2)_2-CHOC_3H_7-(CH_2)_2-$ | t-$C_4H_9$ |
| Cl | $CH_3$ | | $-(CH_2)_2-CHi\text{-}OC_3H_7-(CH_2)_2-$ | t-$C_4H_9$ |

-continued

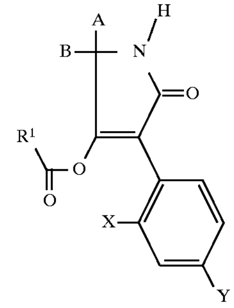

(Ib)

| X | Y | A | B | $R^1$ |
|---|---|---|---|---|
| Cl | $CH_3$ | | $-(CH_2)_2-C(CH_3)_2-(CH_2)_2-$ | t-$C_4H_9$ |
| Cl | $CH_3$ | | $-CH_2-(CHCH_3)_2-(CH_2)_2-$ | t-$C_4H_9$ |
| Cl | $CH_3$ | | 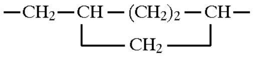 | t-$C_4H_9$ |
| Cl | $CH_3$ | | 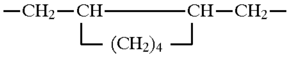 | t-$C_4H_9$ |
| Cl | $CH_3$ | | 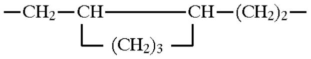 | t-$C_4H_9$ |
| $CH_3$ | Cl | | $-(CH_2)_2-$ | t-$C_4H_9$ |
| $CH_3$ | Cl | | $-(CH_2)_4-$ | t-$C_4H_9$ |
| $CH_3$ | Cl | | $-(CH_2)_5-$ | t-$C_4H_9$ |
| $CH_3$ | Cl | | $-(CH_2)_6-$ | t-$C_4H_9$ |
| $CH_3$ | Cl | | $-(CH_2)_7-$ | t-$C_4H_9$ |
| $CH_3$ | Cl | | $-(CH_2)_2-O-(CH_2)_2-$ | t-$C_4H_9$ |
| $CH_3$ | Cl | | $-(CH_2)_2-S-(CH_2)_2-$ | t-$C_4H_9$ |
| $CH_3$ | Cl | | $-CH_2-CHCH_3-(CH_2)_3-$ | t-$C_4H_9$ |
| $CH_3$ | Cl | | $-(CH_2)_2-CHCH_3-(CH_2)_2-$ | t-$C_4H_9$ |
| $CH_3$ | Cl | | $-(CH_2)_2-CHC_2H_5-(CH_2)_2-$ | t-$C_4H_9$ |
| $CH_3$ | Cl | | $-(CH_2)_2-CHC_3H_7-(CH_2)_2-$ | t-$C_4H_9$ |
| $CH_3$ | Cl | | $-(CH_2)_2-CHi\text{-}C_3H_7-(CH_2)_2-$ | t-$C_4H_9$ |
| $CH_3$ | Cl | | $-(CH_2)_2-CHOCH_3-(CH_2)_2-$ | t-$C_4H_9$ |
| $CH_3$ | Cl | | $-(CH_2)_2-CHOC_2H_5-(CH_2)_2-$ | t-$C_4H_9$ |
| $CH_3$ | Cl | | $-(CH_2)_2-CHOC_3H_7-(CH_2)_2-$ | t-$C_4H_9$ |
| $CH_3$ | Cl | | $-(CH_2)_2-CHi\text{-}OC_3H_7-(CH_2)_2-$ | t-$C_4H_9$ |
| $CH_3$ | Cl | | $-(CH_2)_2-C(CH_3)_2-(CH_2)_2-$ | t-$C_4H_9$ |
| $CH_3$ | Cl | | $-CH_2-(CHCH_3)_2-(CH_2)_2-$ | t-$C_4H_9$ |
| $CH_3$ | Cl | | 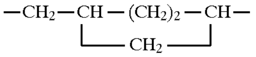 | t-$C_4H_9$ |
| $CH_3$ | Cl | | 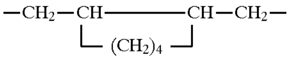 | t-$C_4H_9$ |
| $CH_3$ | Cl | | 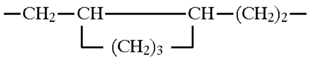 | t-$C_4H_9$ |

The following compounds of the formula (Ic) may be mentioned individually in addition to the compounds mentioned in the preparation examples:

TABLE 3

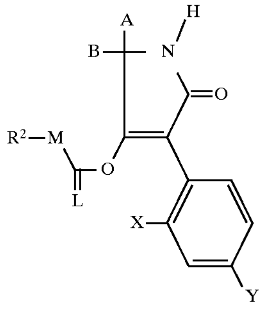
(Ic)

| X | Y | A | B | L | M | $R^2$ |
|---|---|---|---|---|---|---|
| Cl | $CH_3$ | $CH_3$ | H | O | O | $C_2H_5$ |
| Cl | $CH_3$ | $C_2H_5$ | H | O | O | $C_2H_5$ |
| Cl | $CH_3$ | $C_3H_7$ | H | O | O | $C_2H_5$ |
| Cl | $CH_3$ | i-$C_3H_7$ | H | O | O | $C_2H_5$ |
| Cl | $CH_3$ | $C_4H_9$ | H | O | O | $C_2H_5$ |
| Cl | $CH_3$ | i-$C_4H_9$ | H | O | O | $C_2H_5$ |
| Cl | $CH_3$ | s-$C_4H_9$ | H | O | O | $C_2H_5$ |
| Cl | $CH_3$ | t-$C_4H_9$ | H | O | O | $C_2H_5$ |
| Cl | $CH_3$ | $CH_3$ | $CH_3$ | O | O | $C_2H_5$ |
| Cl | $CH_3$ | $C_2H_5$ | $CH_3$ | O | O | $C_2H_5$ |
| Cl | $CH_3$ | $C_3H_7$ | $CH_3$ | O | O | $C_2H_5$ |
| Cl | $CH_3$ | i-$C_3H_7$ | $CH_3$ | O | O | $C_2H_5$ |
| Cl | $CH_3$ | $C_4H_9$ | $CH_3$ | O | O | $C_2H_5$ |
| Cl | $CH_3$ | i-$C_4H_9$ | $CH_3$ | O | O | $C_2H_5$ |
| Cl | $CH_3$ | s-$C_4H_9$ | $CH_3$ | O | O | $C_2H_5$ |
| Cl | $CH_3$ | t-$C_4H_9$ | $CH_3$ | O | O | $C_2H_5$ |
| Cl | $CH_3$ | $C_2H_5$ | $C_2H_5$ | O | O | $C_2H_5$ |
| Cl | $CH_3$ | $C_3H_7$ | $C_3H_7$ | O | O | $C_2H_5$ |
| Cl | $CH_3$ | 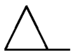 | $CH_3$ | O | O | $C_2H_5$ |
| Cl | $CH_3$ | 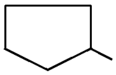 | $CH_3$ | O | O | $C_2H_5$ |
| Cl | $CH_3$ | 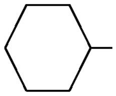 | $CH_3$ | O | O | $C_2H_5$ |
| $CH_3$ | Cl | $CH_3$ | H | O | O | $C_2H_5$ |
| $CH_3$ | Cl | $C_2H_5$ | H | O | O | $C_2H_5$ |
| $CH_3$ | Cl | $C_3H_7$ | H | O | O | $C_2H_5$ |
| $CH_3$ | Cl | i-$C_3H_7$ | H | O | O | $C_2H_5$ |
| $CH_3$ | Cl | $C_4H_9$ | H | O | O | $C_2H_5$ |
| $CH_3$ | Cl | i-$C_4H_9$ | H | O | O | $C_2H_5$ |
| $CH_3$ | Cl | s-$C_4H_9$ | H | O | O | $C_2H_5$ |
| $CH_3$ | Cl | t-$C_4H_9$ | H | O | O | $C_2H_5$ |
| $CH_3$ | Cl | $CH_3$ | $CH_3$ | O | O | $C_2H_5$ |
| $CH_3$ | Cl | $C_2H_5$ | $CH_3$ | O | O | $C_2H_5$ |
| $CH_3$ | Cl | $C_3H_7$ | $CH_3$ | O | O | $C_2H_5$ |
| $CH_3$ | Cl | i-$C_3H_7$ | $CH_3$ | O | O | $C_2H_5$ |
| $CH_3$ | Cl | $C_4H_9$ | $CH_3$ | O | O | $C_2H_5$ |
| $CH_3$ | Cl | i-$C_4H_9$ | $CH_3$ | O | O | $C_2H_5$ |
| $CH_3$ | Cl | s-$C_4H_9$ | $CH_3$ | O | O | $C_2H_5$ |
| $CH_3$ | Cl | t-$C_4H_9$ | $CH_3$ | O | O | $C_2H_5$ |
| $CH_3$ | Cl | $C_2H_5$ | $C_2H_5$ | O | O | $C_2H_5$ |
| $CH_3$ | Cl | $C_3H_7$ | $C_3H_7$ | O | O | $C_2H_5$ |
| $CH_3$ | Cl | 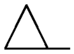 | $CH_3$ | O | O | $C_2H_5$ |
| $CH_3$ | Cl | 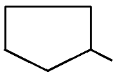 | $CH_3$ | O | O | $C_2H_5$ |

TABLE 3-continued

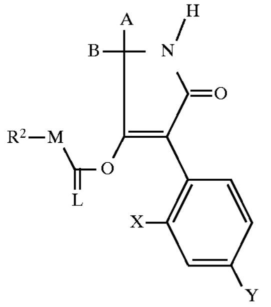

(Ic)

| X | Y | A | B | L | M | $R^2$ |
|---|---|---|---|---|---|---|
| $CH_3$ | Cl | 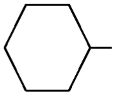 | $CH_3$ | O | O | $C_2H_5$ |
| Cl | $CH_3$ | $-(CH_2)_2-$ | | O | O | $C_2H_5$ |
| Cl | $CH_3$ | $-(CH_2)_4-$ | | O | O | $C_2H_5$ |
| Cl | $CH_3$ | $-(CH_2)_5-$ | | O | O | $C_2H_5$ |
| Cl | $CH_3$ | $-(CH_2)_6-$ | | O | O | $C_2H_5$ |
| Cl | $CH_3$ | $-(CH_2)_7-$ | | O | O | $C_2H_5$ |
| Cl | $CH_3$ | $-(CH_2)_2-O-(CH_2)_2-$ | | O | O | $C_2H_5$ |
| Cl | $CH_3$ | $-(CH_2)_2-S-(CH_2)_2-$ | | O | O | $C_2H_5$ |
| Cl | $CH_3$ | $-CH_2-CHCH_3-(CH_2)_3-$ | | O | O | $C_2H_5$ |
| Cl | $CH_3$ | $-(CH_2)_2-CHCH_3-(CH_2)_2-$ | | O | O | $C_2H_5$ |
| Cl | $CH_3$ | $-(CH_2)_2-CHC_2H_5-(CH_2)_2-$ | | O | O | $C_2H_5$ |
| Cl | $CH_3$ | $-(CH_2)_2-CHC_3H_7-(CH_2)_2-$ | | O | O | $C_2H_5$ |
| Cl | $CH_3$ | $-(CH_2)_2-CHi\text{-}C_3H_7-(CH_2)_2-$ | | O | O | $C_2H_5$ |
| Cl | $CH_3$ | $-(CH_2)_2-CHOCH_3-(CH_2)_2-$ | | O | O | $C_2H_5$ |
| Cl | $CH_3$ | $-(CH_2)_2-CHOC_2H_5-(CH_2)_2-$ | | O | O | $C_2H_5$ |
| Cl | $CH_3$ | $-(CH_2)_2-CHOC_3H_7-(CH_2)_2-$ | | O | O | $C_2H_5$ |
| Cl | $CH_3$ | $-(CH_2)_2-CHi\text{-}OC_3H_7-(CH_2)_2-$ | | O | O | $C_2H_5$ |
| Cl | $CH_3$ | $-(CH_2)_2-C(CH_3)_2-(CH_2)_2-$ | | O | O | $C_2H_5$ |
| Cl | $CH_3$ | $-CH_2-(CHCH_3)_2-(CH_2)_2-$ | | O | O | $C_2H_5$ |
| Cl | $CH_3$ | $-CH_2-CH-(CH_2)_2-CH-$<br>$CH_2$ | | O | O | $C_2H_5$ |
| Cl | $CH_3$ | $-CH_2-CH$——$CH-CH_2-$<br>$(CH_2)_4$ | | O | O | $C_2H_5$ |
| Cl | $CH_3$ | $-CH_2-CH$——$CH-(CH_2)_2-$<br>$(CH_2)_3$ | | O | O | $C_2H_5$ |
| $CH_3$ | Cl | $-(CH_2)_2-$ | | O | O | $C_2H_5$ |
| $CH_3$ | Cl | $-(CH_2)_4-$ | | O | O | $C_2H_5$ |
| $CH_3$ | Cl | $-(CH_2)_5-$ | | O | O | $C_2H_5$ |
| $CH_3$ | Cl | $-(CH_2)_6-$ | | O | O | $C_2H_5$ |
| $CH_3$ | Cl | $-(CH_2)_7-$ | | O | O | $C_2H_5$ |
| $CH_3$ | Cl | $-(CH_2)_2-O-(CH_2)_2-$ | | O | O | $C_2H_5$ |
| $CH_3$ | Cl | $-(CH_2)_2-S-(CH_2)_2-$ | | O | O | $C_2H_5$ |
| $CH_3$ | Cl | $-CH_2-CHCH_3-(CH_2)_3-$ | | O | O | $C_2H_5$ |
| $CH_3$ | Cl | $-(CH_2)_2-CHCH_3-(CH_2)_2-$ | | O | O | $C_2H_5$ |
| $CH_3$ | Cl | $-(CH_2)_2-CHC_2H_5-(CH_2)_2-$ | | O | O | $C_2H_5$ |
| $CH_3$ | Cl | $-(CH_2)_2-CHC_3H_7-(CH_2)_2-$ | | O | O | $C_2H_5$ |
| $CH_3$ | Cl | $-(CH_2)_2-CHi\text{-}C_3H_7-(CH_2)_2-$ | | O | O | $C_2H_5$ |
| $CH_3$ | Cl | $-(CH_2)_2-CHOCH_3-(CH_2)_2-$ | | O | O | $C_2H_5$ |
| $CH_3$ | Cl | $-(CH_2)_2-CHOC_2H_5-(CH_2)_2-$ | | O | O | $C_2H_5$ |
| $CH_3$ | Cl | $-(CH_2)_2-CHOC_3H_7-(CH_2)_2-$ | | O | O | $C_2H_5$ |
| $CH_3$ | Cl | $-(CH_2)_2-CHi\text{-}OC_3H_7-(CH_2)_2-$ | | O | O | $C_2H_5$ |
| $CH_3$ | Cl | $-(CH_2)_2-C(CH_3)_2-(CH_2)_2-$ | | O | O | $C_2H_5$ |
| $CH_3$ | Cl | $-CH_2-(CHCH_3)_2-(CH_2)_2-$ | | O | O | $C_2H_5$ |
| $CH_3$ | Cl | $-CH_2-CH-(CH_2)_2-CH-$<br>$CH_2$ | | O | O | $C_2H_5$ |
| $CH_3$ | Cl | $-CH_2-CH$——$CH-CH_2-$<br>$(CH_2)_4$ | | O | O | $C_2H_5$ |

TABLE 3-continued

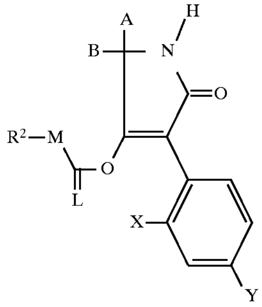
(Ic)

| X | Y | A | B | L | M | $R^2$ |
|---|---|---|---|---|---|---|
| $CH_3$ | Cl | $-CH_2-CH$ ——— $CH-(CH_2)_2-$ <br> $(CH_2)_3$ | | O | O | $C_2H_5$ |
| Cl | $CH_3$ | $CH_3$ | H | O | O | i-$C_3H_7$ |
| Cl | $CH_3$ | $C_2H_5$ | H | O | O | i-$C_3H_7$ |
| Cl | $CH_3$ | $C_3H_7$ | H | O | O | i-$C_3H_7$ |
| Cl | $CH_3$ | i-$C_3H_7$ | H | O | O | i-$C_3H_7$ |
| Cl | $CH_3$ | $C_4H_9$ | H | O | O | i-$C_3H_7$ |
| Cl | $CH_3$ | i-$C_4H_9$ | H | O | O | i-$C_3H_7$ |
| Cl | $CH_3$ | s-$C_4H_9$ | H | O | O | i-$C_3H_7$ |
| Cl | $CH_3$ | t-$C_4H_9$ | H | O | O | i-$C_3H_7$ |
| Cl | $CH_3$ | $CH_3$ | $CH_3$ | O | O | i-$C_3H_7$ |
| Cl | $CH_3$ | $C_2H_5$ | $CH_3$ | O | O | i-$C_3H_7$ |
| Cl | $CH_3$ | $C_3H_7$ | $CH_3$ | O | O | i-$C_3H_7$ |
| Cl | $CH_3$ | i-$C_3H_7$ | $CH_3$ | O | O | i-$C_3H_7$ |
| Cl | $CH_3$ | $C_4H_9$ | $CH_3$ | O | O | i-$C_3H_7$ |
| Cl | $CH_3$ | i-$C_4H_9$ | $CH_3$ | O | O | i-$C_3H_7$ |
| Cl | $CH_3$ | s-$C_4H_9$ | $CH_3$ | O | O | i-$C_3H_7$ |
| Cl | $CH_3$ | t-$C_4H_9$ | $CH_3$ | O | O | i-$C_3H_7$ |
| Cl | $CH_3$ | $C_2H_5$ | $C_2H_5$ | O | O | i-$C_3H_7$ |
| Cl | $CH_3$ | $C_3H_7$ | $C_3H_7$ | O | O | i-$C_3H_7$ |
| Cl | $CH_3$ | 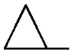 | $CH_3$ | O | O | i-$C_3H_7$ |
| Cl | $CH_3$ | 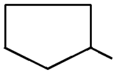 | $CH_3$ | O | O | i-$C_3H_7$ |
| Cl | $CH_3$ | 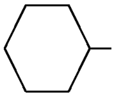 | $CH_3$ | O | O | i-$C_3H_7$ |
| $CH_3$ | Cl | $CH_3$ | H | O | O | i-$C_3H_7$ |
| $CH_3$ | Cl | $C_2H_5$ | H | O | O | i-$C_3H_7$ |
| $CH_3$ | Cl | $C_3H_7$ | H | O | O | i-$C_3H_7$ |
| $CH_3$ | Cl | i-$C_3H_7$ | H | O | O | i-$C_3H_7$ |
| $CH_3$ | Cl | $C_4H_9$ | H | O | O | i-$C_3H_7$ |
| $CH_3$ | Cl | i-$C_4H_9$ | H | O | O | i-$C_3H_7$ |
| $CH_3$ | Cl | s-$C_4H_9$ | H | O | O | i-$C_3H_7$ |
| $CH_3$ | Cl | t-$C_4H_9$ | H | O | O | i-$C_3H_7$ |
| $CH_3$ | Cl | $CH_3$ | $CH_3$ | O | O | i-$C_3H_7$ |
| $CH_3$ | Cl | $C_2H_5$ | $CH_3$ | O | O | i-$C_3H_7$ |
| $CH_3$ | Cl | $C_3H_7$ | $CH_3$ | O | O | i-$C_3H_7$ |
| $CH_3$ | Cl | i-$C_3H_7$ | $CH_3$ | O | O | i-$C_3H_7$ |
| $CH_3$ | Cl | $C_4H_9$ | $CH_3$ | O | O | i-$C_3H_7$ |
| $CH_3$ | Cl | i-$C_4H_9$ | $CH_3$ | O | O | i-$C_3H_7$ |
| $CH_3$ | Cl | s-$C_4H_9$ | $CH_3$ | O | O | i-$C_3H_7$ |
| $CH_3$ | Cl | t-$C_4H_9$ | $CH_3$ | O | O | i-$C_3H_7$ |
| $CH_3$ | Cl | $C_2H_5$ | $C_2H_5$ | O | O | i-$C_3H_7$ |
| $CH_3$ | Cl | $C_3H_7$ | $C_3H_7$ | O | O | i-$C_3H_7$ |
| $CH_3$ | Cl | 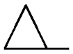 | $CH_3$ | O | O | i-$C_3H_7$ |
| $CH_3$ | Cl | 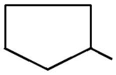 | $CH_3$ | O | O | i-$C_3H_7$ |

TABLE 3-continued

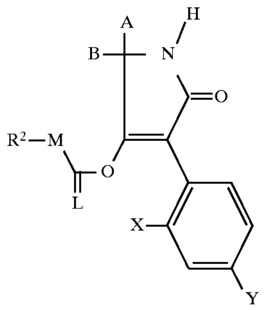

(Ic)

| X | Y | A | B | L | M | $R^2$ |
|---|---|---|---|---|---|---|
| $CH_3$ | Cl | 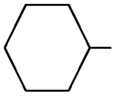 | $CH_3$ | O | O | i-$C_3H_7$ |
| Cl | $CH_3$ | $-(CH_2)_2-$ | | O | O | i-$C_3H_7$ |
| Cl | $CH_3$ | $-(CH_2)_4-$ | | O | O | i-$C_3H_7$ |
| Cl | $CH_3$ | $-(CH_2)_5-$ | | O | O | i-$C_3H_7$ |
| Cl | $CH_3$ | $-(CH_2)_6-$ | | O | O | i-$C_3H_7$ |
| Cl | $CH_3$ | $-(CH_2)_7-$ | | O | O | i-$C_3H_7$ |
| Cl | $CH_3$ | $-(CH_2)_2-O-(CH_2)_2-$ | | O | O | i-$C_3H_7$ |
| Cl | $CH_3$ | $-(CH_2)_2-S-(CH_2)_2-$ | | O | O | i-$C_3H_7$ |
| Cl | $CH_3$ | $-CH_2-CHCH_3-(CH_2)_3-$ | | O | O | i-$C_3H_7$ |
| Cl | $CH_3$ | $-(CH_2)_2-CHCH_3-(CH_2)_2-$ | | O | O | i-$C_3H_7$ |
| Cl | $CH_3$ | $-(CH_2)_2-CHC_2H_5-(CH_2)_2-$ | | O | O | i-$C_3H_7$ |
| Cl | $CH_3$ | $-(CH_2)_2-CHC_3H_7-(CH_2)_2-$ | | O | O | i-$C_3H_7$ |
| Cl | $CH_3$ | $-(CH_2)_2-$CHi-$C_3H_7-(CH_2)_2-$ | | O | O | i-$C_3H_7$ |
| Cl | $CH_3$ | $-(CH_2)_2-CHOCH_3-(CH_2)_2-$ | | O | O | i-$C_3H_7$ |
| Cl | $CH_3$ | $-(CH_2)_2-CHOC_2H_5-(CH_2)_2-$ | | O | O | i-$C_3H_7$ |
| Cl | $CH_3$ | $-(CH_2)_2-CHOC_3H_7-(CH_2)_2-$ | | O | O | i-$C_3H_7$ |
| Cl | $CH_3$ | $-(CH_2)_2-$CHi-$OC_3H_7-(CH_2)_2-$ | | O | O | i-$C_3H_7$ |
| Cl | $CH_3$ | $-(CH_2)_2-C(CH_3)_2-(CH_2)_2-$ | | O | O | i-$C_3H_7$ |
| Cl | $CH_3$ | $-CH_2-(CHCH_3)_2-(CH_2)_2-$ | | O | O | i-$C_3H_7$ |
| Cl | $CH_3$ | 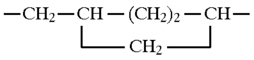 | | O | O | i-$C_3H_7$ |
| Cl | $CH_3$ | 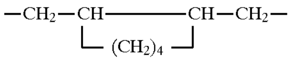 | | O | O | i-$C_3H_7$ |
| Cl | $CH_3$ | 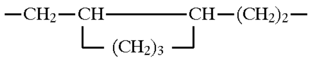 | | O | O | i-$C_3H_7$ |
| $CH_3$ | Cl | $-(CH_2)_2-$ | | O | O | i-$C_3H_7$ |
| $CH_3$ | Cl | $-(CH_2)_4-$ | | O | O | i-$C_3H_7$ |
| $CH_3$ | Cl | $-(CH_2)_5-$ | | O | O | i-$C_3H_7$ |
| $CH_3$ | Cl | $-(CH_2)_6-$ | | O | O | i-$C_3H_7$ |
| $CH_3$ | Cl | $-(CH_2)_7-$ | | O | O | i-$C_3H_7$ |
| $CH_3$ | Cl | $-(CH_2)_2-O-(CH_2)_2-$ | | O | O | i-$C_3H_7$ |
| $CH_3$ | Cl | $-(CH_2)_2-S-(CH_2)_2-$ | | O | O | i-$C_3H_7$ |
| $CH_3$ | Cl | $-CH_2-CHCH_3-(CH_2)_3-$ | | O | O | i-$C_3H_7$ |
| $CH_3$ | Cl | $-(CH_2)_2-CHCH_3-(CH_2)_2-$ | | O | O | i-$C_3H_7$ |
| $CH_3$ | Cl | $-(CH_2)_2-CHC_2H_5-(CH_2)_2-$ | | O | O | i-$C_3H_7$ |
| $CH_3$ | Cl | $-(CH_2)_2-CHC_3H_7-(CH_2)_2-$ | | O | O | i-$C_3H_7$ |
| $CH_3$ | Cl | $-(CH_2)_2-$CHi-$C_3H_7-(CH_2)_2-$ | | O | O | i-$C_3H_7$ |
| $CH_3$ | Cl | $-(CH_2)_2-CHOCH_3-(CH_2)_2-$ | | O | O | i-$C_3H_7$ |
| $CH_3$ | Cl | $-(CH_2)_2-CHOC_2H_5-(CH_2)_2-$ | | O | O | i-$C_3H_7$ |
| $CH_3$ | Cl | $-(CH_2)_2-CHOC_3H_7-(CH_2)_2-$ | | O | O | i-$C_3H_7$ |
| $CH_3$ | Cl | $(CH_2)_2-$CHi-$OC_3H_7-(CH_2)_2-$ | | O | O | i-$C_3H_7$ |
| $CH_3$ | Cl | $-(CH_2)_2-C(CH_3)_2-(CH_2)_2-$ | | O | O | i-$C_3H_7$ |
| $CH_3$ | Cl | $-CH_2-(CHCH_3)_2-(CH_2)_2-$ | | O | O | i-$C_3H_7$ |
| $CH_3$ | Cl | 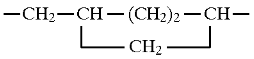 | | O | O | i-$C_3H_7$ |
| $CH_3$ | Cl | 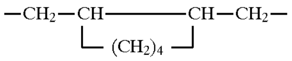 | | O | O | i-$C_3H_7$ |

TABLE 3-continued (Ic)

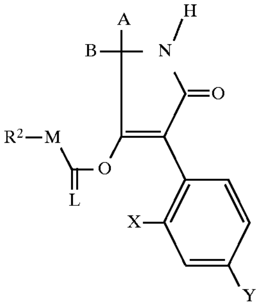

| X | Y | A | B | L | M | $R^2$ |
|---|---|---|---|---|---|---|
| $CH_3$ | Cl | 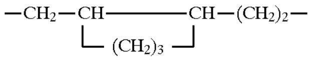 | | O | O | i-$C_3H_7$ |
| Cl | $CH_3$ | $CH_3$ | H | O | S | i-$C_3H_7$ |
| Cl | $CH_3$ | $C_2H_5$ | H | O | S | i-$C_3H_7$ |
| Cl | $CH_3$ | $C_3H_7$ | H | O | S | i-$C_3H_7$ |
| Cl | $CH_3$ | i-$C_3H_7$ | H | O | S | i-$C_3H_7$ |
| Cl | $CH_3$ | $C_4H_9$ | H | O | S | i-$C_3H_7$ |
| Cl | $CH_3$ | i-$C_4H_9$ | H | O | S | i-$C_3H_7$ |
| Cl | $CH_3$ | s-$C_4H_9$ | H | O | S | i-$C_3H_7$ |
| Cl | $CH_3$ | t-$C_4H_9$ | H | O | S | i-$C_3H_7$ |
| Cl | $CH_3$ | $CH_3$ | $CH_3$ | O | S | i-$C_3H_7$ |
| Cl | $CH_3$ | $C_2H_5$ | $CH_3$ | O | S | i-$C_3H_7$ |
| Cl | $CH_3$ | $C_3H_7$ | $CH_3$ | O | S | i-$C_3H_7$ |
| Cl | $CH_3$ | i-$C_3H_7$ | $CH_3$ | O | S | i-$C_3H_7$ |
| Cl | $CH_3$ | $C_4H_9$ | $CH_3$ | O | S | i-$C_3H_7$ |
| Cl | $CH_3$ | i-$C_4H_9$ | $CH_3$ | O | S | i-$C_3H_7$ |
| Cl | $CH_3$ | s-$C_4H_9$ | $CH_3$ | O | S | i-$C_3H_7$ |
| Cl | $CH_3$ | t-$C_4H_9$ | $CH_3$ | O | S | i-$C_3H_7$ |
| Cl | $CH_3$ | $C_2H_5$ | $C_2H_5$ | O | S | i-$C_3H_7$ |
| Cl | $CH_3$ | $C_3H_7$ | $C_3H_7$ | O | S | i-$C_3H_7$ |
| Cl | $CH_3$ | 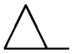 | $CH_3$ | O | S | i-$C_3H_7$ |
| Cl | $CH_3$ | 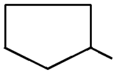 | $CH_3$ | O | S | i-$C_3H_7$ |
| Cl | $CH_3$ | 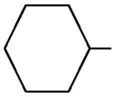 | $CH_3$ | O | S | i-$C_3H_7$ |
| $CH_3$ | Cl | $CH_3$ | H | O | S | i-$C_3H_7$ |
| $CH_3$ | Cl | $C_2H_5$ | H | O | S | i-$C_3H_7$ |
| $CH_3$ | Cl | $C_3H_7$ | H | O | S | i-$C_3H_7$ |
| $CH_3$ | Cl | i-$C_3H_7$ | H | O | S | i-$C_3H_7$ |
| $CH_3$ | Cl | $C_4H_9$ | H | O | S | i-$C_3H_7$ |
| $CH_3$ | Cl | i-$C_4H_9$ | H | O | S | i-$C_3H_7$ |
| $CH_3$ | Cl | s-$C_4H_9$ | H | O | S | i-$C_3H_7$ |
| $CH_3$ | Cl | t-$C_4H_9$ | H | O | S | i-$C_3H_7$ |
| $CH_3$ | Cl | $CH_3$ | $CH_3$ | O | S | i-$C_3H_7$ |
| $CH_3$ | Cl | $C_2H_5$ | $CH_3$ | O | S | i-$C_3H_7$ |
| $CH_3$ | Cl | $C_3H_7$ | $CH_3$ | O | S | i-$C_3H_7$ |
| $CH_3$ | Cl | i-$C_3H_7$ | $CH_3$ | O | S | i-$C_3H_7$ |
| $CH_3$ | Cl | $C_4H_9$ | $CH_3$ | O | S | i-$C_3H_7$ |
| $CH_3$ | Cl | i-$C_4H_9$ | $CH_3$ | O | s | i-$C_3H_7$ |
| $CH_3$ | Cl | s-$C_4H_9$ | $CH_3$ | O | S | i-$C_3H_7$ |
| $CH_3$ | Cl | t-$C_4H_9$ | $CH_3$ | O | S | i-$C_3H_7$ |
| $CH_3$ | Cl | $C_2H_5$ | $C_2H_5$ | O | S | i-$C_3H_7$ |
| $CH_3$ | Cl | $C_3H_7$ | $C_3H_7$ | O | S | i-$C_3H_7$ |
| $CH_3$ | Cl | 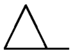 | $CH_3$ | O | S | i-$C_3H_7$ |
| $CH_3$ | Cl | 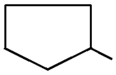 | $CH_3$ | O | S | i-$C_3H_7$ |

TABLE 3-continued

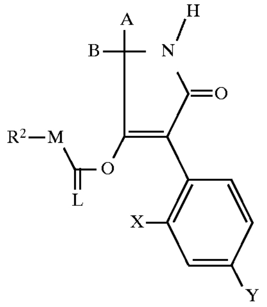

(Ic)

| X | Y | A | B | L | M | $R^2$ |
| --- | --- | --- | --- | --- | --- | --- |
| $CH_3$ | Cl | 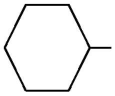 | $CH_3$ | O | S | i-$C_3H_7$ |
| Cl | $CH_3$ | | $-(CH_2)_2-$ | O | S | i-$C_3H_7$ |
| Cl | $CH_3$ | | $-(CH_2)_4-$ | O | S | i-$C_3H_7$ |
| Cl | $CH_3$ | | $-(CH_2)_5-$ | O | S | i-$C_3H_7$ |
| Cl | $CH_3$ | | $-(CH_2)_6-$ | O | S | i-$C_3H_7$ |
| Cl | $CH_3$ | | $-(CH_2)_7-$ | O | S | i-$C_3H_7$ |
| Cl | $CH_3$ | | $-(CH_2)_2-O-(CH_2)_2-$ | O | S | i-$C_3H_7$ |
| Cl | $CH_3$ | | $-(CH_2)_2-S-(CH_2)_2-$ | O | S | i-$C_3H_7$ |
| Cl | $CH_3$ | | $-CH_2-CHCH_3-(CH_2)_3-$ | O | S | i-$C_3H_7$ |
| Cl | $CH_3$ | | $-(CH_2)_2-CHCH_3-(CH_2)_2-$ | O | S | i-$C_3H_7$ |
| Cl | $CH_3$ | | $-(CH_2)_2-CHC_2H_5-(CH_2)_2-$ | O | S | i-$C_3H_7$ |
| Cl | $CH_3$ | | $-(CH_2)_2-CHC_3H_7-(CH_2)_2-$ | O | S | i-$C_3H_7$ |
| Cl | $CH_3$ | | $-(CH_2)_2-CHi\text{-}C_3H_7-(CH_2)_2-$ | O | S | i-$C_3H_7$ |
| Cl | $CH_3$ | | $-(CH_2)_2-CHOCH_3-(CH_2)_2-$ | O | S | i-$C_3H_7$ |
| Cl | $CH_3$ | | $-(CH_2)_2-CHOC_2H_5-(CH_2)_2-$ | O | S | i-$C_3H_7$ |
| Cl | $CH_3$ | | $-(CH_2)_2-CHOC_3H_7-(CH_2)_2-$ | O | S | i-$C_3H_7$ |
| Cl | $CH_3$ | | $-(CH_2)_2-CHi\text{-}OC_3H_7-(CH_2)_2-$ | O | S | i-$C_3H_7$ |
| Cl | $CH_3$ | | $-(CH_2)_2-C(CH_3)_2-(CH_2)_2-$ | O | S | i-$C_3H_7$ |
| Cl | $CH_3$ | | $-CH_2-(CHCH_3)_2-(CH_2)_2-$ | O | S | i-$C_3H_7$ |
| Cl | $CH_3$ | | 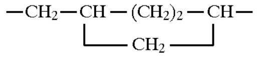 | O | S | i-$C_3H_7$ |
| Cl | $CH_3$ | | 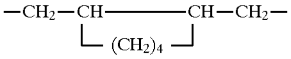 | O | S | i-$C_3H_7$ |
| Cl | $CH_3$ | | 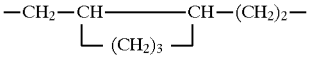 | O | S | i-$C_3H_7$ |
| $CH_3$ | Cl | | $-(CH_2)_2-$ | O | S | i-$C_3H_7$ |
| $CH_3$ | Cl | | $-(CH_2)_4-$ | O | S | i-$C_3H_7$ |
| $CH_3$ | Cl | | $-(CH_2)_5-$ | O | S | i-$C_3H_7$ |
| $CH_3$ | Cl | | $-(CH_2)_6-$ | O | S | i-$C_3H_7$ |
| $CH_3$ | Cl | | $-(CH_2)_7-$ | O | S | i-$C_3H_7$ |
| $CH_3$ | Cl | | $-(CH_2)_2-O-(CH_2)_2-$ | O | S | i-$C_3H_7$ |
| $CH_3$ | Cl | | $-(CH_2)_2-S-(CH_2)_2-$ | O | S | i-$C_3H_7$ |
| $CH_3$ | Cl | | $-CH_2-CHCH_3-(CH_2)_3-$ | O | S | i-$C_3H_7$ |
| $CH_3$ | Cl | | $-(CH_2)_2-CHCH_3-(CH_2)_2-$ | O | S | i-$C_3H_7$ |
| $CH_3$ | Cl | | $-(CH_2)_2-CHC_2H_5-(CH_2)_2-$ | O | S | i-$C_3H_7$ |
| $CH_3$ | Cl | | $-(CH_2)_2-CHC_3H_7-(CH_2)_2-$ | O | S | i-$C_3H_7$ |
| $CH_3$ | Cl | | $-(CH_2)_2-CHi\text{-}C_3H_7-(CH_2)_2-$ | O | S | i-$C_3H_7$ |
| $CH_3$ | Cl | | $-(CH_2)_2-CHOCH_3-(CH_2)_2-$ | O | S | i-$C_3H_7$ |
| $CH_3$ | Cl | | $-(CH_2)_2-CHOC_2H_5-(CH_2)_2-$ | O | S | i-$C_3H_7$ |
| $CH_3$ | Cl | | $-(CH_2)_2-CHOC_3H_7-(CH_2)_2-$ | O | S | i-$C_3H_7$ |
| $CH_3$ | Cl | | $-(CH_2)_2-CHi\text{-}OC_3H_7-(CH_2)_2-$ | O | S | i-$C_3H_7$ |
| $CH_3$ | Cl | | $-(CH_2)_2-C(CH_3)_2-(CH_2)_2-$ | O | S | i-$C_3H_7$ |
| $CH_3$ | Cl | | $-CH_2-(CHCH_3)_2-(CH_2)_2-$ | O | S | i-$C_3H_7$ |
| $CH_3$ | Cl | | 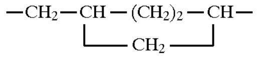 | O | S | i-$C_3H_7$ |
| $CH_3$ | Cl | | 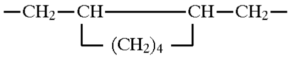 | O | S | i-$C_3H_7$ |

TABLE 3-continued

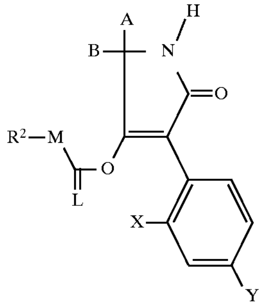

(Ic)

| X | Y | A | B | L | M | $R^2$ |
|---|---|---|---|---|---|---|
| $CH_3$ | Cl | $-CH_2-CH-CH-(CH_2)_2-$<br>$(CH_2)_3$ | | O | S | i-$C_3H_7$ |
| Cl | $CH_3$ | $CH_3$ | H | O | O | s-$C_4H_9$ |
| Cl | $CH_3$ | $C_2H_5$ | H | O | O | s-$C_4H_9$ |
| Cl | $CH_3$ | $C_3H_7$ | H | O | O | s-$C_4H_9$ |
| Cl | $CH_3$ | i-$C_3H_7$ | H | O | O | s-$C_4H_9$ |
| Cl | $CH_3$ | $C_4H_9$ | H | O | O | s-$C_4H_9$ |
| Cl | $CH_3$ | i-$C_4H_9$ | H | O | O | s-$C_4H_9$ |
| Cl | $CH_3$ | s-$C_4H_9$ | H | O | O | s-$C_4H_9$ |
| Cl | $CH_3$ | t-$C_4H_9$ | H | O | O | s-$C_4H_9$ |
| Cl | $CH_3$ | $CH_3$ | $CH_3$ | O | O | s-$C_4H_9$ |
| Cl | $CH_3$ | $C_2H_5$ | $CH_3$ | O | O | s-$C_4H_9$ |
| Cl | $CH_3$ | $C_3H_7$ | $CH_3$ | O | O | s-$C_4H_9$ |
| Cl | $CH_3$ | i-$C_3H_7$ | $CH_3$ | O | O | s-$C_4H_9$ |
| Cl | $CH_3$ | $C_4H_9$ | $CH_3$ | O | O | s-$C_4H_9$ |
| Cl | $CH_3$ | i-$C_4H_9$ | $CH_3$ | O | O | s-$C_4H_9$ |
| Cl | $CH_3$ | s-$C_4H_9$ | $CH_3$ | O | O | s-$C_4H_9$ |
| Cl | $CH_3$ | t-$C_4H_9$ | $CH_3$ | O | O | s-$C_4H_9$ |
| Cl | $CH_3$ | $C_2H_5$ | $C_2H_5$ | O | O | s-$C_4H_9$ |
| Cl | $CH_3$ | $C_3H_7$ | $C_3H_7$ | O | O | s-$C_4H_9$ |
| Cl | $CH_3$ | 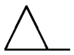 | $CH_3$ | O | O | s-$C_4H_9$ |
| Cl | $CH_3$ | 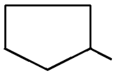 | $CH_3$ | O | O | s-$C_4H_9$ |
| Cl | $CH_3$ | 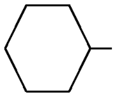 | $CH_3$ | O | O | s-$C_4H_9$ |
| $CH_3$ | Cl | $CH_3$ | H | O | O | s-$C_4H_9$ |
| $CH_3$ | Cl | $C_2H_5$ | H | O | O | s-$C_4H_9$ |
| $CH_3$ | Cl | $C_3H_7$ | H | O | O | s-$C_4H_9$ |
| $CH_3$ | Cl | i-$C_3H_7$ | H | O | O | s-$C_4H_9$ |
| $CH_3$ | Cl | $C_4H_9$ | H | O | O | s-$C_4H_9$ |
| $CH_3$ | Cl | i-$C_4H_9$ | H | O | O | s-$C_4H_9$ |
| $CH_3$ | Cl | s-$C_4H_9$ | H | O | O | s-$C_4H_9$ |
| $CH_3$ | Cl | t-$C_4H_9$ | H | O | O | s-$C_4H_9$ |
| $CH_3$ | Cl | $CH_3$ | $CH_3$ | O | O | s-$C_4H_9$ |
| $CH_3$ | Cl | $C_2H_5$ | $CH_3$ | O | O | s-$C_4H_9$ |
| $CH_3$ | Cl | $C_3H_7$ | $CH_3$ | O | O | s-$C_4H_9$ |
| $CH_3$ | Cl | i-$C_3H_7$ | $CH_3$ | O | O | s-$C_4H_9$ |
| $CH_3$ | Cl | $C_4H_9$ | $CH_3$ | O | O | s-$C_4H_9$ |
| $CH_3$ | Cl | i-$C_4H_9$ | $CH_3$ | O | O | s-$C_4H_9$ |
| $CH_3$ | Cl | s-$C_4H_9$ | $CH_3$ | O | O | s-$C_4H_9$ |
| $CH_3$ | Cl | t-$C_4H_9$ | $CH_3$ | O | O | s-$C_4H_9$ |
| $CH_3$ | Cl | $C_2H_5$ | $C_2H_5$ | O | O | s-$C_4H_9$ |
| $CH_3$ | Cl | $C_3H_7$ | $C_3H_7$ | O | O | s-$C_4H_9$ |
| $CH_3$ | Cl | 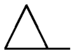 | $CH_3$ | O | O | s-$C_4H_9$ |
| $CH_3$ | Cl | 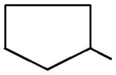 | $CH_3$ | O | O | s-$C_4H_9$ |

TABLE 3-continued

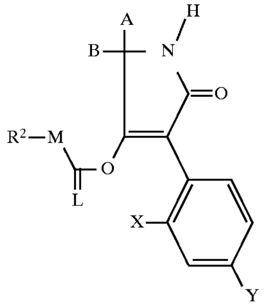

(Ic)

| X | Y | A | B | L | M | $R^2$ |
|---|---|---|---|---|---|---|
| $CH_3$ | Cl | 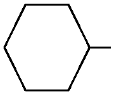 | $CH_3$ | O | O | s-$C_4H_9$ |
| Cl | $CH_3$ | $-(CH_2)_2-$ | | O | O | s-$C_4H_9$ |
| Cl | $CH_3$ | $-(CH_2)_4-$ | | O | O | s-$C_4H_9$ |
| Cl | $CH_3$ | $-(CH_2)_5-$ | | O | O | s-$C_4H_9$ |
| Cl | $CH_3$ | $-(CH_2)_6-$ | | O | O | s-$C_4H_9$ |
| Cl | $CH_3$ | $-(CH_2)_7-$ | | O | O | s-$C_4H_9$ |
| Cl | $CH_3$ | $-(CH_2)_2-O-(CH_2)_2-$ | | O | O | s-$C_4H_9$ |
| Cl | $CH_3$ | $-(CH_2)_2-S-(CH_2)_2-$ | | O | O | s-$C_4H_9$ |
| Cl | $CH_3$ | $-CH_2-CHCH_3-(CH_2)_3-$ | | O | O | s-$C_4H_9$ |
| Cl | $CH_3$ | $-(CH_2)_2-CHCH_3-(CH_2)_2-$ | | O | O | s-$C_4H_9$ |
| Cl | $CH_3$ | $-(CH_2)_2-CHC_2H_5-(CH_2)_2-$ | | O | O | s-$C_4H_9$ |
| Cl | $CH_3$ | $-(CH_2)_2-CHC_3H_7-(CH_2)_2-$ | | O | O | s-$C_4H_9$ |
| Cl | $CH_3$ | $-(CH_2)_2-CHi\text{-}C_3H_7-(CH_2)_2-$ | | O | O | s-$C_4H_9$ |
| Cl | $CH_3$ | $-(CH_2)_2-CHOCH_3-(CH_2)_2-$ | | O | O | s-$C_4H_9$ |
| Cl | $CH_3$ | $-(CH_2)_2-CHOC_2H_5-(CH_2)_2-$ | | O | O | s-$C_4H_9$ |
| Cl | $CH_3$ | $-(CH_2)_2-CHOC_3H_7-(CH_2)_2-$ | | O | O | s-$C_4H_9$ |
| Cl | $CH_3$ | $-(CH_2)_2-CHi\text{-}OC_3H_7-(CH_2)_2-$ | | O | O | s-$C_4H_9$ |
| Cl | $CH_3$ | $-(CH_2)_2-C(CH_3)_2-(CH_2)_2-$ | | O | O | s-$C_4H_9$ |
| Cl | $CH_3$ | $-CH_2-(CHCH_3)_2-(CH_2)_2-$ | | O | O | s-$C_4H_9$ |
| Cl | $CH_3$ | 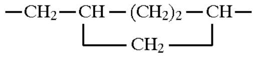 | | O | O | s-$C_4H_9$ |
| Cl | $CH_3$ | 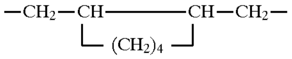 | | O | O | s-$C_4H_9$ |
| Cl | $CH_3$ | 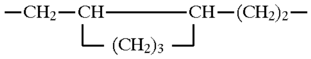 | | O | O | s-$C_4H_9$ |
| $CH_3$ | Cl | $-(CH_2)_2-$ | | O | O | s-$C_4H_9$ |
| $CH_3$ | Cl | $-(CH_2)_4-$ | | O | O | s-$C_4H_9$ |
| $CH_3$ | Cl | $-(CH_2)_5-$ | | O | O | s-$C_4H_9$ |
| $CH_3$ | Cl | $-(CH_2)_6-$ | | O | O | s-$C_4H_9$ |
| $CH_3$ | Cl | $-(CH_2)_7-$ | | O | O | s-$C_4H_9$ |
| $CH_3$ | Cl | $-(CH_2)_2-O-(CH_2)_2-$ | | O | O | s-$C_4H_9$ |
| $CH_3$ | Cl | $-(CH_2)_2-S-(CH_2)_2-$ | | O | O | s-$C_4H_9$ |
| $CH_3$ | Cl | $-CH_2-CHCH_3-(CH_2)_3-$ | | O | O | s-$C_4H_9$ |
| $CH_3$ | Cl | $-(CH_2)_2-CHCH_3-(CH_2)_2-$ | | O | O | s-$C_4H_9$ |
| $CH_3$ | Cl | $-(CH_2)_2-CHC_2H_5-(CH_2)_2-$ | | O | O | s-$C_4H_9$ |
| $CH_3$ | Cl | $-(CH_2)_2-CHC_3H_7-(CH_2)_2-$ | | O | O | s-$C_4H_9$ |
| $CH_3$ | Cl | $-(CH_2)_2-CHi\text{-}C_3H_7-(CH_2)_2-$ | | O | O | s-$C_4H_9$ |
| $CH_3$ | Cl | $-(CH_2)_2-CHOCH_3-(CH_2)_2-$ | | O | O | s-$C_4H_9$ |
| $CH_3$ | Cl | $-(CH_2)_2-CHOC_2H_5-(CH_2)_2-$ | | O | O | s-$C_4H_9$ |
| $CH_3$ | Cl | $-(CH_2)_2-CHOC_3H_7-(CH_2)_2-$ | | O | O | s-$C_4H_9$ |
| $CH_3$ | Cl | $-(CH_2)_2-CHi\text{-}OC_3H_7-(CH_2)_2-$ | | O | O | s-$C_4H_9$ |
| $CH_3$ | Cl | $-(CH_2)_2-C(CH_3)_2-(CH_2)_2-$ | | O | O | s-$C_4H_9$ |
| $CH_3$ | Cl | $-CH_2-(CHCH_3)_2-(CH_2)_2-$ | | O | O | s-$C_4H_9$ |
| $CH_3$ | Cl | 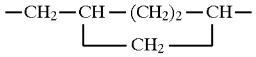 | | O | O | s-$C_4H_9$ |
| $CH_3$ | Cl | 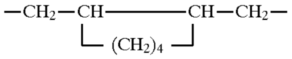 | | O | O | s-$C_4H_9$ |

TABLE 3-continued

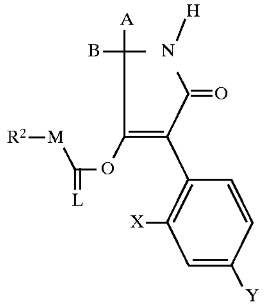

(Ic)

| X | Y | A | B | L | M | $R^2$ |
|---|---|---|---|---|---|---|
| $CH_3$ | Cl | $-CH_2-CH-CH-(CH_2)_2-$ with $(CH_2)_3$ bridge | | O | O | $s-C_4H_9$ |

The following compounds of the formula (Id) may be mentioned individually in addition to the compounds mentioned in the preparation examples:

TABLE 4

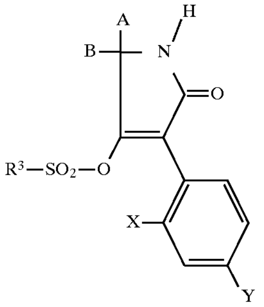

(Id)

| X | Y | A | B | $R^3$ |
|---|---|---|---|---|
| Cl | $CH_3$ | $CH_3$ | H | $CH_3$ |
| Cl | $CH_3$ | $C_2H_5$ | H | $CH_3$ |
| Cl | $CH_3$ | $C_3H_7$ | H | $CH_3$ |
| Cl | $CH_3$ | $i-C_3H_7$ | H | $CH_3$ |
| Cl | $CH_3$ | $C_4H_9$ | H | $CH_3$ |
| Cl | $CH_3$ | $i-C_4H_9$ | H | $CH_3$ |
| Cl | $CH_3$ | $s-C_4H_9$ | H | $CH_3$ |
| Cl | $CH_3$ | $t-C_4H_9$ | H | $CH_3$ |
| Cl | $CH_3$ | $CH_3$ | $CH_3$ | $CH_3$ |
| Cl | $CH_3$ | $C_2H_5$ | $CH_3$ | $CH_3$ |
| Cl | $CH_3$ | $C_3H_7$ | $CH_3$ | $CH_3$ |
| Cl | $CH_3$ | $i-C_3H_7$ | $CH_3$ | $CH_3$ |
| Cl | $CH_3$ | $C_4H_9$ | $CH_3$ | $CH_3$ |
| Cl | $CH_3$ | $i-C_4H_9$ | $CH_3$ | $CH_3$ |
| Cl | $CH_3$ | $s-C_4H_9$ | $CH_3$ | $CH_3$ |
| Cl | $CH_3$ | $t-C_4H_9$ | $CH_3$ | $CH_3$ |
| Cl | $CH_3$ | $C_2H_5$ | $C_2H_5$ | $CH_3$ |
| Cl | $CH_3$ | $C_3H_7$ | $C_3H_7$ | $CH_3$ |
| Cl | $CH_3$ | 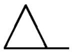 | $CH_3$ | $CH_3$ |
| Cl | $CH_3$ | 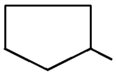 | $CH_3$ | $CH_3$ |
| Cl | $CH_3$ | 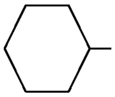 | $CH_3$ | $CH_3$ |

TABLE 4-continued

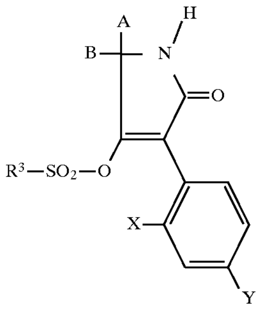

(Id)

| X | Y | A | B | $R^3$ |
|---|---|---|---|---|
| $CH_3$ | Cl | $CH_3$ | H | $CH_3$ |
| $CH_3$ | Cl | $C_2H_5$ | H | $CH_3$ |
| $CH_3$ | Cl | $C_3H_7$ | H | $CH_3$ |
| $CH_3$ | Cl | $i-C_3H_7$ | H | $CH_3$ |
| $CH_3$ | Cl | $C_4H_9$ | H | $CH_3$ |
| $CH_3$ | Cl | $i-C_4H_9$ | H | $CH_3$ |
| $CH_3$ | Cl | $s-C_4H_9$ | H | $CH_3$ |
| $CH_3$ | Cl | $t-C_4H_9$ | H | $CH_3$ |
| $CH_3$ | Cl | $CH_3$ | $CH_3$ | $CH_3$ |
| $CH_3$ | Cl | $C_2H_5$ | $CH_3$ | $CH_3$ |
| $CH_3$ | Cl | $C_3H_7$ | $CH_3$ | $CH_3$ |
| $CH_3$ | Cl | $i-C_3H_7$ | $CH_3$ | $CH_3$ |
| $CH_3$ | Cl | $C_4H_9$ | $CH_3$ | $CH_3$ |
| $CH_3$ | Cl | $i-C_4H_9$ | $CH_3$ | $CH_3$ |
| $CH_3$ | Cl | $s-C_4H_9$ | $CH_3$ | $CH_3$ |
| $CH_3$ | Cl | $t-C_4H_9$ | $CH_3$ | $CH_3$ |
| $CH_3$ | Cl | $C_2H_5$ | $C_2H_5$ | $CH_3$ |
| $CH_3$ | Cl | $C_3H_7$ | $C_3H_7$ | $CH_3$ |
| $CH_3$ | Cl | 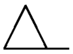 | $CH_3$ | $CH_3$ |
| $CH_3$ | Cl | 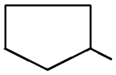 | $CH_3$ | $CH_3$ |
| $CH_3$ | Cl | 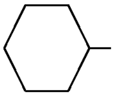 | $CH_3$ | $CH_3$ |
| Cl | $CH_3$ | $-(CH_2)_2-$ | | $CH_3$ |
| Cl | $CH_3$ | $-(CH_2)_4-$ | | $CH_3$ |
| Cl | $CH_3$ | $-(CH_2)_5-$ | | $CH_3$ |
| Cl | $CH_3$ | $-(CH_2)_6-$ | | $CH_3$ |

TABLE 4-continued

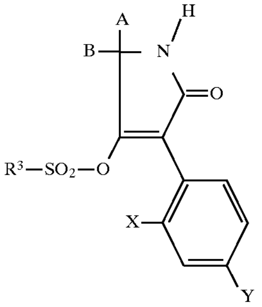

(Id)

| X | Y | A | B | $R^3$ |
|---|---|---|---|---|
| Cl | $CH_3$ | | $-(CH_2)_7-$ | $CH_3$ |
| Cl | $CH_3$ | | $-(CH_2)_2-O-(CH_2)_2-$ | $CH_3$ |
| Cl | $CH_3$ | | $-(CH_2)_2-S-(CH_2)_2-$ | $CH_3$ |
| Cl | $CH_3$ | | $-CH_2-CHCH_3-(CH_2)_3-$ | $CH_3$ |
| Cl | $CH_3$ | | $-(CH_2)_2-CHCH_3-(CH_2)_2-$ | $CH_3$ |
| Cl | $CH_3$ | | $-(CH_2)_2-CHC_2H_5-(CH_2)_2-$ | $CH_3$ |
| Cl | $CH_3$ | | $-(CH_2)_2-CHC_3H_7-(CH_2)_2-$ | $CH_3$ |
| Cl | $CH_3$ | | $-(CH_2)_2-CHi\text{-}C_3H_7-(CH_2)_2-$ | $CH_3$ |
| Cl | $CH_3$ | | $-(CH_2)_2-CHOCH_3-(CH_2)_2-$ | $CH_3$ |
| Cl | $CH_3$ | | $-(CH_2)_2-CHOC_2H_5-(CH_2)_2-$ | $CH_3$ |
| Cl | $CH_3$ | | $-(CH_2)_2-CHOC_3H_7-(CH_2)_2-$ | $CH_3$ |
| Cl | $CH_3$ | | $-(CH_2)_2-CHi\text{-}OC_3H_7-(CH_2)_2-$ | $CH_3$ |
| Cl | $CH_3$ | | $-(CH_2)_2-C(CH_3)_2-(CH_2)_2-$ | $CH_3$ |
| Cl | $CH_3$ | | $-CH_2-(CHCH_3)_2-(CH_2)_2-$ | $CH_3$ |
| Cl | $CH_3$ | | 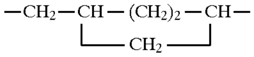 | $CH_3$ |
| Cl | $CH_3$ | | 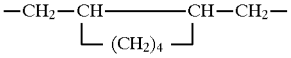 | $CH_3$ |
| Cl | $CH_3$ | | 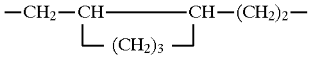 | $CH_3$ |
| $CH_3$ | Cl | | $-(CH_2)_2-$ | $CH_3$ |
| $CH_3$ | Cl | | $-(CH_2)_4-$ | $CH_3$ |
| $CH_3$ | Cl | | $-(CH_2)_5-$ | $CH_3$ |
| $CH_3$ | Cl | | $-(CH_2)_6-$ | $CH_3$ |
| $CH_3$ | Cl | | $-(CH_2)_7-$ | $CH_3$ |

TABLE 4-continued

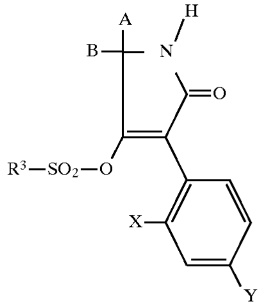

(Id)

| X | Y | A | B | $R^3$ |
|---|---|---|---|---|
| $CH_3$ | Cl | | $-(CH_2)_2-O-(CH_2)_2-$ | $CH_3$ |
| $CH_3$ | Cl | | $-(CH_2)_2-S-(CH_2)_2-$ | $CH_3$ |
| $CH_3$ | Cl | | $-CH_2-CHCH_3-(CH_2)_3-$ | $CH_3$ |
| $CH_3$ | Cl | | $-(CH_2)_2-CHCH_3-(CH_2)_2-$ | $CH_3$ |
| $CH_3$ | Cl | | $-(CH_2)_2-CHC_2H_5-(CH_2)_2-$ | $CH_3$ |
| $CH_3$ | Cl | | $-(CH_2)_2-CHC_3H_7-(CH_2)_2-$ | $CH_3$ |
| $CH_3$ | Cl | | $-(CH_2)_2-CHi\text{-}C_3H_7-(CH_2)_2-$ | $CH_3$ |
| $CH_3$ | Cl | | $-(CH_2)_2-CHOCH_3-(CH_2)_2-$ | $CH_3$ |
| $CH_3$ | Cl | | $-(CH_2)_2-CHOC_2H_5-(CH_2)_2-$ | $CH_3$ |
| $CH_3$ | Cl | | $-(CH_2)_2-CHOC_3H_7-(CH_2)_2-$ | $CH_3$ |
| $CH_3$ | Cl | | $-(CH_2)_2-CHi\text{-}OC_3H_7-(CH_2)_2-$ | $CH_3$ |
| $CH_3$ | Cl | | $-(CH_2)_2-C(CH_3)_2-(CH_2)_2-$ | $CH_3$ |
| $CH_3$ | Cl | | $-CH_2-(CHCH_3)_2-(CH_2)_2-$ | $CH_3$ |
| $CH_3$ | Cl | | 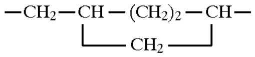 | $CH_3$ |
| $CH_3$ | Cl | | 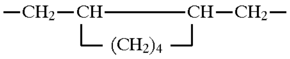 | $CH_3$ |
| $CH_3$ | Cl | | 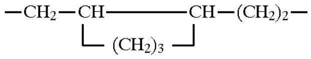 | $CH_3$ |

The following compounds of the formula (Ie) may be mentioned individually in addition to the compounds mentioned in the preparation examples:

TABLE 5

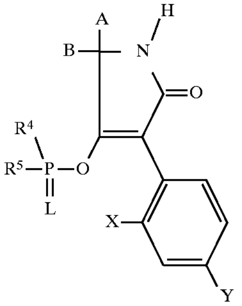

(Ie)

| X | Y | A | B | L | $R^4$ | $R^5$ |
|---|---|---|---|---|---|---|
| Cl | $CH_3$ | $CH_3$ | H | S | $CH_3$ | $i\text{-}C_3H_7-S-$ |
| Cl | $CH_3$ | $C_2H_5$ | H | S | $CH_3$ | $i\text{-}C_3H_7-S-$ |
| Cl | $CH_3$ | $C_3H_7$ | H | S | $CH_3$ | $i\text{-}C_3H_7-S-$ |
| Cl | $CH_3$ | $i\text{-}C_3H_7$ | H | S | $CH_3$ | $i\text{-}C_3H_7-S-$ |
| Cl | $CH_3$ | $C_4H_9$ | H | S | $CH_3$ | $i\text{-}C_3H_7-S-$ |
| Cl | $CH_3$ | $i\text{-}C_4H_9$ | H | S | $CH_3$ | $i\text{-}C_3H_7-S-$ |
| Cl | $CH_3$ | $s\text{-}C_4H_9$ | H | S | $CH_3$ | $i\text{-}C_3H_7-S-$ |
| Cl | $CH_3$ | $t\text{-}C_4H_9$ | H | S | $CH_3$ | $i\text{-}C_3H_7-S-$ |

TABLE 5-continued

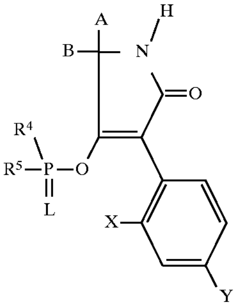

(Ie)

| X | Y | A | B | L | $R^4$ | $R^5$ |
|---|---|---|---|---|---|---|
| Cl | $CH_3$ | $CH_3$ | $CH_3$ | S | $CH_3$ | $i-C_3H_7-S-$ |
| Cl | $CH_3$ | $C_2H_5$ | $CH_3$ | S | $CH_3$ | $i-C_3H_7-S-$ |
| Cl | $CH_3$ | $C_3H_7$ | $CH_3$ | S | $CH_3$ | $i-C_3H_7-S-$ |
| Cl | $CH_3$ | $i-C_3H_7$ | $CH_3$ | S | $CH_3$ | $i-C_3H_7-S-$ |
| Cl | $CH_3$ | $C_4H_9$ | $CH_3$ | S | $CH_3$ | $i-C_3H_7-S-$ |
| Cl | $CH_3$ | $i-C_4H_9$ | $CH_3$ | S | $CH_3$ | $i-C_3H_7-S-$ |
| Cl | $CH_3$ | $s-C_4H_9$ | $CH_3$ | S | $CH_3$ | $i-C_3H_7-S-$ |
| Cl | $CH_3$ | $t-C_4H_9$ | $CH_3$ | S | $CH_3$ | $i-C_3H_7-S-$ |
| Cl | $CH_3$ | $C_2H_5$ | $C_2H_5$ | S | $CH_3$ | $i-C_3H_7-S-$ |
| Cl | $CH_3$ | $C_3H_7$ | $C_3H_7$ | S | $CH_3$ | $i-C_3H_7-S-$ |
| Cl | $CH_3$ | 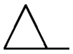 | $CH_3$ | S | $CH_3$ | $i-C_3H_7-S-$ |
| Cl | $CH_3$ | 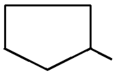 | $CH_3$ | S | $CH_3$ | $i-C_3H_7-S-$ |
| Cl | $CH_3$ | 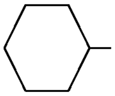 | $CH_3$ | S | $CH_3$ | $i-C_3H_7-S-$ |
| $CH_3$ | Cl | $CH_3$ | H | S | $CH_3$ | $i-C_3H_7-S-$ |
| $CH_3$ | Cl | $C_2H_5$ | H | S | $CH_3$ | $i-C_3H_7-S-$ |
| $CH_3$ | Cl | $C_3H_7$ | H | S | $CH_3$ | $i-C_3H_7-S-$ |
| $CH_3$ | Cl | $i-C_3H_7$ | H | S | $CH_3$ | $i-C_3H_7-S-$ |
| $CH_3$ | Cl | $C_4H_9$ | H | S | $CH_3$ | $i-C_3H_7-S-$ |
| $CH_3$ | Cl | $i-C_4H_9$ | H | S | $CH_3$ | $i-C_3H_7-S-$ |
| $CH_3$ | Cl | $s-C_4H_9$ | H | S | $CH_3$ | $i-C_3H_7-S-$ |
| $CH_3$ | Cl | $t-C_4H_9$ | H | S | $CH_3$ | $i-C_3H_7-S-$ |
| $CH_3$ | Cl | $CH_3$ | $CH_3$ | S | $CH_3$ | $i-C_3H_7-S-$ |
| $CH_3$ | Cl | $C_2H_5$ | $CH_3$ | S | $CH_3$ | $i-C_3H_7-S-$ |
| $CH_3$ | Cl | $C_3H_7$ | $CH_3$ | S | $CH_3$ | $i-C_3H_7-S-$ |
| $CH_3$ | Cl | $i-C_3H_7$ | $CH_3$ | S | $CH_3$ | $i-C_3H_7-S-$ |
| $CH_3$ | Cl | $C_4H_9$ | $CH_3$ | S | $CH_3$ | $i-C_3H_7-S-$ |
| $CH_3$ | Cl | $i-C_4H_9$ | $CH_3$ | S | $CH_3$ | $i-C_3H_7-S-$ |
| $CH_3$ | Cl | $s-C_4H_9$ | $CH_3$ | S | $CH_3$ | $i-C_3H_7-S-$ |
| $CH_3$ | Cl | $t-C_4H_9$ | $CH_3$ | S | $CH_3$ | $i-C_3H_7-S-$ |
| $CH_3$ | Cl | $C_2H_5$ | $C_2H_5$ | S | $CH_3$ | $i-C_3H_7-S-$ |
| $CH_3$ | Cl | $C_3H_7$ | $C_3H_7$ | S | $CH_3$ | $i-C_3H_7-S-$ |
| $CH_3$ | Cl | 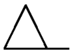 | $CH_3$ | S | $CH_3$ | $i-C_3H_7-S-$ |
| $CH_3$ | Cl | 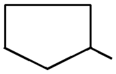 | $CH_3$ | S | $CH_3$ | $i-C_3H_7-S-$ |
| $CH_3$ | Cl | 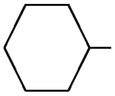 | $CH_3$ | S | $CH_3$ | $i-C_3H_7-S-$ |
| Cl | $CH_3$ | $-(CH_2)_2-$ | | S | $CH_3$ | $i-C_3H_7-S-$ |
| Cl | $CH_3$ | $-(CH_2)_4-$ | | S | $CH_3$ | $i-C_3H_7-S-$ |
| Cl | $CH_3$ | $-(CH_2)_5-$ | | S | $CH_3$ | $i-C_3H_7-S-$ |
| Cl | $CH_3$ | $-(CH_2)_6-$ | | S | $CH_3$ | $i-C_3H_7-S-$ |
| Cl | $CH_3$ | $-(CH_2)_7-$ | | S | $CH_3$ | $i-C_3H_7-S-$ |
| Cl | $CH_3$ | $-(CH_2)_2-O-(CH_2)_2-$ | | S | $CH_3$ | $i-C_3H_7-S-$ |

TABLE 5-continued

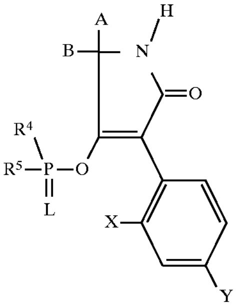

(Ie)

| X | Y | A | B | L | $R^4$ | $R^5$ |
|---|---|---|---|---|---|---|
| Cl | $CH_3$ | | $-(CH_2)_2-S-(CH_2)_2-$ | S | $CH_3$ | $i-C_3H_7-S-$ |
| Cl | $CH_3$ | | $-CH_2-CHCH_3-(CH_2)_3-$ | S | $CH_3$ | $i-C_3H_7-S-$ |
| Cl | $CH_3$ | | $-(CH_2)_2-CHCH_3-(CH_2)_2-$ | S | $CH_3$ | $i-C_3H_7-S-$ |
| Cl | $CH_3$ | | $-(CH_2)_2-CHC_2H_5-(CH_2)_2-$ | S | $CH_3$ | $i-C_3H_7-S-$ |
| Cl | $CH_3$ | | $-(CH_2)_2-CHC_3H_7-(CH_2)_2-$ | S | $CH_3$ | $i-C_3H_7-S-$ |
| Cl | $CH_3$ | | $-(CH_2)_2-CHi-C_3H_7-(CH_2)_2-$ | S | $CH_3$ | $i-C_3H_7-S-$ |
| Cl | $CH_3$ | | $-(CH_2)_2-CHOCH_3-(CH_2)_2-$ | S | $CH_3$ | $i-C_3H_7-S-$ |
| Cl | $CH_3$ | | $-(CH_2)_2-CHOC_2H_5-(CH_2)_2-$ | S | $CH_3$ | $i-C_3H_7-S-$ |
| Cl | $CH_3$ | | $-(CH_2)_2-CHOC_3H_7-(CH_2)_2-$ | S | $CH_3$ | $i-C_3H_7-S-$ |
| Cl | $CH_3$ | | $-(CH_2)_2-CHi-OC_3H_7-(CH_2)_2-$ | S | $CH_3$ | $i-C_3H_7-S-$ |
| Cl | $CH_3$ | | $-(CH_2)_2-C(CH_3)_2-(CH_2)_2-$ | S | $CH_3$ | $i-C_3H_7-S-$ |
| Cl | $CH_3$ | | $-CH_2-(CHCH_3)_2-(CH_2)_2-$ | S | $CH_3$ | $i-C_3H_7-S-$ |
| Cl | $CH_3$ | | $-CH_2-CH-(CH_2)_2-CH-$<br>$CH_2$ | S | $CH_3$ | $i-C_3H_7-S-$ |
| Cl | $CH_3$ | | $-CH_2-CH-CH-CH_2-$<br>$(CH_2)_4$ | S | $CH_3$ | $i-C_3H_7-S-$ |
| Cl | $CH_3$ | | $-CH_2-CH-CH-(CH_2)_2-$<br>$(CH_2)_3$ | S | $CH_3$ | $i-C_3H_7-S-$ |
| $CH_3$ | Cl | | $-(CH_2)_2-$ | S | $CH_3$ | $i-C_3H_7-S-$ |
| $CH_3$ | Cl | | $-(CH_2)_4-$ | S | $CH_3$ | $i-C_3H_7-S-$ |
| $CH_3$ | Cl | | $-(CH_2)_5-$ | S | $CH_3$ | $i-C_3H_7-S-$ |
| $CH_3$ | Cl | | $-(CH_2)_6-$ | S | $CH_3$ | $i-C_3H_7-S-$ |
| $CH_3$ | Cl | | $-(CH_2)_7-$ | S | $CH_3$ | $i-C_3H_7-S-$ |
| $CH_3$ | Cl | | $-(CH_2)_2-O-(CH_2)_2-$ | S | $CH_3$ | $i-C_3H_7-S-$ |
| $CH_3$ | Cl | | $-(CH_2)_2-S-(CH_2)_2-$ | S | $CH_3$ | $i-C_3H_7-S-$ |
| $CH_3$ | Cl | | $-CH_2-CHCH_3-(CH_2)_3-$ | S | $CH_3$ | $i-C_3H_7-S-$ |
| $CH_3$ | Cl | | $-(CH_2)_2-CHCH_3-(CH_2)_2-$ | S | $CH_3$ | $i-C_3H_7-S-$ |
| $CH_3$ | Cl | | $-(CH_2)_2-CHC_2H_5-(CH_2)_2-$ | S | $CH_3$ | $i-C_3H_7-S-$ |
| $CH_3$ | Cl | | $-(CH_2)_2-CHC_3H_7-(CH_2)_2-$ | S | $CH_3$ | $i-C_3H_7-S-$ |
| $CH_3$ | Cl | | $-(CH_2)_2-CHi-C_3H_7-(CH_2)_2-$ | S | $CH_3$ | $i-C_3H_7-S-$ |
| $CH_3$ | Cl | | $-(CH_2)_2-CHOCH_3-(CH_2)_2-$ | S | $CH_3$ | $i-C_3H_7-S-$ |
| $CH_3$ | Cl | | $-(CH_2)_2-CHOC_2H_5-(CH_2)_2-$ | S | $CH_3$ | $i-C_3H_7-S-$ |
| $CH_3$ | Cl | | $-(CH_2)_2-CHOC_3H_7-(CH_2)_2-$ | S | $CH_3$ | $i-C_3H_7-S-$ |
| $CH_3$ | Cl | | $-(CH_2)_2-CHi-OC_3H_7-(CH_2)_2-$ | S | $CH_3$ | $i-C_3H_7-S-$ |
| $CH_3$ | Cl | | $-(CH_2)_2-C(CH_3)_2-(CH_2)_2-$ | S | $CH_3$ | $i-C_3H_7-S-$ |
| $CH_3$ | Cl | | $-CH_2-(CHCH_3)_2-(CH_2)_2-$ | S | $CH_3$ | $i-C_3H_7-S-$ |
| $CH_3$ | Cl | | $-CH_2-CH-(CH_2)_2-CH-$<br>$CH_2$ | S | $CH_3$ | $i-C_3H_7-S-$ |
| $CH_3$ | Cl | | $-CH_2-CH-CH-CH_2-$<br>$(CH_2)_4$ | S | $CH_3$ | $i-C_3H_7-S-$ |
| $CH_3$ | Cl | | $-CH_2-CH-CH-(CH_2)_2-$<br>$(CH_2)_3$ | S | $CH_3$ | $i-C_3H_7-S-$ |
| Cl | $CH_3$ | $CH_3$ | H | S | $C_2H_5$ | $i-C_3H_7-S-$ |
| Cl | $CH_3$ | $C_2H_5$ | H | S | $C_2H_5$ | $i-C_3H_7-S-$ |
| Cl | $CH_3$ | $C_3H_7$ | H | S | $C_2H_5$ | $i-C_3H_7-S-$ |
| Cl | $CH_3$ | $i-C_3H_7$ | H | S | $C_2H_5$ | $i-C_3H_7-S-$ |
| Cl | $CH_3$ | $C_4H_9$ | H | S | $C_2H_5$ | $i-C_3H_7-S-$ |
| Cl | $CH_3$ | $i-C_4H_9$ | H | S | $C_2H_5$ | $i-C_3H_7-S-$ |
| Cl | $CH_3$ | $s-C_4H_9$ | H | S | $C_2H_5$ | $i-C_3H_7-S-$ |
| Cl | $CH_3$ | $t-C_4H_9$ | H | S | $C_2H_5$ | $i-C_3H_7-S-$ |
| Cl | $CH_3$ | $CH_3$ | $CH_3$ | S | $C_2H_5$ | $i-C_3H_7-S-$ |

TABLE 5-continued

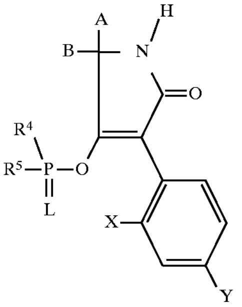

(Ie)

| X | Y | A | B | L | $R^4$ | $R^5$ |
|---|---|---|---|---|---|---|
| Cl | $CH_3$ | $C_2H_5$ | $CH_3$ | S | $C_2H_5$ | $i\text{-}C_3H_7-S-$ |
| Cl | $CH_3$ | $C_3H_7$ | $CH_3$ | S | $C_2H_5$ | $i\text{-}C_3H_7-S-$ |
| Cl | $CH_3$ | $i\text{-}C_3H_7$ | $CH_3$ | S | $C_2H_5$ | $i\text{-}C_3H_7-S-$ |
| Cl | $CH_3$ | $C_4H_9$ | $CH_3$ | S | $C_2H_5$ | $i\text{-}C_3H_7-S-$ |
| Cl | $CH_3$ | $i\text{-}C_4H_9$ | $CH_3$ | S | $C_2H_5$ | $i\text{-}C_3H_7-S-$ |
| Cl | $CH_3$ | $s\text{-}C_4H_9$ | $CH_3$ | S | $C_2H_5$ | $i\text{-}C_3H_7-S-$ |
| Cl | $CH_3$ | $t\text{-}C_4H_9$ | $CH_3$ | S | $C_2H_5$ | $i\text{-}C_3H_7-S-$ |
| Cl | $CH_3$ | $C_2H_5$ | $C_2H_5$ | S | $C_2H_5$ | $i\text{-}C_3H_7-S-$ |
| Cl | $CH_3$ | $C_3H_7$ | $C_3H_7$ | S | $C_2H_5$ | $i\text{-}C_3H_7-S-$ |
| Cl | $CH_3$ | 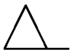 | $CH_3$ | S | $C_2H_5$ | $i\text{-}C_3H_7-S-$ |
| Cl | $CH_3$ | 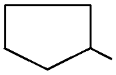 | $CH_3$ | S | $C_2H_5$ | $i\text{-}C_3H_7-S-$ |
| Cl | $CH_3$ | 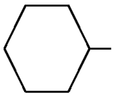 | $CH_3$ | S | $C_2H_5$ | $i\text{-}C_3H_7-S-$ |
| $CH_3$ | Cl | $CH_3$ | H | S | $C_2H_5$ | $i\text{-}C_3H_7-S-$ |
| $CH_3$ | Cl | $C_2H_5$ | H | S | $C_2H_5$ | $i\text{-}C_3H_7-S-$ |
| $CH_3$ | Cl | $C_3H_7$ | H | S | $C_2H_5$ | $i\text{-}C_3H_7-S-$ |
| $CH_3$ | Cl | $i\text{-}C_3H_7$ | H | S | $C_2H_5$ | $i\text{-}C_3H_7-S-$ |
| $CH_3$ | Cl | $C_4H_9$ | H | S | $C_2H_5$ | $i\text{-}C_3H_7-S-$ |
| $CH_3$ | Cl | $i\text{-}C_4H_9$ | H | S | $C_2H_5$ | $i\text{-}C_3H_7-S-$ |
| $CH_3$ | Cl | $s\text{-}C_4H_9$ | H | S | $C_2H_5$ | $i\text{-}C_3H_7-S-$ |
| $CH_3$ | Cl | $t\text{-}C_4H_9$ | H | S | $C_2H_5$ | $i\text{-}C_3H_7-S-$ |
| $CH_3$ | Cl | $CH_3$ | $CH_3$ | S | $C_2H_5$ | $i\text{-}C_3H_7-S-$ |
| $CH_3$ | Cl | $C_2H_5$ | $CH_3$ | S | $C_2H_5$ | $i\text{-}C_3H_7-S-$ |
| $CH_3$ | Cl | $C_3H_7$ | $CH_3$ | S | $C_2H_5$ | $i\text{-}C_3H_7-S-$ |
| $CH_3$ | Cl | $i\text{-}C_3H_7$ | $CH_3$ | S | $C_2H_5$ | $i\text{-}C_3H_7-S-$ |
| $CH_3$ | Cl | $C_4H_9$ | $CH_3$ | S | $C_2H_5$ | $i\text{-}C_3H_7-S-$ |
| $CH_3$ | Cl | $i\text{-}C_4H_9$ | $CH_3$ | S | $C_2H_5$ | $i\text{-}C_3H_7-S-$ |
| $CH_3$ | Cl | $s\text{-}C_4H_9$ | $CH_3$ | S | $C_2H_5$ | $i\text{-}C_3H_7-S-$ |
| $CH_3$ | Cl | $t\text{-}C_4H_9$ | $CH_3$ | S | $C_2H_5$ | $i\text{-}C_3H_7-S-$ |
| $CH_3$ | Cl | $C_2H_5$ | $C_2H_5$ | S | $C_2H_5$ | $i\text{-}C_3H_7-S-$ |
| $CH_3$ | Cl | $C_3H_7$ | $C_3H_7$ | S | $C_2H_5$ | $i\text{-}C_3H_7-S-$ |
| $CH_3$ | Cl | 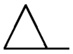 | $CH_3$ | S | $C_2H_5$ | $i\text{-}C_3H_7-S-$ |
| $CH_3$ | Cl | 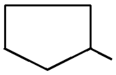 | $CH_3$ | S | $C_2H_5$ | $i\text{-}C_3H_7-S-$ |
| $CH_3$ | Cl | 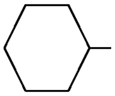 | $CH_3$ | S | $C_2H_5$ | $i\text{-}C_3H_7-S-$ |
| Cl | $CH_3$ | $-(CH_2)_2-$ | | S | $C_2H_5$ | $i\text{-}C_3H_7-S-$ |
| Cl | $CH_3$ | $-(CH_2)_4-$ | | S | $C_2H_5$ | $i\text{-}C_3H_7-S-$ |
| Cl | $CH_3$ | $-(CH_2)_5-$ | | S | $C_2H_5$ | $i\text{-}C_3H_7-S-$ |
| Cl | $CH_3$ | $-(CH_2)_6-$ | | S | $C_2H_5$ | $i\text{-}C_3H_7-S-$ |
| Cl | $CH_3$ | $-(CH_2)_7-$ | | S | $C_2H_5$ | $i\text{-}C_3H_7-S-$ |
| Cl | $CH_3$ | $-(CH_2)_2-O-(CH_2)_2-$ | | S | $C_2H_5$ | $i\text{-}C_3H_7-S-$ |
| Cl | $CH_3$ | $-(CH_2)_2-S-(CH_2)_2-$ | | S | $C_2H_5$ | $i\text{-}C_3H_7-S-$ |

TABLE 5-continued

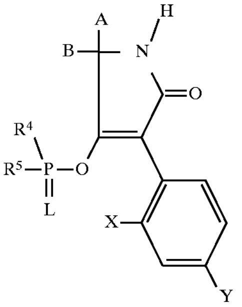

(Ie)

| X | Y | A | B | L | $R^4$ | $R^5$ |
|---|---|---|---|---|---|---|
| Cl | $CH_3$ | | $-CH_2-CHCH_3-(CH_2)_3-$ | S | $C_2H_5$ | $i-C_3H_7-S-$ |
| Cl | $CH_3$ | | $-(CH_2)_2-CHCH_3-(CH_2)_2-$ | S | $C_2H_5$ | $i-C_3H_7-S-$ |
| Cl | $CH_3$ | | $-(CH_2)_2-CHC_2H_5-(CH_2)_2-$ | S | $C_2H_5$ | $i-C_3H_7-S-$ |
| Cl | $CH_3$ | | $-(CH_2)_2-CHC_3H_7-(CH_2)_2-$ | S | $C_2H_5$ | $i-C_3H_7-S-$ |
| Cl | $CH_3$ | | $-(CH_2)_2-CHi-C_3H_7-(CH_2)_2-$ | S | $C_2H_5$ | $i-C_3H_7-S-$ |
| Cl | $CH_3$ | | $-(CH_2)_2-CHOCH_3-(CH_2)_2-$ | S | $C_2H_5$ | $i-C_3H_7-S-$ |
| Cl | $CH_3$ | | $-(CH_2)_2-CHOC_2H_5-(CH_2)_2-$ | S | $C_2H_5$ | $i-C_3H_7-S-$ |
| Cl | $CH_3$ | | $-(CH_2)_2-CHOC_3H_7-(CH_2)_2-$ | S | $C_2H_5$ | $i-C_3H_7-S-$ |
| Cl | $CH_3$ | | $-(CH_2)_2-CHi-OC_3H_7-(CH_2)_2-$ | S | $C_2H_5$ | $i-C_3H_7-S-$ |
| Cl | $CH_3$ | | $-(CH_2)_2-C(CH_3)_2-(CH_2)_2-$ | S | $C_2H_5$ | $i-C_3H_7-S-$ |
| Cl | $CH_3$ | | $-CH_2-(CHCH_3)_2-(CH_2)_2-$ | S | $C_2H_5$ | $i-C_3H_7-S-$ |
| Cl | $CH_3$ | | $-CH_2-CH-(CH_2)_2-CH-$<br>$CH_2$ | S | $C_2H_5$ | $i-C_3H_7-S-$ |
| Cl | $CH_3$ | | $-CH_2-CH-CH-CH_2-$<br>$(CH_2)_4$ | S | $C_2H_5$ | $i-C_3H_7-S-$ |
| Cl | $CH_3$ | | $-CH_2-CH-CH-(CH_2)_2-$<br>$(CH_2)_3$ | S | $C_2H_5$ | $i-C_3H_7-S-$ |
| $CH_3$ | Cl | | $-(CH_2)_2-$ | S | $C_2H_5$ | $i-C_3H_7-S-$ |
| $CH_3$ | Cl | | $-(CH_2)_4-$ | S | $C_2H_5$ | $i-C_3H_7-S-$ |
| $CH_3$ | Cl | | $-(CH_2)_5-$ | S | $C_2H_5$ | $i-C_3H_7-S-$ |
| $CH_3$ | Cl | | $-(CH_2)_6-$ | S | $C_2H_5$ | $i-C_3H_7-S-$ |
| $CH_3$ | Cl | | $-(CH_2)_7-$ | S | $C_2H_5$ | $i-C_3H_7-S-$ |
| $CH_3$ | Cl | | $-(CH_2)_2-O-(CH_2)_2-$ | S | $C_2H_5$ | $i-C_3H_7-S-$ |
| $CH_3$ | Cl | | $-(CH_2)_2-S-(CH_2)_2-$ | S | $C_2H_5$ | $i-C_3H_7-S-$ |
| $CH_3$ | Cl | | $-CH_2-CHCH_3-(CH_2)_3-$ | S | $C_2H_5$ | $i-C_3H_7-S-$ |
| $CH_3$ | Cl | | $-(CH_2)_2-CHCH_3-(CH_2)_2-$ | S | $C_2H_5$ | $i-C_3H_7-S-$ |
| $CH_3$ | Cl | | $-(CH_2)_2-CHC_2H_5-(CH_2)_2-$ | S | $C_2H_5$ | $i-C_3H_7-S-$ |
| $CH_3$ | Cl | | $-(CH_2)_2-CHC_3H_7-(CH_2)_2-$ | S | $C_2H_5$ | $i-C_3H_7-S-$ |
| $CH_3$ | Cl | | $-(CH_2)_2-CHi-C_3H_7-(CH_2)_2-$ | S | $C_2H_5$ | $i-C_3H_7-S-$ |
| $CH_3$ | Cl | | $-(CH_2)_2-CHOCH_3-(CH_2)_2-$ | S | $C_2H_5$ | $i-C_3H_7-S-$ |
| $CH_3$ | Cl | | $-(CH_2)_2-CHOC_2H_5-(CH_2)_2-$ | S | $C_2H_5$ | $i-C_3H_7-S-$ |
| $CH_3$ | Cl | | $-(CH_2)_2-CHOC_3H_7-(CH_2)_2-$ | S | $C_2H_5$ | $i-C_3H_7-S-$ |
| $CH_3$ | Cl | | $-(CH_2)_2-CHi-OC_3H_7-(CH_2)_2-$ | S | $C_2H_5$ | $i-C_3H_7-S-$ |
| $CH_3$ | Cl | | $-(CH_2)_2-C(CH_3)_2-(CH_2)_2-$ | S | $C_2H_5$ | $i-C_3H_7-S-$ |
| $CH_3$ | Cl | | $-CH_2-(CHCH_3)_2-(CH_2)_2-$ | S | $C_2H_5$ | $i-C_3H_7-S-$ |
| $CH_3$ | Cl | | $-CH_2-CH-(CH_2)_2-CH-$<br>$CH_2$ | S | $C_2H_5$ | $i-C_3H_7-S-$ |
| $CH_3$ | Cl | | $-CH_2-CH-CH-CH_2-$<br>$(CH_2)_4$ | S | $C_2H_5$ | $i-C_3H_7-S-$ |
| $CH_3$ | Cl | | $-CH_2-CH-CH-(CH_2)_2-$<br>$(CH_2)_3$ | S | $C_2H_5$ | $i-C_3H_7-S-$ |
| Cl | $CH_3$ | $CH_3$ | H | O | $CH_3$ | $i-C_3H_7-S-$ |
| Cl | $CH_3$ | $C_2H_5$ | H | O | $CH_3$ | $i-C_3H_7-S-$ |
| Cl | $CH_3$ | $C_3H_7$ | H | O | $CH_3$ | $i-C_3H_7-S-$ |
| Cl | $CH_3$ | $i-C_3H_7$ | H | O | $CH_3$ | $i-C_3H_7-S-$ |
| Cl | $CH_3$ | $C_4H_9$ | H | O | $CH_3$ | $i-C_3H_7-S-$ |
| Cl | $CH_3$ | $i-C_4H_9$ | H | O | $CH_3$ | $i-C_3H_7-S-$ |
| Cl | $CH_3$ | $s-C_4H_9$ | H | O | $CH_3$ | $i-C_3H_7-S-$ |
| Cl | $CH_3$ | $t-C_4H_9$ | H | O | $CH_3$ | $i-C_3H_7-S-$ |
| Cl | $CH_3$ | $CH_3$ | $CH_3$ | O | $CH_3$ | $i-C_3H_7-S-$ |
| Cl | $CH_3$ | $C_2H_5$ | $CH_3$ | O | $CH_3$ | $i-C_3H_7-S-$ |

TABLE 5-continued

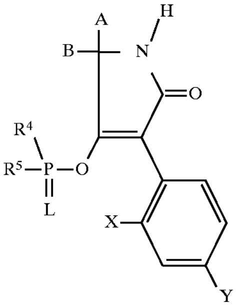

(Ie)

| X | Y | A | B | L | $R^4$ | $R^5$ |
|---|---|---|---|---|---|---|
| Cl | $CH_3$ | $C_3H_7$ | $CH_3$ | O | $CH_3$ | $i\text{-}C_3H_7-S-$ |
| Cl | $CH_3$ | $i\text{-}C_3H_7$ | $CH_3$ | O | $CH_3$ | $i\text{-}C_3H_7-S-$ |
| Cl | $CH_3$ | $C_4H_9$ | $CH_3$ | O | $CH_3$ | $i\text{-}C_3H_7-S-$ |
| Cl | $CH_3$ | $i\text{-}C_4H_9$ | $CH_3$ | O | $CH_3$ | $i\text{-}C_3H_7-S-$ |
| Cl | $CH_3$ | $s\text{-}C_4H_9$ | $CH_3$ | O | $CH_3$ | $i\text{-}C_3H_7-S-$ |
| Cl | $CH_3$ | $t\text{-}C_4H_9$ | $CH_3$ | O | $CH_3$ | $i\text{-}C_3H_7-S-$ |
| Cl | $CH_3$ | $C_2H_5$ | $C_2H_5$ | O | $CH_3$ | $i\text{-}C_3H_7-S-$ |
| Cl | $CH_3$ | $C_3H_7$ | $C_3H_7$ | O | $CH_3$ | $i\text{-}C_3H_7-S-$ |
| Cl | $CH_3$ | 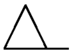 | $CH_3$ | O | $CH_3$ | $i\text{-}C_3H_7-S-$ |
| Cl | $CH_3$ | 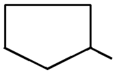 | $CH_3$ | O | $CH_3$ | $i\text{-}C_3H_7-S-$ |
| Cl | $CH_3$ | 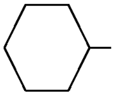 | $CH_3$ | O | $CH_3$ | $i\text{-}C_3H_7-S-$ |
| $CH_3$ | Cl | $CH_3$ | H | O | $CH_3$ | $i\text{-}C_3H_7-S-$ |
| $CH_3$ | Cl | $C_2H_5$ | H | O | $CH_3$ | $i\text{-}C_3H_7-S-$ |
| $CH_3$ | Cl | $C_3H_7$ | H | O | $CH_3$ | $i\text{-}C_3H_7-S-$ |
| $CH_3$ | Cl | $i\text{-}C_3H_7$ | H | O | $CH_3$ | $i\text{-}C_3H_7-S-$ |
| $CH_3$ | Cl | $C_4H_9$ | H | O | $CH_3$ | $i\text{-}C_3H_7-S-$ |
| $CH_3$ | Cl | $i\text{-}C_4H_9$ | H | O | $CH_3$ | $i\text{-}C_3H_7-S-$ |
| $CH_3$ | Cl | $s\text{-}C_4H_9$ | H | O | $CH_3$ | $i\text{-}C_3H_7-S-$ |
| $CH_3$ | Cl | $t\text{-}C_4H_9$ | H | O | $CH_3$ | $i\text{-}C_3H_7-S-$ |
| $CH_3$ | Cl | $CH_3$ | $CH_3$ | O | $CH_3$ | $i\text{-}C_3H_7-S-$ |
| $CH_3$ | Cl | $C_2H_5$ | $CH_3$ | O | $CH_3$ | $i\text{-}C_3H_7-S-$ |
| $CH_3$ | Cl | $C_3H_7$ | $CH_3$ | O | $CH_3$ | $i\text{-}C_3H_7-S-$ |
| $CH_3$ | Cl | $i\text{-}C_3H_7$ | $CH_3$ | O | $CH_3$ | $i\text{-}C_3H_7-S-$ |
| $CH_3$ | Cl | $C_4H_9$ | $CH_3$ | O | $CH_3$ | $i\text{-}C_3H_7-S-$ |
| $CH_3$ | Cl | $i\text{-}C_4H_9$ | $CH_3$ | O | $CH_3$ | $i\text{-}C_3H_7-S-$ |
| $CH_3$ | Cl | $s\text{-}C_4H_9$ | $CH_3$ | O | $CH_3$ | $i\text{-}C_3H_7-S-$ |
| $CH_3$ | Cl | $t\text{-}C_4H_9$ | $CH_3$ | O | $CH_3$ | $i\text{-}C_3H_7-S-$ |
| $CH_3$ | Cl | $C_2H_5$ | $C_2H_5$ | O | $CH_3$ | $i\text{-}C_3H_7-S-$ |
| $CH_3$ | Cl | $C_3H_7$ | $C_3H_7$ | O | $CH_3$ | $i\text{-}C_3H_7-S-$ |
| $CH_3$ | Cl | 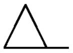 | $CH_3$ | O | $CH_3$ | $i\text{-}C_3H_7-S-$ |
| $CH_3$ | Cl | 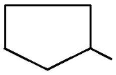 | $CH_3$ | O | $CH_3$ | $i\text{-}C_3H_7-S-$ |
| $CH_3$ | Cl | 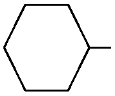 | $CH_3$ | O | $CH_3$ | $i\text{-}C_3H_7-S-$ |
| Cl | $CH_3$ | $-(CH_2)_2-$ | | O | $CH_3$ | $i\text{-}C_3H_7-S-$ |
| Cl | $CH_3$ | $-(CH_2)_4-$ | | O | $CH_3$ | $i\text{-}C_3H_7-S-$ |
| Cl | $CH_3$ | $-(CH_2)_5-$ | | O | $CH_3$ | $i\text{-}C_3H_7-S-$ |
| Cl | $CH_3$ | $-(CH_2)_6-$ | | O | $CH_3$ | $i\text{-}C_3H_7-S-$ |
| Cl | $CH_3$ | $-(CH_2)_7-$ | | O | $CH_3$ | $i\text{-}C_3H_7-S-$ |
| Cl | $CH_3$ | $-(CH_2)_2-O-(CH_2)_2-$ | | O | $CH_3$ | $i\text{-}C_3H_7-S-$ |
| Cl | $CH_3$ | $-(CH_2)_2-S-(CH_2)_2-$ | | O | $CH_3$ | $i\text{-}C_3H_7-S-$ |
| Cl | $CH_3$ | $-CH_2-CHCH_3-(CH_2)_3-$ | | O | $CH_3$ | $i\text{-}C_3H_7-S-$ |

TABLE 5-continued

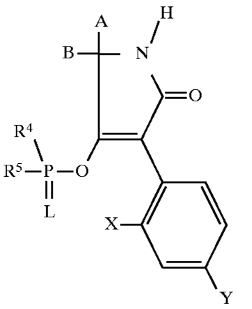

(Ie)

| X | Y | A | B | L | $R^4$ | $R^5$ |
|---|---|---|---|---|---|---|
| Cl | $CH_3$ | | $-(CH_2)_2-CHCH_3-(CH_2)_2-$ | O | $CH_3$ | $i-C_3H_7-S-$ |
| Cl | $CH_3$ | | $-(CH_2)_2-CHC_2H_5-(CH_2)_2-$ | O | $CH_3$ | $i-C_3H_7-S-$ |
| Cl | $CH_3$ | | $-(CH_2)_2-CHC_3H_7-(CH_2)2-$ | O | $CH_3$ | $i-C_3H_7-S-$ |
| Cl | $CH_3$ | | $-(CH_2)_2-CHi-C_3H_7-(CH_2)_2-$ | O | $CH_3$ | $i-C_3H_7-S-$ |
| Cl | $CH_3$ | | $-(CH_2)_2-CHOCH_3-(CH_2)_2-$ | O | $CH_3$ | $i-C_3H_7-S-$ |
| Cl | $CH_3$ | | $-(CH_2)_2-CHOC_2H_5-(CH2)_2-$ | O | $CH_3$ | $i-C_3H_7-S-$ |
| Cl | $CH_3$ | | $-(CH_2)_2-CHOC_3H_7-(CH_2)_2-$ | O | $CH_3$ | $i-C_3H_7-S-$ |
| Cl | $CH_3$ | | $-(CH_2)_2-CHi-OC_3H_7-(CH_2)_2-$ | O | $CH_3$ | $i-C_3H_7-S-$ |
| Cl | $CH_3$ | | $-(CH_2)_2-C(CH_3)_2-(CH_2)_2-$ | O | $CH_3$ | $i-C_3H_7-S-$ |
| Cl | $CH_3$ | | $-CH_2-(CHCH_3)_2-(CH_2)_2-$ | O | $CH_3$ | $i-C_3H_7-S-$ |
| Cl | $CH_3$ | | $-CH_2-CH-(CH_2)_2-CH-$<br>$CH_2$ | O | $CH_3$ | $i-C_3H_7-S-$ |
| Cl | $CH_3$ | | $-CH_2-CH-CH-CH_2-$<br>$(CH_2)_4$ | O | $CH_3$ | $i-C_3H_7-S-$ |
| Cl | $CH_3$ | | $-CH_2-CH-CH-(CH_2)_2-$<br>$(CH_2)_3$ | O | $CH_3$ | $i-C_3H_7-S-$ |
| $CH_3$ | Cl | | $-(CH_2)_2-$ | O | $CH_3$ | $i-C_3H_7-S-$ |
| $CH_3$ | Cl | | $-(CH_2)_4-$ | O | $CH_3$ | $i-C_3H_7-S-$ |
| $CH_3$ | Cl | | $-(CH_2)_5-$ | O | $CH_3$ | $i-C_3H_7-S-$ |
| $CH_3$ | Cl | | $-(CH_2)_6-$ | O | $CH_3$ | $i-C_3H_7-S-$ |
| $CH_3$ | Cl | | $-(CH_2)_7-$ | O | $CH_3$ | $i-C_3H_7-S-$ |
| $CH_3$ | Cl | | $-(CH_2)_2-O-(CH_2)_2-$ | O | $CH_3$ | $i-C_3H_7-S-$ |
| $CH_3$ | Cl | | $-(CH_2)_2-S-(CH_2)_2-$ | O | $CH_3$ | $i-C_3H_7-S-$ |
| $CH_3$ | Cl | | $-CH_2-CHCH_3-(CH_2)_3-$ | O | $CH_3$ | $i-C_3H_7-S-$ |
| $CH_3$ | Cl | | $-(CH_2)_2-CHCH_3-(CH_2)_2-$ | O | $CH_3$ | $i-C_3H_7-S-$ |
| $CH_3$ | Cl | | $-(CH_2)_2-CHC_2H_5-(CH_2)_2-$ | O | $CH_3$ | $i-C_3H_7-S-$ |
| $CH_3$ | Cl | | $-(CH_2)_2-CHC_3H_7-(CH_2)_2-$ | O | $CH_3$ | $i-C_3H_7-S-$ |
| $CH_3$ | Cl | | $-(CH_2)_2-CHi-C_3H_7-(CH_2)_2-$ | O | $CH_3$ | $i-C_3H_7-S-$ |
| $CH_3$ | Cl | | $-(CH_2)_2-CHOCH_3-(CH_2)_2-$ | O | $CH_3$ | $i-C_3H_7-S-$ |
| $CH_3$ | Cl | | $-(CH_2)_2-CHOC_2H_5-(CH_2)_2-$ | O | $CH_3$ | $i-C_3H_7-S-$ |
| $CH_3$ | Cl | | $-(CH_2)_2-CHOC_3H_7-(CH_2)_2-$ | O | $CH_3$ | $i-C_3H_7-S-$ |
| $CH_3$ | Cl | | $-(CH_2)_2-CHi-OC_3H_7-(CH_2)_2-$ | O | $CH_3$ | $i-C_3H_7-S-$ |
| $CH_3$ | Cl | | $-(CH_2)_2-C(CH_3)_2-(CH_2)_2-$ | O | $CH_3$ | $i-C_3H_7-S-$ |
| $CH_3$ | Cl | | $-CH_2-(CHCH_3)_2-(CH_2)_2-$ | O | $CH_3$ | $i-C_3H_7-S-$ |
| $CH_3$ | Cl | | $-CH_2-CH-(CH_2)_2-CH-$<br>$CH_2$ | O | $CH_3$ | $i-C_3H_7-S-$ |
| $CH_3$ | Cl | | $-CH_2-CH-CH-CH_2-$<br>$(CH_2)_4$ | O | $CH_3$ | $i-C_3H_7-S-$ |
| $CH_3$ | Cl | | $-CH_2-CH-CH-(CH_2)_2-$<br>$(CH_2)_3$ | O | $CH_3$ | $i-C_3H_7-S-$ |
| Cl | $CH_3$ | $CH_3$ | H | O | $C_2H_5$ | $i-C_3H_7-S-$ |
| Cl | $CH_3$ | $C_2H_5$ | H | O | $C_2H_5$ | $i-C_3H_7-S-$ |
| Cl | $CH_3$ | $C_3H_7$ | H | O | $C_2H_5$ | $i-C_3H_7-S-$ |
| Cl | $CH_3$ | $i-C_3H_7$ | H | O | $C_2H_5$ | $i-C_3H_7-S-$ |
| Cl | $CH_3$ | $C_4H_9$ | H | O | $C_2H_5$ | $i-C_3H_7-S-$ |
| Cl | $CH_3$ | $i-C_4H_9$ | H | O | $C_2H_5$ | $i-C_3H_7-S-$ |
| Cl | $CH_3$ | $s-C_4H_9$ | H | O | $C_2H_5$ | $i-C_3H_7-S-$ |
| Cl | $CH_3$ | $t-C_4H_9$ | H | O | $C_2H_5$ | $i-C_3H_7-S-$ |
| Cl | $CH_3$ | $CH_3$ | $CH_3$ | O | $C_2H_5$ | $i-C_3H_7-S-$ |
| Cl | $CH_3$ | $C_2H_5$ | $CH_3$ | O | $C_2H_5$ | $i-C_3H_7-S-$ |
| Cl | $CH_3$ | $C_3H_7$ | $CH_3$ | O | $C_2H_5$ | $i-C_3H_7-S-$ |

TABLE 5-continued

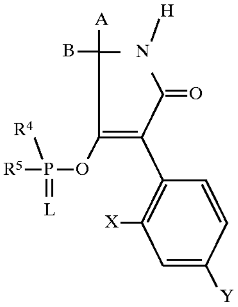
(Ie)

| X | Y | A | B | L | $R^4$ | $R^5$ |
|---|---|---|---|---|---|---|
| Cl | $CH_3$ | i-$C_3H_7$ | $CH_3$ | O | $C_2H_5$ | i-$C_3H_7$—S— |
| Cl | $CH_3$ | $C_4H_9$ | $CH_3$ | O | $C_2H_5$ | i-$C_3H_7$—S— |
| Cl | $CH_3$ | i-$C_4H_9$ | $CH_3$ | O | $C_2H_5$ | i-$C_3H_7$—S— |
| Cl | $CH_3$ | s-$C_4H_9$ | $CH_3$ | O | $C_2H_5$ | i-$C_3H_7$—S— |
| Cl | $CH_3$ | t-$C_4H_9$ | $CH_3$ | O | $C_2H_5$ | i-$C_3H_7$—S— |
| Cl | $CH_3$ | $C_2H_5$ | $C_2H_5$ | O | $C_2H_5$ | i-$C_3H_7$—S— |
| Cl | $CH_3$ | $C_3H_7$ | $C_3H_7$ | O | $C_2H_5$ | i-$C_3H_7$—S— |
| Cl | $CH_3$ | 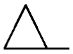 | $CH_3$ | O | $C_2H_5$ | i-$C_3H_7$—S— |
| Cl | $CH_3$ | 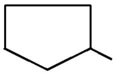 | $CH_3$ | O | $C_2H_5$ | i-$C_3H_7$—S— |
| Cl | $CH_3$ | 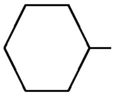 | $CH_3$ | O | $C_2H_5$ | i-$C_3H_7$—S— |
| $CH_3$ | Cl | $CH_3$ | H | O | $C_2H_5$ | i-$C_3H_7$—S— |
| $CH_3$ | Cl | $C_2H_5$ | H | O | $C_2H_5$ | i-$C_3H_7$—S— |
| $CH_3$ | Cl | $C_3H_7$ | H | O | $C_2H_5$ | i-$C_3H_7$—S— |
| $CH_3$ | Cl | i-$C_3H_7$ | H | O | $C_2H_5$ | i-$C_3H_7$—S— |
| $CH_3$ | Cl | $C_4H_9$ | H | O | $C_2H_5$ | i-$C_3H_7$—S— |
| $CH_3$ | Cl | i-$C_4H_9$ | H | O | $C_2H_5$ | i-$C_3H_7$—S— |
| $CH_3$ | Cl | s-$C_4H_9$ | H | O | $C_2H_5$ | i-$C_3H_7$—S— |
| $CH_3$ | Cl | t-$C_4H_9$ | H | O | $C_2H_5$ | i-$C_3H_7$—S— |
| $CH_3$ | Cl | $CH_3$ | $CH_3$ | O | $C_2H_5$ | i-$C_3H_7$—S— |
| $CH_3$ | Cl | $C_2H_5$ | $CH_3$ | O | $C_2H_5$ | i-$C_3H_7$—S— |
| $CH_3$ | Cl | $C_3H_7$ | $CH_3$ | O | $C_2H_5$ | i-$C_3H_7$—S— |
| $CH_3$ | Cl | i-$C_3H_7$ | $CH_3$ | O | $C_2H_5$ | i-$C_3H_7$—S— |
| $CH_3$ | Cl | $C_4H_9$ | $CH_3$ | O | $C_2H_5$ | i-$C_3H_7$—S— |
| $CH_3$ | Cl | i-$C_4H_9$ | $CH_3$ | O | $C_2H_5$ | i-$C_3H_7$—S— |
| $CH_3$ | Cl | s-$C_4H_9$ | $CH_3$ | O | $C_2H_5$ | i-$C_3H_7$—S— |
| $CH_3$ | Cl | t-$C_4H_9$ | $CH_3$ | O | $C_2H_5$ | i-$C_3H_7$—S— |
| $CH_3$ | Cl | $C_2H_5$ | $C_2H_5$ | O | $C_2H_5$ | i-$C_3H_7$—S— |
| $CH_3$ | Cl | $C_3H_7$ | $C_3H_7$ | O | $C_2H_5$ | i-$C_3H_7$—S— |
| $CH_3$ | Cl | 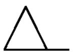 | $CH_3$ | O | $C_2H_5$ | i-$C_3H_7$—S— |
| $CH_3$ | Cl | 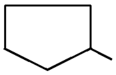 | $CH_3$ | O | $C_2H_5$ | i-$C_3H_7$—S— |
| $CH_3$ | Cl | 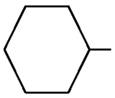 | $CH_3$ | O | $C_2H_5$ | i-$C_3H_7$—S— |
| Cl | $CH_3$ | $-(CH_2)_2-$ | | O | $C_2H_5$ | i-$C_3H_7$—S— |
| Cl | $CH_3$ | $-(CH_2)_4-$ | | O | $C_2H_5$ | i-$C_3H_7$—S— |
| Cl | $CH_3$ | $-(CH_2)_5-$ | | O | $C_2H_5$ | i-$C_3H_7$—S— |
| Cl | $CH_3$ | $-(CH_2)_6-$ | | O | $C_2H_5$ | i-$C_3H_7$—S— |
| Cl | $CH_3$ | $-(CH_2)_7-$ | | O | $C_2H_5$ | i-$C_3H_7$—S— |
| Cl | $CH_3$ | $-(CH_2)_2-O-(CH_2)_2-$ | | O | $C_2H_5$ | i-$C_3H_7$—S— |
| Cl | $CH_3$ | $-(CH_2)_2-S-(CH_2)_2-$ | | O | $C_2H_5$ | i-$C_3H_7$—S— |
| Cl | $CH_3$ | $-CH_2-CHCH_3-(CH_2)_3-$ | | O | $C_2H_5$ | i-$C_3H_7$—S— |
| Cl | $CH_3$ | $-(CH_2)_2-CHCH_3-(CH_2)_2-$ | | O | $C_2H_5$ | i-$C_3H_7$—S— |

TABLE 5-continued

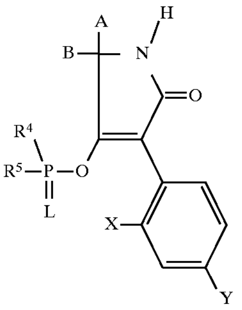

(Ie)

| X | Y | A | B | L | $R^4$ | $R^5$ |
|---|---|---|---|---|---|---|
| Cl | $CH_3$ | | $-(CH_2)_2-CHC_2H_5-(CH_2)_2-$ | O | $C_2H_5$ | $i\text{-}C_3H_7-S-$ |
| Cl | $CH_3$ | | $-(CH_2)_2-CHC_3H_7-(CH_2)_2-$ | O | $C_2H_5$ | $i\text{-}C_3H_7-S-$ |
| Cl | $CH_3$ | | $-(CH_2)_2-CHi\text{-}C_3H_7-(CH_2)_2-$ | O | $C_2H_5$ | $i\text{-}C_3H_7-S-$ |
| Cl | $CH_3$ | | $-(CH_2)_2-CHOCH_3-(CH_2)_2-$ | O | $C_2H_5$ | $i\text{-}C_3H_7-S-$ |
| Cl | $CH_3$ | | $-(CH_2)_2-CHOC_2H_5-(CH_2)_2-$ | O | $C_2H_5$ | $i\text{-}C_3H_7-S-$ |
| Cl | $CH_3$ | | $-(CH_2)_2-CHOC_3H_7-(CH_2)_2-$ | O | $C_2H_5$ | $i\text{-}C_3H_7-S-$ |
| Cl | $CH_3$ | | $-(CH_2)_2-CHi\text{-}OC_3H_7-(CH_2)_2-$ | O | $C_2H_5$ | $i\text{-}C_3H_7-S-$ |
| Cl | $CH_3$ | | $-(CH_2)_2-C(CH_3)_2-(CH_2)_2-$ | O | $C_2H_5$ | $i\text{-}C_3H_7-S-$ |
| Cl | $CH_3$ | | $-CH_2-(CHCH_3)_2-(CH_2)_2-$ | O | $C_2H_5$ | $i\text{-}C_3H_7-S-$ |
| Cl | $CH_3$ | | $-CH_2-CH-(CH_2)_2-CH-$<br>$CH_2$ | O | $C_2H_5$ | $i\text{-}C_3H_7-S-$ |
| Cl | $CH_3$ | | $-CH_2-CH-CH-CH_2-$<br>$(CH_2)_4$ | O | $C_2H_5$ | $i\text{-}C_3H_7-S-$ |
| Cl | $CH_3$ | | $-CH_2-CH-CH-(CH_2)_2-$<br>$(CH_2)_3$ | O | $C_2H_5$ | $i\text{-}C_3H_7-S-$ |
| $CH_3$ | Cl | | $-(CH_2)_2-$ | O | $C_2H_5$ | $i\text{-}C_3H_7-S-$ |
| $CH_3$ | Cl | | $-(CH_2)_4-$ | O | $C_2H_5$ | $i\text{-}C_3H_7-S-$ |
| $CH_3$ | Cl | | $-(CH_2)_5-$ | O | $C_2H_5$ | $i\text{-}C_3H_7-S-$ |
| $CH_3$ | Cl | | $-(CH_2)_6-$ | O | $C_2H_5$ | $i\text{-}C_3H_7-S-$ |
| $CH_3$ | Cl | | $-(CH_2)_7-$ | O | $C_2H_5$ | $i\text{-}C_3H_7-S-$ |
| $CH_3$ | Cl | | $-(CH_2)_2-O-(CH_2)_2-$ | O | $C_2H_5$ | $i\text{-}C_3H_7-S-$ |
| $CH_3$ | Cl | | $-(CH_2)_2-S-(CH_2)_2-$ | O | $C_2H_5$ | $i\text{-}C_3H_7-S-$ |
| $CH_3$ | Cl | | $-CH_2-CHCH_3-(CH_2)_3-$ | O | $C_2H_5$ | $i\text{-}C_3H_7-S-$ |
| $CH_3$ | Cl | | $-(CH_2)_2-CHCH_3-(CH_2)_2-$ | O | $C_2H_5$ | $i\text{-}C_3H_7-S-$ |
| $CH_3$ | Cl | | $-(CH_2)_2-CHC_2H_5-(CH_2)_2-$ | O | $C_2H_5$ | $i\text{-}C_3H_7-S-$ |
| $CH_3$ | Cl | | $-(CH_2)_2-CHC_3H_7-(CH_2)_2-$ | O | $C_2H_5$ | $i\text{-}C_3H_7-S-$ |
| $CH_3$ | Cl | | $-(CH_2)_2-CHi\text{-}C_3H_7-(CH_2)_2-$ | O | $C_2H_5$ | $i\text{-}C_3H_7-S-$ |
| $CH_3$ | Cl | | $-(CH_2)_2-CHOCH_3-(CH_2)_2-$ | O | $C_2H_5$ | $i\text{-}C_3H_7-S-$ |
| $CH_3$ | Cl | | $-(CH_2)_2-CHOC_2H_5-(CH_2)_2-$ | O | $C_2H_5$ | $i\text{-}C_3H_7-S-$ |
| $CH_3$ | Cl | | $-(CH_2)_2-CHOC_3H_7-(CH_2)_2-$ | O | $C_2H_5$ | $i\text{-}C_3H_7-S-$ |
| $CH_3$ | Cl | | $-(CH_2)_2-CHi\text{-}OC_3H_7-(CH_2)_2-$ | O | $C_2H_5$ | $i\text{-}C_3H_7-S-$ |
| $CH_3$ | Cl | | $-(CH_2)_2-C(CH_3)_2-(CH_2)_2-$ | O | $C_2H_5$ | $i\text{-}C_3H_7-S-$ |
| $CH_3$ | Cl | | $-CH_2-(CHCH_3)_2-(CH_2)_2-$ | O | $C_2H_5$ | $i\text{-}C_3H_7-S-$ |
| $CH_3$ | Cl | | $-CH_2-CH-(CH_2)_2-CH-$<br>$CH_2$ | O | $C_2H_5$ | $i\text{-}C_3H_7-S-$ |
| $CH_3$ | Cl | | $-CH_2-CH-CH-CH_2-$<br>$(CH_2)_4$ | O | $C_2H_5$ | $i\text{-}C_3H_7-S-$ |
| $CH_3$ | Cl | | $-CH_2-CH-CH-(CH_2)_2-$<br>$(CH_2)_3$ | O | $C_2H_5$ | $i\text{-}C_3H_7-S-$ |

The following compounds of the formula (If-a) may be mentioned individually in addition to the compounds mentioned in the preparation examples:

TABLE 6a

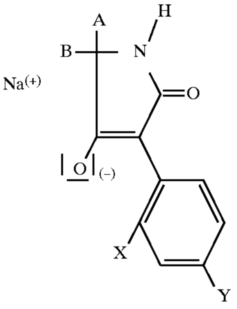

(If-a)

| X | Y | A | B |
|---|---|---|---|
| Cl | $CH_3$ | $CH_3$ | H |
| Cl | $CH_3$ | $C_2H_5$ | H |
| Cl | $CH_3$ | $C_3H_7$ | H |
| Cl | $CH_3$ | i-$C_3H_7$ | H |
| Cl | $CH_3$ | $C_4H_9$ | H |
| Cl | $CH_3$ | i-$C_4H_9$ | H |
| Cl | $CH_3$ | s-$C_4H_9$ | H |
| Cl | $CH_3$ | t-$C_4H_9$ | H |
| Cl | $CH_3$ | $CH_3$ | $CH_3$ |
| Cl | $CH_3$ | $C_2H_5$ | $CH_3$ |
| Cl | $CH_3$ | $C_3H_7$ | $CH_3$ |
| Cl | $CH_3$ | i-$C_3H_7$ | $CH_3$ |
| Cl | $CH_3$ | $C_4H_9$ | $CH_3$ |
| Cl | $CH_3$ | i-$C_4H_9$ | $CH_3$ |
| Cl | $CH_3$ | s-$C_4H_9$ | $CH_3$ |
| Cl | $CH_3$ | t-$C_4H_9$ | $CH_3$ |
| Cl | $CH_3$ | $C_2H_5$ | $C_2H_5$ |
| Cl | $CH_3$ | $C_3H_7$ | $C_3H_7$ |
| Cl | $CH_3$ | 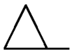 | $CH_3$ |
| Cl | $CH_3$ | 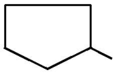 | $CH_3$ |
| Cl | $CH_3$ | 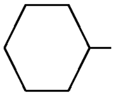 | $CH_3$ |
| $CH_3$ | Cl | $CH_3$ | H |
| $CH_3$ | Cl | $C_2H_5$ | H |
| $CH_3$ | Cl | $C_3H_7$ | H |
| $CH_3$ | Cl | i-$C_3H_7$ | H |
| $CH_3$ | Cl | $C_4H_9$ | H |
| $CH_3$ | Cl | i-$C_4H_9$ | H |
| $CH_3$ | Cl | s-$C_4H_9$ | H |
| $CH_3$ | Cl | t-$C_4H_9$ | H |
| $CH_3$ | Cl | $CH_3$ | $CH_3$ |
| $CH_3$ | Cl | $C_2H_5$ | $CH_3$ |
| $CH_3$ | Cl | $C_3H_7$ | $CH_3$ |
| $CH_3$ | Cl | i-$C_3H_7$ | $CH_3$ |
| $CH_3$ | Cl | $C_4H_9$ | $CH_3$ |
| $CH_3$ | Cl | i-$C_4H_9$ | $CH_3$ |
| $CH_3$ | Cl | s-$C_4H_9$ | $CH_3$ |
| $CH_3$ | Cl | t-$C_4H_9$ | $CH_3$ |
| $CH_3$ | Cl | $C_2H_5$ | $C_2H_5$ |
| $CH_3$ | Cl | $C_3H_7$ | $C_3H_7$ |
| $CH_3$ | Cl | 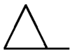 | $CH_3$ |
| $CH_3$ | Cl | 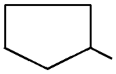 | $CH_3$ |

TABLE 6a-continued

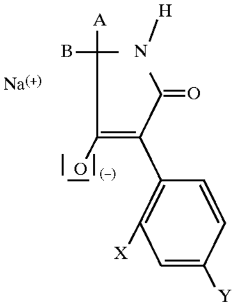

(If-a)

| X | Y | A | B |
|---|---|---|---|
| $CH_3$ | Cl | 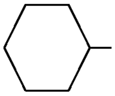 | $CH_3$ |
| Cl | $CH_3$ | $-(CH_2)_2-$ | |
| Cl | $CH_3$ | $-(CH_2)_4-$ | |
| Cl | $CH_3$ | $-(CH_2)_5-$ | |
| Cl | $CH_3$ | $-(CH_2)_6-$ | |
| Cl | $CH_3$ | $-(CH_2)_7-$ | |
| Cl | $CH_3$ | $-(CH_2)_2-O-(CH_2)_2-$ | |
| Cl | $CH_3$ | $-(CH_2)_2-S-(CH_2)_2-$ | |
| Cl | $CH_3$ | $-CH_2-CH-CH_3-(CH_2)_3-$ | |
| Cl | $CH_3$ | $-(CH_2)_2-CH-CH_3-(CH_2)_2-$ | |
| Cl | $CH_3$ | $-(CH_2)_2-CH-C_2H_5-(CH_2)_2-$ | |
| Cl | $CH_3$ | $-(CH_2)_2-CH-C_3H_7-(CH_2)_2-$ | |
| Cl | $CH_3$ | $-(CH_2)_2-$CH-i-$C_3H_7-(CH_2)_2-$ | |
| Cl | $CH_3$ | $-(CH_2)_2-CH-OCH_3-(CH_2)_2-$ | |
| Cl | $CH_3$ | $-(CH_2)_2-CH-OC_2H_5-(CH_2)_2-$ | |
| Cl | $CH_3$ | $-(CH_2)_2-CH-OC_3H_7-(CH_2)_2-$ | |
| Cl | $CH_3$ | $-(CH_2)_2-$CH-i-$OC_3H_7-(CH_2)_2-$ | |
| Cl | $CH_3$ | $-(CH_2)_2-C(CH_3)_2-(CH_2)_2-$ | |
| Cl | $CH_3$ | $-CH_2-(CH-CH_3)_2-(CH_2)_2-$ | |
| Cl | $CH_3$ | 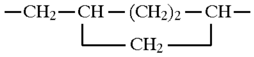 | |
| Cl | $CH_3$ | 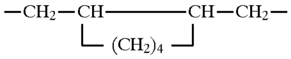 | |
| Cl | $CH_3$ | 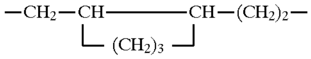 | |
| $CH_3$ | Cl | $-(CH_2)_2-$ | |
| $CH_3$ | Cl | $-(CH_2)_4-$ | |
| $CH_3$ | Cl | $-(CH_2)_5-$ | |
| $CH_3$ | Cl | $-(CH_2)_6-$ | |
| $CH_3$ | Cl | $-(CH_2)_7-$ | |
| $CH_3$ | Cl | $-(CH_2)_2-O-(CH_2)_2-$ | |
| $CH_3$ | Cl | $-(CH_2)_2-S-(CH_2)_2-$ | |
| $CH_3$ | Cl | $-CH_2-CHCH_3-(CH_2)_3-$ | |
| $CH_3$ | Cl | $-(CH_2)_2-CHCH_3-(CH_2)_2-$ | |
| $CH_3$ | Cl | $-(CH_2)_2-CHC_2H_5-(CH_2)_2-$ | |
| $CH_3$ | Cl | $-(CH_2)_2-CHC_3H_7-(CH_2)_2-$ | |
| $CH_3$ | Cl | $-(CH_2)_2-$CHi-$C_3H_7-(CH_2)_2-$ | |
| $CH_3$ | Cl | $-(CH_2)_2-CHOCH_3-(CH_2)_2-$ | |
| $CH_3$ | Cl | $-(CH_2)_2-CHOC_2H_5-(CH_2)_2-$ | |
| $CH_3$ | Cl | $-(CH_2)_2-CHOC_3H_7-(CH_2)_2-$ | |
| $CH_3$ | Cl | $-(CH_2)_2-$CHi-$OC_3H_7-(CH_2)_2-$ | |
| $CH_3$ | Cl | $-(CH_2)_2-C(CH_3)_2-(CH_2)_2-$ | |
| $CH_3$ | Cl | $-CH_2-(CHCH_3)_2-(CH_2)_2-$ | |
| $CH_3$ | Cl | 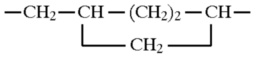 | |
| $CH_3$ | Cl | 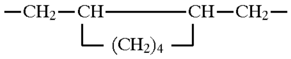 | |

TABLE 6a-continued

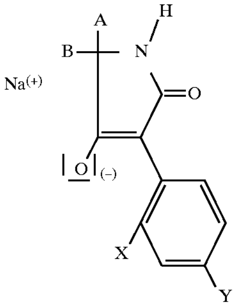

(If-a)

| X | Y | A | B |
|---|---|---|---|
| $CH_3$ | Cl | $-CH_2-CH\text{———}CH-(CH_2)_2-$ ($(CH_2)_3$ bridge) | |

The following compounds of the formula (If-b) may be mentioned individually in addition to the compounds mentioned in the preparation examples:

TABLE 6b

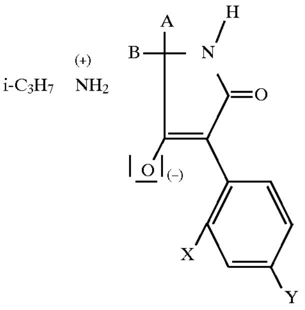

(If-b)

| X | Y | A | B |
|---|---|---|---|
| Cl | $CH_3$ | $CH_3$ | H |
| Cl | $CH_3$ | $C_2H_5$ | H |
| Cl | $CH_3$ | $C_3H_7$ | H |
| Cl | $CH_3$ | $i\text{-}C_3H_7$ | H |
| Cl | $CH_3$ | $C_4H_9$ | H |
| Cl | $CH_3$ | $i\text{-}C_4H_9$ | H |
| Cl | $CH_3$ | $s\text{-}C_4H_9$ | H |
| Cl | $CH_3$ | $t\text{-}C_4H_9$ | H |
| Cl | $CH_3$ | $CH_3$ | $CH_3$ |
| Cl | $CH_3$ | $C_2H_5$ | $CH_3$ |
| Cl | $CH_3$ | $C_3H_7$ | $CH_3$ |
| Cl | $CH_3$ | $i\text{-}C_3H_7$ | $CH_3$ |
| Cl | $CH_3$ | $C_4H_9$ | $CH_3$ |
| Cl | $CH_3$ | $i\text{-}C_4H_9$ | $CH_3$ |
| Cl | $CH_3$ | $s\text{-}C_4H_9$ | $CH_3$ |
| Cl | $CH_3$ | $t\text{-}C_4H_9$ | $CH_3$ |
| Cl | $CH_3$ | $C_2H_5$ | $C_2H_5$ |
| Cl | $CH_3$ | $C_3H_7$ | $C_3H_7$ |
| Cl | $CH_3$ | 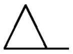 | $CH_3$ |
| Cl | $CH_3$ | 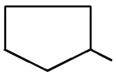 | $CH_3$ |
| Cl | $CH_3$ | 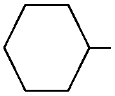 | $CH_3$ |
| $CH_3$ | Cl | $CH_3$ | H |

TABLE 6b-continued

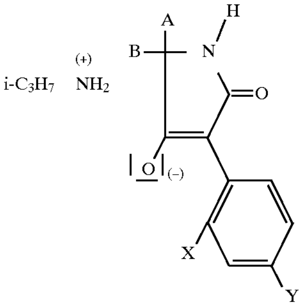

(If-b)

| X | Y | A | B |
|---|---|---|---|
| $CH_3$ | Cl | $C_2H_5$ | H |
| $CH_3$ | Cl | $C_3H_7$ | H |
| $CH_3$ | Cl | $i\text{-}C_3H_7$ | H |
| $CH_3$ | Cl | $C_4H_9$ | H |
| $CH_3$ | Cl | $i\text{-}C_4H_9$ | H |
| $CH_3$ | Cl | $s\text{-}C_4H_9$ | H |
| $CH_3$ | Cl | $t\text{-}C_4H_9$ | H |
| $CH_3$ | Cl | $CH_3$ | $CH_3$ |
| $CH_3$ | Cl | $C_2H_5$ | $CH_3$ |
| $CH_3$ | Cl | $C_3H_7$ | $CH_3$ |
| $CH_3$ | Cl | $i\text{-}C_3H_7$ | $CH_3$ |
| $CH_3$ | Cl | $C_4H_9$ | $CH_3$ |
| $CH_3$ | Cl | $i\text{-}C_4H_9$ | $CH_3$ |
| $CH_3$ | Cl | $s\text{-}C_4H_9$ | $CH_3$ |
| $CH_3$ | Cl | $t\text{-}C_4H_9$ | $CH_3$ |
| $CH_3$ | Cl | $C_2H_5$ | $C_2H_5$ |
| $CH_3$ | Cl | $C_3H_7$ | $C_3H_7$ |
| $CH_3$ | Cl | 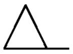 | $CH_3$ |
| $CH_3$ | Cl | 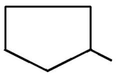 | $CH_3$ |
| $CH_3$ | Cl | 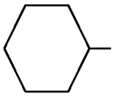 | $CH_3$ |
| Cl | $CH_3$ | $-(CH_2)_2-$ | |
| Cl | $CH_3$ | $-(CH_2)_4-$ | |
| Cl | $CH_3$ | $-(CH_2)_5-$ | |
| Cl | $CH_3$ | $-(CH_2)_6-$ | |
| Cl | $CH_3$ | $-(CH_2)_7-$ | |
| Cl | $CH_3$ | $-(CH_2)_2-O-(CH_2)_2-$ | |
| Cl | $CH_3$ | $-(CH_2)_2-S-(CH_2)_2-$ | |
| Cl | $CH_3$ | $-CH_2-CHCH_3-(CH_2)_3-$ | |
| Cl | $CH_3$ | $-(CH_2)_2-CHCH_3-(CH_2)_2-$ | |
| Cl | $CH_3$ | $-(CH_2)_2-CHC_2H_5-(CH_2)_2-$ | |
| Cl | $CH_3$ | $-(CH_2)_2-CHC_3H_7-(CH_2)_2-$ | |
| Cl | $CH_3$ | $-(CH_2)_2-CHi\text{-}C_3H_7-(CH_2)_2-$ | |
| Cl | $CH_3$ | $-(CH_2)_2-CHOCH_3-(CH_2)_2-$ | |
| Cl | $CH_3$ | $-(CH_2)_2-CHOC_2H_5-(CH_2)_2-$ | |
| Cl | $CH_3$ | $-(CH_2)_2-CHOC_3H_7-(CH_2)_2-$ | |
| Cl | $CH_3$ | $-(CH_2)_2-CHi\text{-}OC_3H_7-(CH_2)_2-$ | |
| Cl | $CH_3$ | $-(CH_2)_2-C(CH_3)_2-(CH_2)_2-$ | |
| Cl | $CH_3$ | $-CH_2-(CHCH_3)_2-(CH_2)_2-$ | |
| Cl | $CH_3$ | $-CH_2-CH-(CH_2)_2-CH-$ ($CH_2$ bridge) | |
| Cl | $CH_3$ | $-CH_2-CH\text{———}CH-CH_2-$ ($(CH_2)_4$ bridge) | |
| Cl | $CH_3$ | $-CH_2-CH\text{———}CH-(CH_2)_2-$ ($(CH_2)_3$ bridge) | |
| $CH_3$ | Cl | $-(CH_2)_2-$ | |

TABLE 6b-continued (If-b)

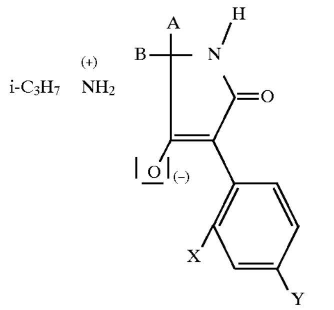

| X | Y | A | B |
|---|---|---|---|
| $CH_3$ | Cl | $-(CH_2)_4-$ | |
| $CH_3$ | Cl | $-(CH_2)_5-$ | |
| $CH_3$ | Cl | $-(CH_2)_6-$ | |
| $CH_3$ | Cl | $-(CH_2)_7-$ | |
| $CH_3$ | Cl | $-(CH_2)_2-O-(CH_2)_2$ | |
| $CH_3$ | Cl | $-(CH_2)_2-S-(CH_2)_2-$ | |
| $CH_3$ | Cl | $-CH_2-CHCH_3-(CH_2)_3-$ | |
| $CH_3$ | Cl | $-(CH_2)_2-CHCH_3-(CN2)_2-$ | |
| $CH_3$ | Cl | $-(CH_2)_2-CHC_2H_5-(CH_2)_2-$ | |
| $CH_3$ | Cl | $-(CH_2)_2-CHC_3H_7-(CH_2)_2-$ | |
| $CH_3$ | Cl | $-(CH_2)_2-CHi\text{-}C_3H_7-(CH_2)_2-$ | |
| $CH_3$ | Cl | $-(CH_2)_2-CHOCH_3-(CH_2)_2-$ | |
| $CH_3$ | Cl | $-(CH_2)_2-CHOC_2H_5-(CH_2)_2-$ | |
| $CH_3$ | Cl | $-(CH_2)_2-CHOC_3H_7-(CH_2)_2-$ | |
| $CH_3$ | Cl | $-(CH_2)_2-CHi\text{-}OC_3H_7-(CH_2)_2-$ | |
| $CH_3$ | Cl | $-(CH_2)_2-C(CH_3)_2-(CH_2)_2-$ | |
| $CH_3$ | Cl | $-CH_2-(CHCH_3)_2-(CH_2)_2-$ | |
| $CH_3$ | Cl | 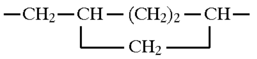 | |
| $CH_3$ | Cl | 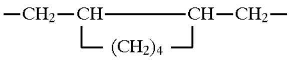 | |
| $CH_3$ | Cl | 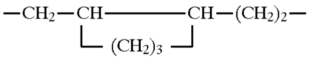 | |

The following compounds of the formula (Ig-a) may be mentioned individually in addition to the compounds mentioned in the preparation examples:

TABLE 7a (Ig-a)

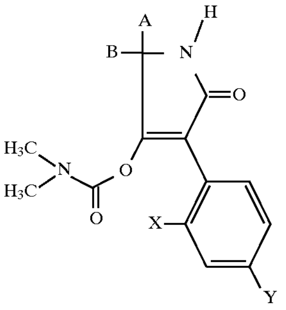

| X | Y | A | B |
|---|---|---|---|
| Cl | $CH_3$ | $CH_3$ | H |
| Cl | $CH_3$ | $C_2H_4$ | H |
| Cl | $CH_3$ | $C_3H_7$ | H |
| Cl | $CH_3$ | $i\text{-}C_3H_7$ | H |
| Cl | $CH_3$ | $C_4H_9$ | H |
| Cl | $CH_3$ | $i\text{-}C_4H_9$ | H |
| Cl | $CH_3$ | $s\text{-}C_4H_9$ | H |
| Cl | $CH_3$ | $t\text{-}C_4H_9$ | H |

TABLE 7a-continued (Ig-a)

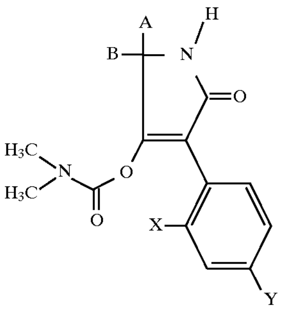

| X | Y | A | B |
|---|---|---|---|
| Cl | $CH_3$ | $CH_3$ | $CH_3$ |
| Cl | $CH_3$ | $C_2H_5$ | $CH_3$ |
| Cl | $CH_3$ | $C_3H_7$ | $CH_3$ |
| Cl | $CH_3$ | $i\text{-}C_3H_7$ | $CH_3$ |
| Cl | $CH_3$ | $C_4H_9$ | $CH_3$ |
| Cl | $CH_3$ | $i\text{-}C_4H_9$ | $CH_3$ |
| Cl | $CH_3$ | $s\text{-}C_4H_9$ | $CH_3$ |
| Cl | $CH_3$ | $t\text{-}C_4H_9$ | $CH_3$ |
| Cl | $CH_3$ | $C_2H_5$ | $C_2H_5$ |
| Cl | $CH_3$ | $C_3H_7$ | $C_3H_7$ |
| Cl | $CH_3$ | 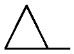 | $CH_3$ |
| Cl | $CH_3$ | 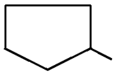 | $CH_3$ |
| Cl | $CH_3$ | 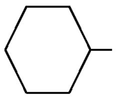 | $CH_3$ |
| $CH_3$ | Cl | $CH_3$ | H |
| $CH_3$ | Cl | $C_2H_5$ | H |
| $CH_3$ | Cl | $C_3H_7$ | H |
| $CH_3$ | Cl | $i\text{-}C_3H_7$ | H |
| $CH_3$ | Cl | $C_4H_9$ | H |
| $CH_3$ | Cl | $i\text{-}C_4H_9$ | H |
| $CH_3$ | Cl | $s\text{-}C_4H_9$ | H |
| $CH_3$ | Cl | $t\text{-}C_4H_9$ | H |
| $CH_3$ | Cl | $CH_3$ | $CH_3$ |
| $CH_3$ | Cl | $C_2H_5$ | $CH_3$ |
| $CH_3$ | Cl | $C_3H_7$ | $CH_3$ |
| $CH_3$ | Cl | $i\text{-}C_3H_7$ | $CH_3$ |
| $CH_3$ | Cl | $C_4H_9$ | $CH_3$ |
| $CH_3$ | Cl | $i\text{-}C_4H_9$ | $CH_3$ |
| $CH_3$ | Cl | $s\text{-}C_4H_9$ | $CH_3$ |
| $CH_3$ | Cl | $t\text{-}C_4H_9$ | $CH_3$ |
| $CH_3$ | Cl | $C_2H_5$ | $C_2H_5$ |
| $CH_3$ | Cl | $C_3H_7$ | $C_3H_7$ |
| $CH_3$ | Cl | 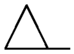 | $CH_3$ |
| $CH_3$ | Cl | 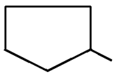 | $CH_3$ |
| $CH_3$ | Cl | 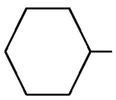 | $CH_3$ |
| Cl | $CH_3$ | $-(CH_2)_2-$ | |
| Cl | $CH_3$ | $-(CH_2)_4-$ | |
| Cl | $CH_3$ | $-(CH_2)_5-$ | |
| Cl | $CH_3$ | $-(CH_2)_6-$ | |
| Cl | $CH_3$ | $-(CH_2)_7-$ | |
| Cl | $CH_3$ | $-(CH_2)_2-O-(CH_2)_2-$ | |

TABLE 7a-continued

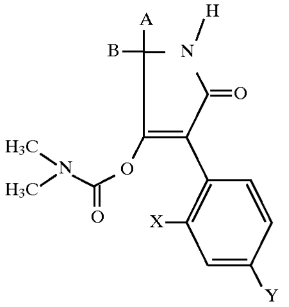

(Ig-a)

| X | Y | A | B |
|---|---|---|---|
| Cl | $CH_3$ | | $-(CH_2)_2-S-(CH_2)_2-$ |
| Cl | $CH_3$ | | $-CH_2-CHCH_3-(CH_2)_3-$ |
| Cl | $CH_3$ | | $-(CH_2)_2-CHCH_3-(CH_2)_2-$ |
| Cl | $CH_3$ | | $-(CH_2)_2-CHC_2H_5-(CH_2)_2-$ |
| Cl | $CH_3$ | | $-(CH_2)_2-CHC_3H_7-(CH_2)_2-$ |
| Cl | $CH_3$ | | $-(CH_2)_2-CHi\text{-}C_3H_7-(CH_2)_2-$ |
| Cl | $CH_3$ | | $-(CH_2)_2-CHOCH_3-(CH_2)_2-$ |
| Cl | $CH_3$ | | $-(CH_2)_2-CHOC_2H_5-(CH_2)_2-$ |
| Cl | $CH_3$ | | $-(CH_2)_2-CHOC_3H_7-(CH_2)_2-$ |
| Cl | $CH_3$ | | $-(CH_2)_2-CHi\text{-}OC_3H_7-(CH_2)_2-$ |
| Cl | $CH_3$ | | $-(CH_2)_2-C(CH_3)_2-(CH_2)_2-$ |
| Cl | $CH_3$ | | $-CH_2-(CHCH_3)_2-(CH_2)_2-$ |
| Cl | $CH_3$ | | $-CH_2-CH-(CH_2)_2-CH-$<br>$CH_2$ |
| Cl | $CH_3$ | | $-CH_2-CH-CH-CH_2-$<br>$(CH_2)_4$ |
| Cl | $CH_3$ | | $-CH_2-CH-CH-(CH_2)_2-$<br>$(CH_2)_3$ |
| $CH_3$ | Cl | | $-(CH_2)_2-$ |
| $CH_3$ | Cl | | $-(CH_2)_4-$ |
| $CH_3$ | Cl | | $-(CH_2)_5-$ |
| $CH_3$ | Cl | | $-(CH_2)_6-$ |
| $CH_3$ | Cl | | $-(CH_2)_7-$ |
| $CH_3$ | Cl | | $-(CH_2)_2-O-(CH_2)_2-$ |
| $CH_3$ | Cl | | $-(CH_2)_2-S-(CH_2)_2-$ |
| $CH_3$ | Cl | | $-CH_2-CHCH_3-(CH_2)_3-$ |
| $CH_3$ | Cl | | $-(CH_2)_2-CHCH_3-(CH_2)_2-$ |
| $CH_3$ | Cl | | $-(CH_2)_2-CHC_2H_5-(CH_2)_2-$ |
| $CH_3$ | Cl | | $-(CH_2)_2-CHC_3H_7-(CH_2)_2-$ |
| $CH_3$ | Cl | | $-(CH_2)_2-CHi\text{-}C_3H_7-(CH_2)_2-$ |
| $CH_3$ | Cl | | $-(CH_2)_2-CHOCH_3-(CH_2)_2-$ |
| $CH_3$ | Cl | | $-(CH_2)_2-CHOC_2H_5-(CH_2)_2-$ |
| $CH_3$ | Cl | | $-(CH_2)_2-CHOC_3H_7-(CH_2)_2-$ |
| $CH_3$ | Cl | | $-(CH_2)_2-CHi\text{-}OC_3H_7-(CH_2)_2-$ |
| $CH_3$ | Cl | | $(CH_2)_2-C(CH_3)_2-(CH_2)_2-$ |
| $CH_3$ | Cl | | $-CH_2-(CHCH_3)_2-(CH_2)_2-$ |
| $CH_3$ | Cl | | $-CH_2-CH-(CH_2)_2-CH-$<br>$CH_2$ |
| $CH_3$ | Cl | | $-CH_2-CH-CH-CH_2-$<br>$(CH_2)_4$ |
| $CH_3$ | Cl | | $-CH_2-CH-CH-(CH_2)_2-$<br>$(CH_2)_3$ |

The following compounds of the formula (Ig-b) may be mentioned individually in addition to the compounds mentioned in the preparation examples:

TABLE 7b

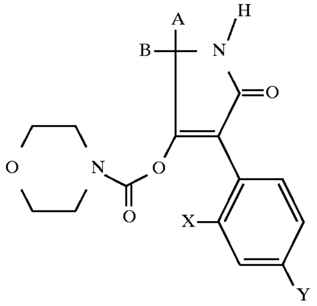

(Ig-b)

| X | Y | A | B |
|---|---|---|---|
| Cl | $CH_3$ | $CH_3$ | H |
| Cl | $CH_3$ | $C_2H_5$ | H |
| Cl | $CH_3$ | $C_3H_7$ | H |
| Cl | $CH_3$ | $i\text{-}C_3H_7$ | H |
| Cl | $CH_3$ | $C_4H_9$ | H |
| Cl | $CH_3$ | $i\text{-}C_4H_9$ | H |
| Cl | $CH_3$ | $s\text{-}C_4H_9$ | H |
| Cl | $CH_3$ | $t\text{-}C_4H_9$ | H |
| Cl | $CH_3$ | $CH_3$ | $CH_3$ |
| Cl | $CH_3$ | $C_2H_5$ | $CH_3$ |
| Cl | $CH_3$ | $C_3H_7$ | $CH_3$ |
| Cl | $CH_3$ | $i\text{-}C_3H_7$ | $CH_3$ |
| Cl | $CH_3$ | $C_4H_9$ | $CH_3$ |
| Cl | $CH_3$ | $i\text{-}C_4H_9$ | $CH_3$ |
| Cl | $CH_3$ | $s\text{-}C_4H_9$ | $CH_3$ |
| Cl | $CH_3$ | $t\text{-}C_4H_9$ | $CH_3$ |
| Cl | $CH_3$ | $C_2H_5$ | $C_2H_5$ |
| Cl | $CH_3$ | $C_3H_7$ | $C_3H_7$ |
| Cl | $CH_3$ | 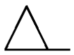 | $CH_3$ |
| Cl | $CH_3$ | 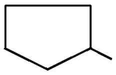 | $CH_3$ |
| Cl | $CH_3$ | 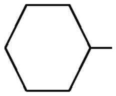 | $CH_3$ |
| $CH_3$ | Cl | $CH_3$ | H |
| $CH_3$ | Cl | $C_2H_5$ | H |
| $CH_3$ | Cl | $C_3H_7$ | H |
| $CH_3$ | Cl | $i\text{-}C_3H_7$ | H |
| $CH_3$ | Cl | $C_4H_9$ | H |
| $CH_3$ | Cl | $i\text{-}C_4H_9$ | H |
| $CH_3$ | Cl | $s\text{-}C_4H_9$ | H |
| $CH_3$ | Cl | $t\text{-}C_4H_9$ | H |
| $CH_3$ | Cl | $CH_3$ | $CH_3$ |
| $CH_3$ | Cl | $C_2H_5$ | $CH_3$ |
| $CH_3$ | Cl | $C_3H_7$ | $CH_3$ |
| $CH_3$ | Cl | $i\text{-}C_3H_7$ | $CH_3$ |
| $CH_3$ | Cl | $C_4H_9$ | $CH_3$ |
| $CH_3$ | Cl | $i\text{-}C_4H_9$ | $CH_3$ |
| $CH_3$ | Cl | $s\text{-}C_4H_9$ | $CH_3$ |
| $CH_3$ | Cl | $t\text{-}C_4H_9$ | $CH_3$ |
| $CH_3$ | Cl | $C_2H_5$ | $C_2H_5$ |
| $CH_3$ | Cl | $C_3H_7$ | $C_3H_7$ |
| $CH_3$ | Cl | 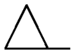 | $CH_3$ |
| $CH_3$ | Cl | 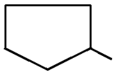 | $CH_3$ |

TABLE 7b-continued

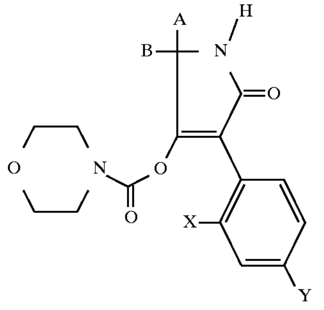

(Ig-b)

| X | Y | A | B |
|---|---|---|---|
| $CH_3$ | Cl | 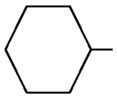 | $CH_3$ |
| Cl | $CH_3$ | $-(CH_2)_2-$ | |
| Cl | $CH_3$ | $-(CH_2)_4-$ | |
| Cl | $CH_3$ | $-(CH_2)_5-$ | |
| Cl | $CH_3$ | $-(CH_2)_6-$ | |
| Cl | $CH_3$ | $-(CH_2)_7-$ | |
| Cl | $CH_3$ | $-(CH_2)_2-O-(CH_2)_2-$ | |
| Cl | $CH_3$ | $-(CH_2)_2-S-(CH_2)_2-$ | |
| Cl | $CH_3$ | $-CH_2-CHCH_3-(CH_2)_3-$ | |
| Cl | $CH_3$ | $-(CH_2)_2-CHCH_3-(CH_2)_2-$ | |
| Cl | $CH_3$ | $-(CH_2)_2-CHC_2H_5-(CH_2)_2-$ | |
| Cl | $CH_3$ | $-(CH_2)_2-CHC_3H_7-(CH_2)_2-$ | |
| Cl | $CH_3$ | $-(CH_2)_2-CHi\text{-}C_3H_7-(CH_2)_2-$ | |
| Cl | $CH_3$ | $-(CH_2)_2-CHOCH_3-(CH_2)_2-$ | |
| Cl | $CH_3$ | $-(CH_2)_2-CHOC_2H_5-(CH_2)_2-$ | |
| Cl | $CH_3$ | $-(CH_2)_2-CHOC_3H_7-(CH_2)_2-$ | |
| Cl | $CH_3$ | $-(CH_2)_2-CHi\text{-}OC_3H_7-(CH_2)_2-$ | |
| Cl | $CH_3$ | $-(CH_2)_2-C(CH_3)_2-(CH_2)_2-$ | |
| Cl | $CH_3$ | $-CH_2-(CHCH_3)_2-(CH_2)_2-$ | |
| Cl | $CH_3$ | 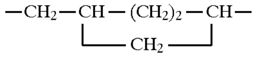 | |
| Cl | $CH_3$ | 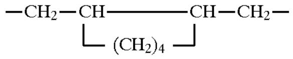 | |
| Cl | $CH_3$ | 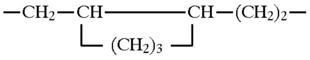 | |
| $CH_3$ | Cl | $-(CH_2)_2-$ | |
| $CH_3$ | Cl | $-(CH_2)_4-$ | |
| $CH_3$ | Cl | $-(CH_2)_5-$ | |
| $CH_3$ | Cl | $-(CH_2)_6-$ | |
| $CH_3$ | Cl | $-(CH_2)_7-$ | |
| $CH_3$ | Cl | $-(CH_2)_2-O-(CH_2)_2-$ | |
| $CH_3$ | Cl | $-(CH_2)_2-S-(CH_2)_2-$ | |
| $CH_3$ | Cl | $-CH_2-CHCH_3-(CH_2)_3-$ | |
| $CH_3$ | Cl | $-(CH_2)_2-CHCH_3-(CH_2)_2-$ | |
| $CH_3$ | Cl | $-(CH_2)_2-CHC_2H_5-(CH_2)_2-$ | |
| $CH_3$ | Cl | $-(CH_2)_2-CHC_3H_7-(CH_2)_2-$ | |
| $CH_3$ | Cl | $-(CH_2)_2-CHi\text{-}C_3H_7-(CH_2)_2-$ | |
| $CH_3$ | Cl | $-(CH_2)_2-CHOCH_3-(CH_2)_2-$ | |
| $CH_3$ | Cl | $-(CH_2)_2-CHOC_2H_5-(CH_2)_2-$ | |
| $CH_3$ | Cl | $-(CH_2)_2-CHOC_3H_7-(CH_2)_2-$ | |
| $CH_3$ | Cl | $-(CH_2)_2-CHi\text{-}OC_3H_7-(CH_2)_2-$ | |
| $CH_3$ | Cl | $-(CH_2)_2-C(CH_3)_2-(CH_2)_2-$ | |
| $CH_3$ | Cl | $-CH_2-(CHCH_3)_2-(CH_2)_2-$ | |
| $CH_3$ | Cl | 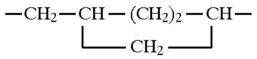 | |
| $CH_3$ | Cl | 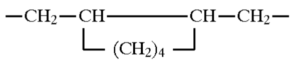 | |

TABLE 7b-continued

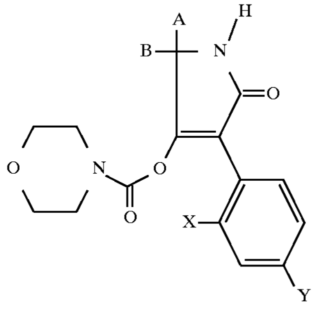

(Ig-b)

| X | Y | A | B |
|---|---|---|---|
| $CH_3$ | Cl | 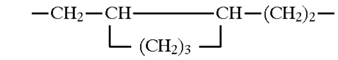 | |

If, in accordance with process (A) ethyl N-(2-chloro-4-methylphenylacetyl)-1-amino-4-ethyl-cyclohexane-carboxylate is used as starting substance, the course of the process according to the invention can be represented by the following equation:

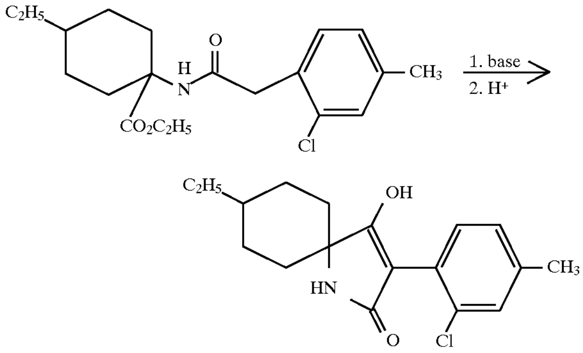

If, in accordance with process (Bα), 3-(2-methyl-4-chlorophenyl)-5,5-dimethyl-pyrrolidine-2,4-dione and pivaloyl chloride are used as starting substances, the course of the process according to the invention can be represented by the following equation:

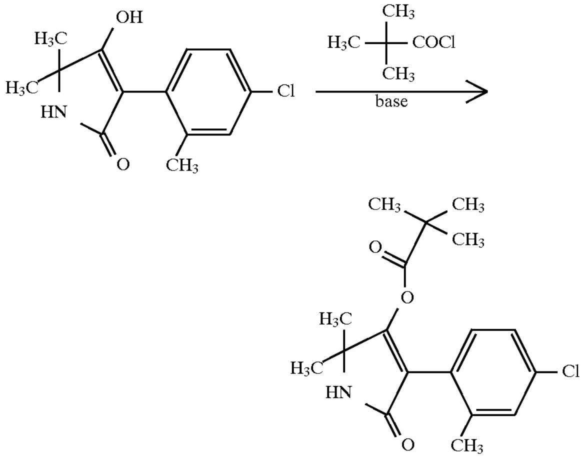

If, in accordance with process (Bβ), 3-(2-bromo-4-ethylphenyl)-5-isopropyl-5-methyl-pyrrolidine-2,4-dione and acetic anhydride are used as starting compounds, the course of the process according to the invention can be represented by the following equation:

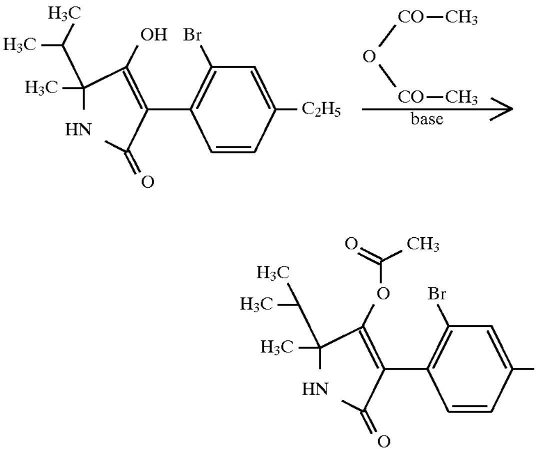

If, in accordance with process (C), 3-(2-methyl-4-chlorophenyl)-5,5-diethyl-pyrrolidine-2,4-dione and ethoxyethyl chloroformate are used as starting compounds, the course of the process according to the invention can be represented by the following equation:

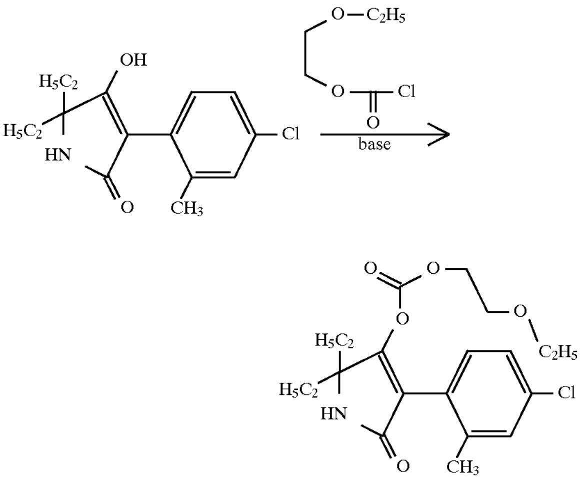

If, in accordance with process (Dα), 3-(2-chloro-4-methylphenyl)-5,5-pentamethylene-pyrrolidine-2,4-dione and methyl chloromonothioformate are used as starting materials, the course of the reaction can be represented as follows:

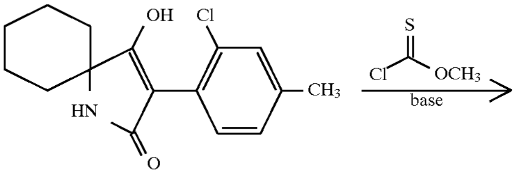

-continued

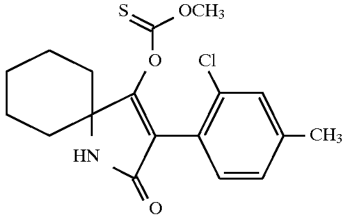

If, in accordance with process (Dβ), 3-(2-bromo-4-ethylphenyl)-5,5-ethylmercaptoethyl-pyrrolidine-2,4-dione, carbon disulfide and methyl iodide are used as starting materials, the course of the reaction can be represented as follows:

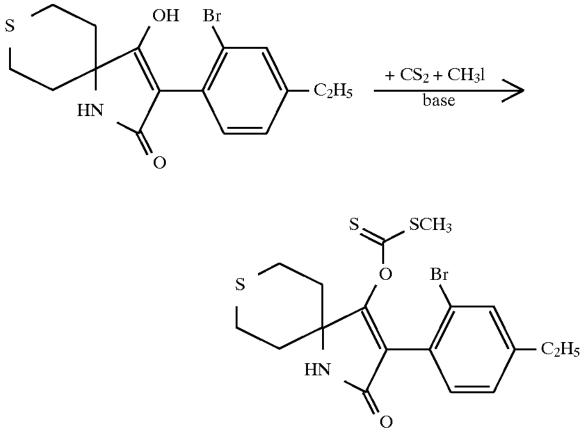

If, in accordance with process (E), 3-(2-chloro-4-isopropylphenyl)-5,5-(2-methyl)-pentamethylene-pyrrolidine-2,4-dione and methanesulfonyl chloride are used as starting materials, the course of the reaction can be represented by the following equation:

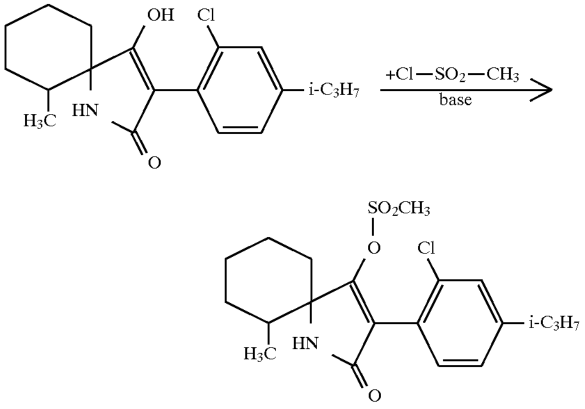

If, in accordance with process (F), 3-(2-methyl-4-chlorophenyl)-5-isobutyl-5-methyl-pyrrolidine-2,4-dione and 2,2,2-trifluoroethyl methanethio-phosphonate are used as starting materials, the course of the reaction can be represented by the following equation:

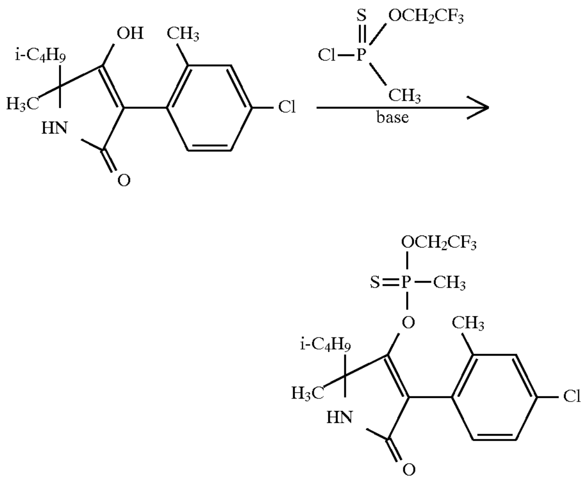

If, in accordance with process (G), 3-(2-fluoro-4-methylphenyl)-5-cyclopropyl-5-methyl-pyrrolidine-2,4-dione and NaOH are used as reactants, the course of the process according to the invention can be represented by the following equation:

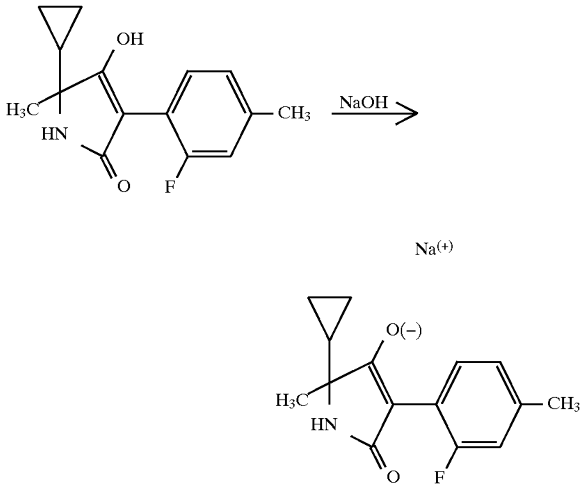

If, in accordance with process (Hα), 3-(2-chloro-4-ethylphenyl)-5,5-hexamethylene-pyrrolidine-2,4-dione and ethyl isocyanate are used as starting materials, the course of the reaction can be represented by the following equation:

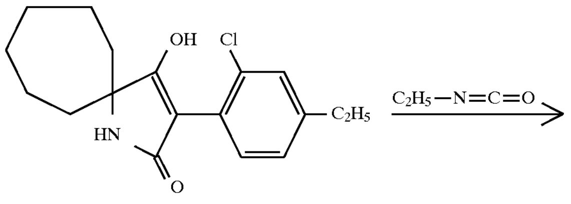

-continued

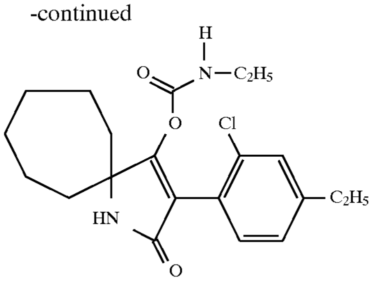

If, in accordance with process (Hβ), 3-(2-methyl-4-chlorophenyl)-5-methyl-pyrrolidine-2,4-dione and dimethylcarbamoyl chloride are used as starting materials, the course of the reaction can be represented by the following equation:

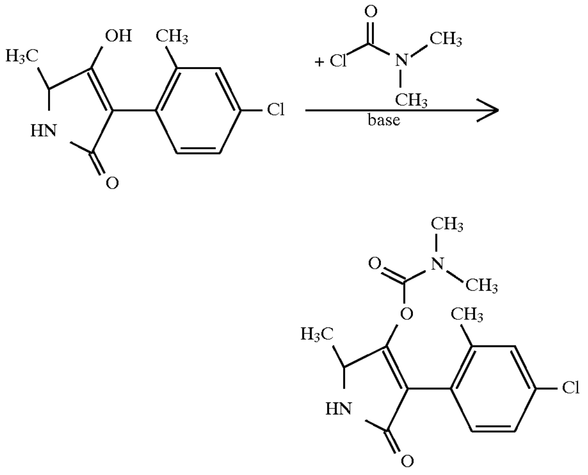

The compounds of the formula (II)

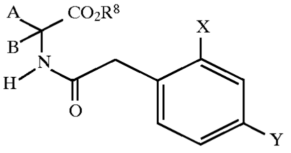

(II)

in which

A, B, X, Y and $R^8$ have the abovementioned meanings which are required as starting substances in process (A) according to the invention, are new.

Acyl-amino acid esters of the formula (II) are obtained, for example, when amino acid derivatives of the formula (XIV)

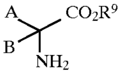

(XIV)

in which $R^9$ represents hydrogen (XIVa) or alkyl, preferably $C_1$–$C_6$-alkyl (XIVb) and A and B have the abovementioned meanings, are acylated with phenylacetyl halides of the formula (XV)

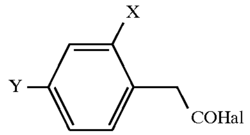

(XV)

in which

X and Y have the abovementioned meanings and

Hal represents chlorine or bromine, (Chem. Reviews 52, 237–416 (1953); Bhattacharya, Indian J. Chem. 6, 341–5, 1968), and the acylamino acids of the formula (IIa)

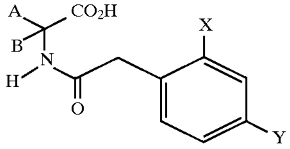

(IIa)

in which

A, B, X and Y have the abovementioned meanings which are obtained if $R^9$=hydrogen are esterified (Chem. Ind. (London) 1568 (1968)).

The substituted cyclic aminocarboxylic acids of the formula (XIVa) are generally accessible via the Bucherer-Bergs synthesis or by the Strecker synthesis and are obtained in each case in various isomeric forms. The conditions of the Bucherer-Bergs synthesis, for example, predominantly yield the isomers (for the sake of simplicity hereinbelow termed β) in which the radicals R and the carboxyl group are in the equatorial position, while the conditions of the Strecker synthesis predominantly give the isomers (for the sake of simplicity hereinbelow termed α) in which the amino group and the radicals R are in the equatorial position.

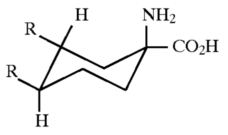

Bucherer-Bergs synthesis
(β isomer)

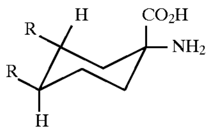

Strecker synthesis
(α isomer)

(L. Munday, J. Chem. Soc. 4372 (1961); J. T. Eward, C. Jitrangeri, Can. J. Chem. 53, 3339 (1975).

Furthermore, the starting substances of the formula (II)

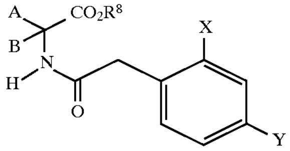

(II)

in which

A, B, X, Y and $R^8$ have the abovementioned meanings, which are used in the above process (A) can be prepared by reacting aminonitriles of the formula (XVI)

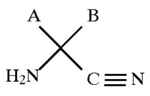

(XVI)

in which

A and B have the abovementioned meanings, with phenylacetyl halides of the formula (XV)

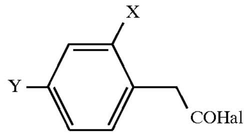

(XV)

in which

X and Y have the abovementioned meanings and

Hal represents chlorine or bromine, to give compounds of the formula (XVII)

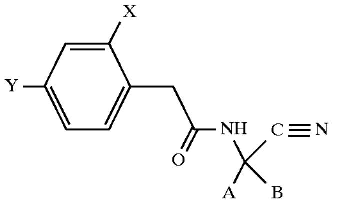

(XVII)

in which

A, B, X and Y have the abovementioned meanings, and these are subsequently subjected to alcoholysis in the presence of sulfuric acid.

The compounds of the formula (XVII) are also new.

In addition to the intermediates mentioned in the preparation examples, the following compounds of the formula (II) may be mentioned by way of example, but not by limitation:

N-(2-chloro-4-methylphenylacetyl)-alanine methyl ester

N-(2-chloro-4-methylphenylacetyl)-leucine methyl ester

N-(2-chloro-4-methylphenylacetyl)-isoleucine methyl ester

N-(2-chloro-4-methylphenylacetyl)-valine methyl ester methyl N-(2-chloro-4-methylphenylacetyl)-aminoisobutyrate methyl N-(2-chloro-4-methylphenylacetyl)-2-ethyl-2-aminobutyrate methyl N-(2-chloro-4-methylphenylacetyl)-2-methyl-2-aminovalerate methyl N-(2-chloro-4-methylphenylacetyl)-2,3-dimethyl-2-aminovalerate methyl N-(2-chloro-4-methylphenylacetyl)-1-amino-cyclopentanecarboxylate methyl N-(2-chloro-4-methylphenylacetyl)-1-amino-cyclohexanecarboxylate methyl N-(2-chloro-4-methylphenylacetyl)-1-amino-cycloheptanecarboxylate methyl N-(2-chloro-4-methylphenylacetyl)-1-amino-cyclooctanecarboxylate N-(4-chloro-2-methylphenylacetyl)-alanine methyl ester N-(4-chloro-2-methylphenylacetyl)-leucine methyl ester N-(4-chloro-2-methylphenylacetyl)-isoleucine methyl ester N-(4-chloro-2-methylphenylacetyl)-valine methyl ester methyl N-(4-chloro-2-methylphenylacetyl)-aminoisobutyrate methyl N-(4-chloro-2-methylphenylacetyl)-2-ethyl-2-aminobutyrate methyl N-(4-chloro-2-methylphenylacetyl)-2-methyl-2-aminovalerate methyl N-(4-chloro-2-methylphenylacetyl)-2,3-dimethyl-2-aminovalerate methyl N-(4-chloro-2-methylphenylacetyl)-1-amino-cyclopentanecarboxylate methyl N-(4-chloro-2-methylphenylacetyl)-1-amino-cyclohexanecarboxylate methyl N-(4-chloro-2-methylphenylacetyl)-1-amino-cycloheptanecarboxylate methyl N-(4-chloro-2-methylphenylacetyl)-1-amino-cyclooctanecarboxylate methyl N-(2-chloro-4-methyl-phenylacetyl)-1-amino-2-methyl-cyclohexanecarboxylate, methyl N-(2-chloro-4-methyl-phenylacetyl)-1-amino-3-methyl-cyclohexanecarboxylate, methyl N-(2-chloro-4-methyl-phenylacetyl)-1-amino-4-methyl-cyclohexanecarboxylate, methyl N-(2-chloro-4-methyl-phenylacetyl)-1-amino-3,4-dimethyl-cyclohexanecarboxylate, methyl N-(2-chloro-4-methyl-phenylacetyl)-1-amino-4-ethyl-cyclohexanecarboxylate, methyl N-(2-chloro-4-methyl-phenylacetyl)-1-amino-4-isopropyl-cyclohexanecarboxylate, methyl N-(2-chloro-4-methyl-phenylacetyl)-1-amino-4-tertbutyl-cyclohexanecarboxylate, methyl N-(2-chloro-4-methyl-phenylacetyl)-1-amino-4-methoxy-cyclohexanecarboxylate, methyl N-(4-chloro-2-methyl-phenylacetyl)-1-amino-2-methyl-cyclohexanecarboxylate, methyl N-(4-chloro-2-methyl-phenylacetyl)-1-amino-3-methyl-cyclohexanecarboxylate, methyl N-(4-chloro-2-methyl-phenylacetyl)-1-amino-4-methyl-cyclohexanecarboxylate, methyl N-(4-chloro-2-methyl-phenylacetyl)-1-amino-3,4-dimethyl-cyclohexanecarboxylate, methyl N-(4-chloro-2-methyl-phenylacetyl)-1-amino-4-ethyl-cyclohexanecarboxylate, methyl N-(4-chloro-2-methyl-phenylacetyl)-1-amino-4-isopropyl-cyclohexanecarboxylate, methyl N-(4-chloro-2-methyl-phenylacetyl)-1-amino-4-tertbutyl-cyclohexanecarboxylate, methyl N-(4-chloro-2-methyl-phenylacetyl)-1-amino-4-methoxy-cyclohexanecarboxylate.

In addition to the intermediates mentioned in the preparation examples, the following compounds of the formula (IIa) may be mentioned by way of example but not by limitation:

N-(2-chloro-4-methylphenylacetyl)-alanine

N-(2-chloro-4-methylphenylacetyl)-leucine

N-(2-chloro-4-methylphenylacetyl)-isoleucine

N-(2-chloro-4-methylphenylacetyl)-valine

N-(2-chloro-4-methylphenylacetyl)-aminoisobutyric acid

N-(2-chloro-4-methylphenylacetyl)-2-ethyl-2-aminobutyric acid

N-(2-chloro-4-methylphenylacetyl)-2-methyl-2-aminovaleric acid

N-(2-chloro-4-methylphenylacetyl)-2,3-dimethyl-2-aminovaleric acid

N-(2-chloro-4-methylphenylacetyl)-1-amino-cyclopentanecarboxylic acid

N-(2-chloro-4-methylphenylacetyl)-1-amino-cyclohexanecarboxylic acid

N-(2-chloro-4-methylphenylacetyl)-1-amino-cycloheptanecarboxylic acid

N-(2-chloro-4-methylphenylacetyl)-1-amino-cycldoctanecarboxylic acid

N-(4-chloro-2-methylphenylacetyl)-alanine

N-(4-chloro-2-methylphenylacetyl)-leucine

N-(4-chloro-2-methylphenylacetyl)-isoleucine

N-(4-chloro-2-methylphenylacetyl)-valine

N-(4-chloro-2-methylphenylacetyl)-aminoisobutyric acid

N-(4-chloro-2-methylphenylacetyl)-2-ethyl-2-aminobutyric acid

N-(4-chloro-2-methylphenylacetyl)-2-methyl-2-aminovaleric acid

N-(4-chloro-2-methylphenylacetyl)-2,3-dimethyl-2-aminovaleric acid

N-(4-chloro-2-methylphenylacetyl)-1-amino-cyclopentanecarboxylic acid

N-(4-chloro-2-methylphenylacetyl)-1-amino-cyclohexanecarboxylic acid

N-(4-chloro-2-methylphenylacetyl)-1-amino-cycloheptanecarboxylic acid

N-(4-chloro-2-methylphenylacetyl)-1-amino-cyclooctanecarboxylic acid

N-(2-chloro-4-methyl-phenylacetyl)-1-amino-2-methyl-cyclohexanecarboxylic acid

N-(2-chloro-4-methyl-phenylacetyl)-1-amino-3-methyl-cyclohexanecarboxylic acid

N-(2-chloro-4-methyl-phenylacetyl)-1-amino-4-methyl-cyclohexanecarboxylic acid

N-(2-chloro-4-methyl-phenylacetyl)-1-amino-3,4-dimethyl-cyclohexanecarboxylic acid N-(2-chloro-4-methyl-phenylacetyl)-1-amino-4-ethyl-cyclohexanecarboxylic acid N-(2-chloro-4-methyl-phenylacetyl)-1-amino-4-isopropylcyclohexanecarboxylic acid N-(2-chloro-4-methyl-phenylacetyl)-1-amino-4-tert-butylcyclohexanecarboxylic acid N-(2-chloro-4-methyl-phenylacetyl)-1-amino-4-methoxy-cyclohexanecarboxylic acid N-(4-chloro-2-methyl-phenylacetyl)-1-amino-2-methylcyclohexanecarboxylic acid N-(4-chloro-2-methyl-phenylacetyl)-1-amino-3-methyl-cyclohexanecarboxylic acid N-(4-chloro-2-methyl-phenylacetyl)-1-amino-4-methyl-cyclohexanecarboxylic acid N-(4-chloro-2-methyl-phenylacetyl)-1-amino-3,4-dimethylcyclohexanecarboxylic acid N-(4-chloro-2-methyl-phenylacetyl)-1-amino-4-ethyl-cyclohexanecarboxylic acid N-(4-chloro-2-methyl-phenylacetyl)-1-amino-4-isopropylcyclohexanecarboxylic acid N-(4-chloro-2-methyl-phenylacetyl)-1-amino-4-tert-butylcyclohexanecarboxylic acid N-(4-chloro-2-methyl-phenylacetyl)-1-amino-4-methoxy-cyclohexanecarboxylic acid Compounds of the formula (IIa) can be obtained, for example, from the phenylacetyl halides of the formula (XV) and amino acids of the formula (XIVa) by the method of Schotten-Baumann (Organikum [Laboratory Practical in Organic Chemistry], 9th Edition, 446 (1970) VEB Deutscher Verlag der Wissenschaften, Berlin).

The phenylacetyl halides of the formula (XV) are generally known compounds of organic chemistry or can be prepared by known processes.

The compounds of the formula (Ia), which are required as starting substances for carrying out processes (B), (C), (D), (E), (F), (G) and (H) according to the invention, can be obtained by process (A) according to the invention.

The acid halides of the formula (III), carboxylic anhydrides of the formula (IV), chloroformic esters or chloroformic thioesters of the formula (V), chloromonothioformic esters or chlorodithioformic esters of the formula (VI), alkyl halides of the formula (VII), sulfonyl chlorides of the formula (VIII), phosphorus compounds of the formula (IX), metal hydroxides, metal alkoxides or amines of the formulae (X) and (XI) and isocyanates of the formula (XII) or carbamoyl chloride of the formula (XIII), which are furthermore required as starting substances for carrying out processes (B), (C), (D), (E), (F), (G) and (H) according to the invention, are generally known compounds of organic or inorganic chemistry.

Process (A) comprises a process wherein compounds of the formula (II) in which A, B, X, Y and $R^8$ have the abovementioned meanings are subjected to an intramolecular condensation reaction in the presence of bases.

Diluents which can be employed in process (A) according to the invention are all inert organic solvents. The following can preferably be used: hydrocarbons, such as toluene and xylene, furthermore ethers, such as dibutyl ether, tetrahydrofuran, dioxane, glycol dimethyl ether and diglycol dimethyl ether, in addition polar solvents, such as dimethyl sulfoxide, sulfolane, dimethylformamide and N-methylpyrrolidone, and also alcohols such as methanol, ethanol, propanol, isopropanol, butanol, isobutanol and tert-butanol.

Bases (deprotonating agents) which can be employed when carrying out process (A) according to the invention are all customary proton acceptors. The following can preferably be used: the oxides, hydroxides and carbonates of alkali metals and alkaline earth metals, such as sodium hydroxide, potassium hydroxide, magnesium oxide, calcium oxide, sodium carbonate, potassium carbonate and calcium carbonate, all of which can also be employed in the presence of phase transfer catalysts such as, for example, triethylbenzylammonium chloride, tetrabutyl-ammonium bromide, Adogen 464 (=methyltrialkyl($C_8$–$C_{10}$)-ammonium chloride) or TDA 1 (=tris-(methoxyethoxyethyl)-amine). Alkali metals such as sodium or potassium can furthermore be used. Other substances which can be employed are the amides and hydrides of alkali metals and alkaline earth metals, such as sodium amide, sodium hydride and calcium hydride, and, moreover, also alkali metal alcoholates, such as sodium methylate, sodium ethylate and potassium tert-butylate.

When carrying out process (A) according to the invention, the reaction temperatures can be varied within a substantial range. In general, the process is carried out at temperatures between 0° C. and 250° C., preferably between 50° C. and 150° C.

Process (A) according to the invention is generally carried out under atmospheric pressure.

When carrying out process (A) according to the invention, the reactants of the formulae (II) and the deprotonating bases are generally employed in approximately twice the equimolar amounts. However, it is also possible to use one or the other component in a larger excess (up to 3 mol).

Process (Bα) comprises a process wherein compounds of the formula (Ia) are reacted with carboxylic halides of the formula (III).

Diluents which can be employed in process (Bα) according to the invention in which the acid halides are used are all solvents which are inert to these compounds. The following can preferably be used: hydrocarbons, such as benzine, benzene, toluene, xylene and tetralin, furthermore halogenohydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, in addition carboxylic esters, such as ethyl acetate, and also strongly polar solvents, such as dimethyl sulfoxide and sulfolane. The reaction can also be carried out in the presence of water if the acid halide is sufficiently stable to hydrolysis.

If the carboxylic acid halides are used, then suitable acid-binding agents in the reaction in accordance with process (Bα) according to the invention are all customary acid acceptors. The following can preferably be used: tertiary amines, such as triethylamine, pyridine, diazabicyclooctane (DABCO), diazabicycloundecene (DBU), diazabicyclononene (DBN), Hünig base and N,N-dimethylaniline, furthermore alkaline earth metal oxides such as magnesium oxide and calcium oxide, moreover alkali metal carbonates and alkaline earth metal carbonates, such as sodium carbonate, potassium carbonate and calcium carbonate, and also alkali metal hydroxides such as sodium hydroxide and potassium hydroxide.

When carboxylic acid halides are used, the reaction temperatures in process (Bα) according to the invention can also be varied within a substantial range. In general, the process is carried out at temperatures between −20° C. and +150° C., preferably between 0° C. and 100° C.

When carrying out process (Bα) according to the invention, the starting substances of the formula (Ia) and the carboxylic acid halide of the formula (III) are generally employed in approximately equivalent amounts. However, it is also possible to employ the carboxylic acid halide in a larger excess (up to 5 mol). Working-up is carried out by customary methods.

Process (Bβ) comprises a process wherein compounds of the formula (Ia) are reacted with carboxylic anhydrides of the formula (IV).

If, in process (Bβ) according to the invention, carboxylic anhydrides are used as reactant of the formula (IV), then diluents which can be used are preferably those diluents which are also preferably suitable when acid halides are used. Besides, an excess of the carboxylic anhydride employed can also simultaneously act as the diluent.

When carboxylic anhydrides are used, the reaction temperatures in process (Bβ) according to the invention can also be varied within a substantial range. In general, the process is carried out at temperatures between −20° C. and +150° C., preferably between 0° C. and 100° C.

When carrying out process (Bβ) according to the invention, the starting substances of the formula (Ia) and the carboxylic anhydride of the formula (IV) are generally employed in approximately equivalent amounts. However, it is also possible to employ the carboxylic anhydride in a larger excess (up to 5 mol). Working-up is carried out by customary methods.

In general, a procedure is followed in which diluent and an excess of carboxylic anhydride as well as the carboxylic acid which forms are removed by distillation or by washing with an organic solvent or water.

Process (C) comprises a process wherein compounds of the formula (Ia) are reacted with chloroformic esters or chloroformic thioesters of the formula (V).

If the relevant chloroformic esters or chloroformic thioesters are used, then acid-binding agents which are suitable in the reaction in accordance with process (C) according to the invention are all customary acid acceptors. The following can preferably be used: tertiary amines such as triethylamine, pyridine, DABCO, DBU, DBA, Hünig base and N,N-dimethyl-aniline, furthermore alkaline earth metal oxides such as magnesium oxide and calcium oxide, moreover alkali metal carbonates and alkaline earth metal carbonates, such as sodium carbonate, potassium carbonate and calcium carbonate, and also alkali metal hydroxides such as sodium hydroxide and potassium hydroxide.

If the chloroformic esters or chloroformic thioesters are used, then diluents which can be employed in process (C) according to the invention are all solvents which are inert to these compounds. The following can preferably be used: hydrocarbons, such as benzine, benzene, toluene, xylene and tetralin, furthermore halogenohydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, in addition carboxylic esters, such as ethyl acetate, and also strongly polar solvents such as dimethyl sulfoxide and sulfolane.

If the chloroformic esters or chloroformic thioesters are used as carboxylic acid derivatives of the formula (V), the reaction temperatures when carrying out process (C) according to the invention can be varied within a substantial range. If the process is carried out in the presence of a diluent and of an acid-binding agent, the reaction temperatures are generally between −20° C. and +100° C., preferably between 0° C. and 50° C.

Process (C) according to the invention is generally carried out under atmospheric pressure.

When carrying out process (C) according to the invention, the starting substances of the formula (Ia) and the relevant chloroformic ester or chloroformic thioester of the formula (V) are generally used in approximately equivalent amounts. However, it is also possible to employ one or the other reactant in a larger excess (up to 2 mol). Working-up is then carried out by customary methods. In general, a procedure is followed in which the salts which have precipitated are removed and the reaction mixture which remains is concentrated by stripping of the diluent.

In preparation process (Dα), approximately 1 mol of chloromonothioformic ester or chlorodithioformic ester of the formula (VI) is reacted per mol of starting compound of the formula (Ia) at 0° to 120° C., preferably at 20° to 60° C.

Suitable diluents which are added, if appropriate, are all inert polar organic solvents such as ethers, amides, sulfones, sulfoxides, but also halogenoalkanes.

The following are preferably employed: dimethyl sulfoxide, tetrahydrofuran, dimethylformamide or methylene chloride.

If, in a preferred embodiment, the enolate salt of the compound (Ia) is synthesized by adding strong deprotonating agents such as, for example, sodium hydride or potassium tertiary butylate, a further addition of acid-binding agents can be dispensed with.

If acid-binding agents are employed, then customary inorganic or organic bases are suitable, examples which may be mentioned being sodium hydroxide, sodium carbonate, potassium carbonate, pyridine and triethylamine.

The reaction can be carried out under atmospheric pressure or elevated pressure, preferably under atmospheric pressure. Working-up is carried out by customary methods.

In preparation process (Dβ), an equimolar amount or an excess of carbon disulfide is added per mol of starting compound of the formula (Ia). This process is preferably carried out at temperatures from 0° to 50° C., in particular at 20° to 30° C.

Frequently it is advantageous first to prepare the corresponding salt of the compound of the formula (Ia) by adding a deprotonating agent (such as, for example, potassium tertiary butylate or sodium hydride). The compound (Ia) is reacted with carbon disulfide until the formation of the intermediate is complete, for example after stirring at room temperature for several hours.

The further reaction with the alkyl halide of the formula (VII) is preferably carried out at 0° to 70° C., in particular at 20° to 50° C. At least an equimolar amount of alkyl halide is employed.

The process is carried out under atmospheric pressure or under elevated pressure, preferably under atmospheric pressure.

Again, working-up is carried out by customary methods.

In preparation process (E), approximately 1 mol of sulfonyl chloride (VIII) is reacted per mol of starting compound of the formula (Ia) at −20° to 150° C., preferably at 20° to 70° C.

Suitable diluents which are added, if appropriate, are all inert polar organic solvents such as ethers, amides, nitrites, sulfones, sulfoxides, or halogenated hydrocarbons such as methylene chloride.

The following are preferably employed: dimethyl sulfoxide, tetrahydrofuran, dimethylformamide and methylene chloride.

If, in a preferred embodiment, the enolate salt of the compound (Ia) is synthesized by adding strong deprotonating agents (such as, for example, sodium hydride or potassium tertiary butylate), a further addition of acid-binding agents can be dispensed with.

If acid-binding agents are employed, then suitable substances are customary inorganic or organic bases, examples which may be mentioned being sodium hydroxide, sodium carbonate, potassium carbonate, pyridine and triethylamine.

The reaction can be carried out under atmospheric pressure or under elevated pressure, preferably under atmospheric pressure. Working-up is carried out by customary methods.

In preparation process (F) for obtaining compounds of the structure (Ie), 1 to 2, preferably 1 to 1.3, mol of the phosphorus compound of the formula (IX) are reacted per mole of the compound (Ia) at temperatures between −40° C. and 150° C., preferably between −10° and 110° C.

Suitable diluents which are added, if appropriate, are all inert polar organic solvents such as halogenoalkanes, ethers, amides, nitrites, alcohols, sulfides, sulfones, sulfoxides and the like.

The following are preferably employed: acetonitrile, dimethyl sulfoxide, tetrahydrofuran, dimethylformamide and methylene chloride.

Suitable acid-binding agents which are added, if appropriate, are customary inorganic or organic bases such as hydroxides, carbonates or amines. Examples which may be mentioned are sodium hydroxide, sodium carbonate, potassium carbonate, pyridine and triethylamine.

The reaction can be carried out under atmospheric pressure or under elevated pressure, preferably under atmospheric pressure. Working-up is carried out by customary methods of organic chemistry. The end products obtained are preferably purified by crystallization, chromatographic purification or by so-called "incipient distillation", i.e. removal of the volatile components in vacuo.

Process (G) comprises a process in which compounds of the formula (Ia) are reacted with metal hydroxides or metal alkoxides of the formula (X) or amines of the formula (XI).

Diluents which can be employed in the process according to the invention are preferably ethers such as tetrahydrofuran, dioxane, diethyl ether, or else alcohols such as methanol, ethanol and isopropanol, but also water. Process (G) according to the invention is generally carried out under atmospheric pressure. The reaction temperatures are generally between −20° C. and 100° C., preferably between 0° C. and 50° C.

In preparation process (Hα), approximately 1 mol of isocyanate of the formula (XII) is reacted per mol of starting compound of the formula (Ia) at 0° to 100° C., preferably at 20° to 50° C.

Suitable diluents which are added, if appropriate, are all inert organic solvents such as ethers, amides, nitriles, sulfones and sulfoxides.

If appropriate, catalysts can be added so as to accelerate the reaction. Catalysts which can be employed very advantageously are organotin compounds such as, for example, dibutyltin dilaurate. The process is preferably carried out under atmospheric pressure.

In preparation process (Hβ), approximately 1 mol of carbamoyl chloride of the formula (XIII) is reacted per mol of starting compound of the formula (Ia) at 0° to 150° C., preferably at 20° to 70° C.

Suitable diluents which are added, if appropriate, are all inert polar organic solvents such as ethers, amides, sulfones, sulfoxides or halogenated hydrocarbons.

The following are preferably employed: dimethyl sulfoxide, tetrahydrofuran, dimethylformamide or methylene chloride.

If, in a preferred embodiment, the enolate salt of the compound (Ia) is synthesized by adding strong deprotonating agents (such as, for example, sodium hydride or potassium tertiary butylate), a further addition of acid-binding agent can be dispensed with.

If acid-binding agents are employed, then suitable substances are customary inorganic or organic bases, examples which may be mentioned being sodium hydroxide, sodium carbonate, potassium carbonate, triethylamine or pyridine.

The reaction can be carried out under atmospheric pressure or under elevated pressure, preferably under atmospheric pressure. Working-up is carried out by customary methods.

The active compounds are suitable for combating animal pests, preferably arthropods and nematodes, in particular insects and arachnids, which are encountered in agriculture, in forestry, in the protection of stored products and of materials and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera spec.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus, Gryllotalpa spp., Locusta migratoria* migratorioides, *Melanoplus differentialis* and *Schistocerca gregaria.*

From the order of the Dermaptera, for example, *Forficula auricularia.*

From the order of the Isoptera, for example, *Reticulitermes spp.*

From the order of the Anoplura, for example, *Phylloxera vastatrix, Pemphigus spp., Pediculus humanus* corporis, *Haematopinus spp.* and *Linognathus spp.*

From the order of the Mallophaga, for example, *Trichodectes spp.* and *Damalinea spp.*

From the order of the Thysanoptera, for example, *Hercinothrips femoralis* and *Thrips tabaci.*

From the order of the Heteroptera, for example, *Eurygaster spp., Dysdercus intermedius, Piesma quadrata, Cimex lectularius, Rhodnius prolixus* and *Triatoma spp.*

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp.* and *Psylla spp.*

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp., Bucculatrix thurberiella, Phyllocnistis citrella, Agrotis spp., Euxoa spp., Feltia spp., Earias insulana, Heliothis spp., Spodoptera exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis* and *Costelytra zealandica.*

From the order of the Hymenoptera, for example, *Diprion spp., Hoplocampa spp., Lasius spp., Monomorium pharaonis* and *Vespa app.*

From the order of the Diptera, for example, *Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae* and *Tipula paludosa.*

From the order of the Siphonaptera, for example, *Xenopsylla cheopis* and *Ceratophyllus spp.*

From the order of the Arachnida, for example, *Scorpio maurus* and *Latrodectus mactans.*

From the order of the Acarina, for example, *Acarus siro, Argas spp., Ornithodoros spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp.* and *Tetranychus spp.*

The active compounds according to the invention are distinguished by a powerful insecticidal and acaricidal activity.

They can be employed particularly successfully to combat insects which are harmful to plants, such as, for example, against the larvae of the mustard beetle (*Phaedon cochleariae*) or against the larvae of the green rice leafhopper (*Nephotettix cincticeps*) and against the caterpillars of the diamond-back moth (*Plutella maculipennis*).

The active compounds according to the invention can furthermore be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective combating of weeds in annual cultures.

The active compounds according to the invention are highly suitable for selectively combating monocotyledon weeds in dicotyledon cultures by the pre- and post-emergence methods. They can be employed, for example, in cotton or sugar beet for combating grass weeds, where they are highly successful.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulfoxide, as well as water.

As solid carriers there are suitable:

for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates as well as albumen hydrolysis products; as dispersing agents there are suitable: for example ligninsulfite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

Examples of particularly advantageous components in mixtures are the following compounds.

Fungicides:

2-aminobutane; 2-anilino-4-methyl-6-cyclopropylpyrimidine; 2',6'-dibromo-2-methyl-4'-trifluoromethoxy-4'-trifluoro-methyl-1,3-thizole-5-carboxanilide; 2,6-dichloro-N-(4-trifluoromethylbenzyl)benzamide; (E)-2-methoxyimino-N-methyl-2-(2-phenoxyphenyl)-acetamide; 8-hydroxyquinoline sulfate; methyl (E)-2-{2-[6-(2-cyanophenoxy)-pyrimidin-4-yloxy]-phenyl}-

3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulfide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetylaluminum, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulfate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulfur and sulfur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram Bactericides:

bronopol, dichlorophen, nitrapyrin, nickel dimethyldithiocarbamate, kasugamycin, octhilinone, furanecarboxylic acid, oxytetracyclin, probenazole, streptomycin, teclof talam, copper sulfate and other copper preparations Insecticides/Acarizides/Nematicides:

abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, beta-cyluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157 419, CGA 184699, chloethocarb, chlorethoxyfos, chlorfenvinphos, chlorfluazuron, chlormephos, chlorpyrifos, chlorpyrifos M, cisresmethrin, clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyraclofos, pyridaphenthion, pyresmethrin, pyrethrum, pyridaben, pyrimidifen, pyriproxifen, quinalphos,

RH 5992, salithion, sebufos, silafluofen, sulfotep, sulprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

Herbicides:

for example anilides such as, for example, diflufenican and propanil; arylcarboxylic acids such as, for example, dichloropicolinic acid, dicamba and picloram; aryloxy-alkanoic acids such as, for example, 2,4-D, 2,4-DB, 2,4-DP, fluroxypyr, MCPA, MCPP and triclopyr; aryloxy-phenoxy-alkanoic esters such as, for example, diclofopmethyl, fenoxaprop-ethyl, fluazifop-butyl, haloxyfopmethyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulfonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuronmethyl, triasulfuron and tribenuron-methyl; thiocarbamates such as, for example, butylate, cycloate, diallate, EPTC, esprocarb, molinate, prosulfocarb, thiobencarb and tri-allate; triazines such as, for example, atrazine, cyanazine, simazine, simetryn, terbutryn and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

The active compound according to the invention can furthermore be present in its commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight. The compounds are employed in a customary manner appropriate for the use forms.

When used against hygiene pests and pests of stored products, the active compounds are distinguished by an excellent residual action on wood and clay as well as a good stability to alkali on limed substrates.

The preparation and the use of the active compounds according to the invention can be seen from the examples which follow.

PREPARATION EXAMPLES

Example (Ia-1)

12.42 g of potassium t-butylate are introduced into 35 ml of dry tetrahydrofuran, with a solution of 16 g of methyl N-(4-chloro-2-methylphenyl)-acetyl-1-amino-cyclohexanecarboxylate in 100 ml of dry toluene is added under reflux, and the mixture is refluxed for 90 minutes. After cooling, 150 ml of water are added to the reaction solution, and the aqueous phase is separated off. The organic phase is washed again, using 75 ml of water. The aqueous phases are combined, the mixture is acidified using 16 ml of concentrated hydrochloric acid, and the precipitate is filtered off with suction and dried. 11.7 g (81% of theory) are obtained, m.p. 162° C.

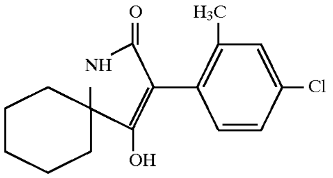

(Ia-1)

The following compounds are obtained analogously:

TABLE 8

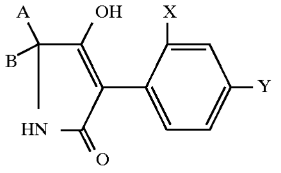

(Ia)

(Ia)

| Ex. No. | X | Y | A | B | Isomer | M.p. °C. |
|---|---|---|---|---|---|---|
| Ia-2 | Cl | $CH_3$ | $CH_3$ | $CH_3$ | — | 92 |
| Ia-3 | Cl | $CH_3$ | $-(CH_2)_5-$ | | — | >220 |
| Ia-4 | Cl | $CH_3$ | $-(CH_2)_2-CHCH_3-(CH_2)_2-$ | | β | 230 |
| Ia-5 | Cl | $CH_3$ | $-(CH_2)_3-CHCH_3-CH_2-$ | | β | 188 |
| Ia-6 | Cl | $CH_3$ | $-(CH_2)_2-CHOCH_3-(CH_2)_2-$ | | β | >220 |
| Ia-7 | $CH_3$ | Cl | $-(CH_2)_2-CHCH-(CH_2)_2-$ | | β | >230 |
| Ia-8 | $CH_3$ | Cl | $-(CH_2)_3-CHCH_3-CH_2-$ | | β | 153 |
| Ia-9 | $CH_3$ | Cl | $-(CH_2)_2CHCH_3-(CH_2)_2-$ | | β | >220 |
| Ia-10 | Cl | $CH_3$ | $-(CH_2)_2-O-(CH_2)_2-$ | | — | 167 |
| Ia-11 | Cl | $CH_3$ | i-$C_3H_7$ | $CH_3$ | — | 203 |
| Ia-12 | Cl | $CH_3$ | 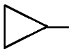 | $CH_3$ | — | 146 |
| Ia-13 | Cl | $CH_3$ | 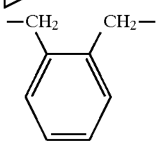 | | — | 196 |

TABLE 8-continued

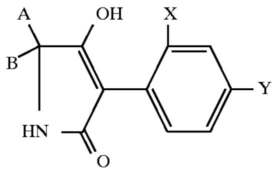

(Ia)

(Ia)

| Ex. No. | X | Y | A | B | Isomer | M.p. °C. |
|---|---|---|---|---|---|---|
| Ia-14 | Cl | $CH_3$ | $-(CH_2)_2-CHCH_3-CHCH_3CH_2-$ | | β | 142 |
| Ia-15 | $CH_3$ | Cl | $CH_3$ | $CH_3$ | — | 187 |
| Ia-16 | $CH_3$ | Cl | $-(CH_2)_2-O-(CH_2)_2-$ | | — | 189 |
| Ia-17 | $CH_3$ | Cl | 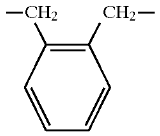 | | — | 202 |
| Ia-18 | $CH_3$ | Cl | $i-C_3H_7$ | $CH_3$ | — | 169 |

Example (Ib-1)

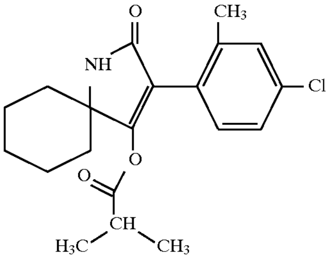

Example Ib-1

2.1 ml of triethylamine are added to 4.38 g of the compound of Example Ia-1 in 70 ml of dry methylene chloride, and 1.58 ml of isobutyroyl chloride in 5 ml of dry methylene chloride are added at 0° to 10° C. The reaction solution is washed twice using 50 ml of 0.5N sodium hydroxide solution and dried over magnesium sulfate, and the solvent is distilled off. 2.6 g (47% of theory) remain, m.p. 186° C.

The following compounds are obtained analogously and in accordance with the general preparation instructions:

TABLE 9

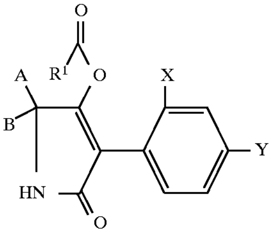

(Ib)

(Ib)

| Ex. No. | X | Y | A | B | $R^1$ | Isomer | M.p. °C. |
|---|---|---|---|---|---|---|---|
| Ib-2 | Cl | $CH_3$ | $(CH_2)_2-CHCH_3-(CH_2)_2-$ | | $CH_3$ | β | 217 |
| Ib-3 | Cl | $CH_3$ | $(CH_2)_2-CHCH_3-(CH_2)_2-$ | | $i-C_3H_7$ | β | 183 |
| Ib-4 | Cl | $CH_3$ | $(CH_2)_3-CHCH_3-CH_2-$ | | $CH_3$ | β | 211 |
| Ib-5 | Cl | $CH_3$ | $(CH_2)_3-CHCH_3-CH_2-$ | | $i-C_3H_7$ | β | 138 |
| Ib-6 | Cl | $CH_3$ | $(CH_2)_2-CHOCH_3-(CH_2)_2-$ | | $CH_3$ | β | 198 |
| Ib-7 | Cl | $CH_3$ | $(CH_2)_2-CHOCH_3-(CH_2)_2-$ | | $i-C_3H_7$ | β | 141 |
| Ib-8 | $CH_3$ | Cl | $(CH_2)_2-CHCH_3-(CH_2)_2-$ | | $CH_3$ | β | 208 |
| Ib-9 | $CH_3$ | Cl | $(CH_2)_2-CHCH_3-(CH_2)_2-$ | | $i-C_3H_7$ | β | 218 |
| Ib-10 | $CH_3$ | Cl | $(CH_2)_3-CHCH_3-CH_2-$ | | $CH_3$ | β | 230 |
| Ib-11 | $CH_3$ | Cl | $(CH_2)_3-CHCH_3-CH_2-$ | | $i-C_3H_7$ | β | 163 |
| Ib-12 | Cl | $CH_3$ | $-(CH_2)_5-$ | | $i-C_3H_7$ | — | 174 |
| Ib-13 | Cl | $CH_3$ | $-(CH_2)_2-O-(CH_2)_2-$ | | $CH_3$ | — | 217 |
| Ib-14 | Cl | $CH_3$ | $i-C_3H_7$ | $CH_3$ | $CH_3$ | — | 191 |
| Ib-15 | Cl | $CH_3$ | 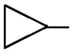 | $CH_3$ | $CH_3$ | — | 188 |

TABLE 9-continued

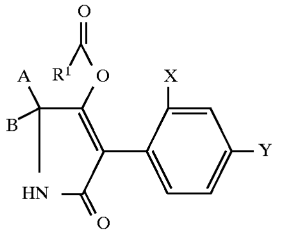

(Ib)

(Ib)

| Ex. No. | X | Y | A | B | $R^1$ | Isomer | M.p. °C. |
|---|---|---|---|---|---|---|---|
| Ib-16 | Cl | $CH_3$ | 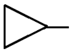 | $CH_3$ | i-$C_3H_7$ | — | 211 |
| Ib-17 | Cl | $CH_3$ | 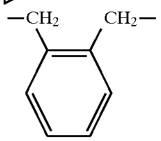 | | $CH_3$ | — | >220 |
| Ib-18 | Cl | $CH_3$ | 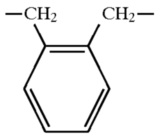 | | i-$C_3H_7$ | — | 189 |
| Ib-19 | $CH_3$ | Cl | $-(CH_2)_2-CHOCH_3-(CH_2)_2-$ | | $CH_3$ | β | 218 |
| Ib-20 | $CH_3$ | Cl | $-(CH_2)_2-CHOCH_3-(CH_2)_2-$ | | i-$C_3H_7$ | β | 176 |
| Ib-21 | $CH_3$ | Cl | $-(CH_2)_2-O-(CH_2)_2-$ | | $CH_3$ | — | 209 |
| Ib-22 | $CH_3$ | Cl | $-(CH_2)_2-O-(CH_2)_2-$ | | i-$C_3H_7$ | — | 192 |
| Ib-23 | $CH_3$ | Cl | 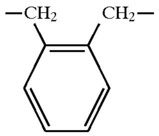 | | $CH_3$ | — | 215 |
| Ib-24 | $CH_3$ | Cl | 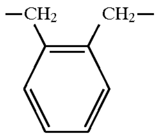 | | i-$C_3H_7$ | — | 209 |
| Ib-25 | $CH_3$ | Cl | i-$C_3H_7$ | $CH_3$ | $CH_3$ | — | 161 |
| Ib-26 | $CH_3$ | Cl | i-$C_3H_7$ | $CH_3$ | i-$C_3H_7$ | — | 152 |
| Ib-27 | $CH_3$ | Cl | $-(CH_2)_2-CHCH_3-(CH_2)_2-$ | | i-$C_4H_9$ | β | 201 |
| Ib-28 | $CH_3$ | Cl | $-(CH_2)_2-CHCH_3-(CH_2)_2-$ | | $H_5C_2O-CH_2$ | β | 178 |
| Ib-29 | $CH_3$ | Cl | $-(CH_2)_2-CHCH_3-(CH_2)_2-$ | | 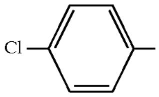 | β | >220 |
| Ib-30 | $CH_3$ | Cl | $-(CH_2)_2-CHCH_3-(CH_2)_2-$ | | 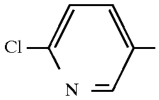 | β | >220 |
| Ib-31 | $CH_3$ | Cl | $-(CH_2)_2-CHCH_3-(CH_2)_2-$ | | 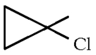 | β | 220 |
| Ib-32 | $CH_3$ | Cl | $-(CH_2)_3-CHCH_3-CH_2-$ | | 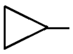 | β | 196 |
| Ib-33 | $CH_3$ | Cl | $-(CH_2)_3-CHCH_3-CH_2-$ | | i-$C_4H_7$ | β | 172 |
| Ib-34 | $CH_3$ | Cl | $-(CH_2)_3-CHCH_3-CH_2-$ | | $H_5C_2O-CH_2$ | β | 143 |

TABLE 9-continued

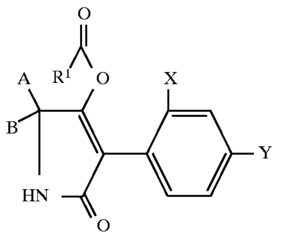
(Ib)

(Ib)

| Ex. No. | X | Y | A | B | $R^1$ | Isomer | M.p. °C. |
|---|---|---|---|---|---|---|---|
| Ib-35 | $CH_3$ | Cl | $-(CH_2)_3-CHCH_3-CH_2-$ | | 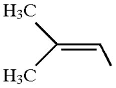 | β | 189 |
| Ib-36 | $CH_3$ | Cl | $-(CH_2)_3-CHCH_3-CH_2-$ | | 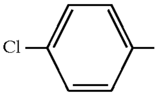 | β | >220 |
| Ib-37 | $CH_3$ | Cl | $-(CH_2)_3-CHCH_3-CH_2-$ | | 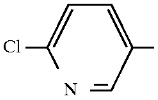 | β | 220 |
| Ib-38 | $CH_3$ | Cl | $-(CH_2)_3-CHCH_3-CH_2-$ | | 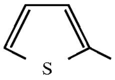 | β | 218 |
| Ib-39 | $CH_3$ | Cl | $-(CH_2)_3-CHCH_3-CH_2-$ | | 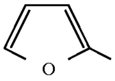 | β | 218 |
| Ib-40 | Cl | $CH_3$ | $-(CH_2)_2-O-(CH_2)_2-$ | | $H_5C_2-O-CH_2$ | — | 168 |
| Ib-41 | Cl | $CH_3$ | $-(CH_2)_2-O-(CH_2)_2-$ | | 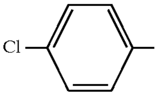 | — | >220 |
| Ib-42 | Cl | $CH_3$ | $-(CH_2)_2-O-(CH_2)_2-$ | | 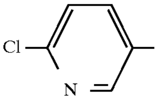 | — | >220 |
| Ib-43 | Cl | $CH_3$ | $-(CH_2)_2-O-(CH_2)_2-$ | | n-$C_{15}H_{31}$ | — | 99 |
| Ib-44 | $CH_3$ | Cl | $-(CH_2)_2-O-(CH_2)_2-$ | | 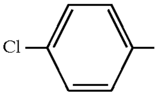 | — | 198 |
| Ib-45 | $CH_3$ | Cl | $-(CH_2)_2-O-(CH_2)_2-$ | | 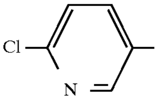 | — | 206 |
| Ib-46 | $CH_3$ | Cl | $-(CH_2)_2-O-(CH_2)_2-$ | | n-$C_{15}H_{31}$ | — | 136 |
| Ib-47 | Cl | $CH_3$ | $-(CH_2)_2-CHCH_3-(CH_2)_2-$ | | $H_5C_2-O-CH_2$ | β | 175 |
| Ib-48 | Cl | $CH_3$ | $-(CH_2)_2-CHCH_3-(CH_2)_2-$ | | n-$C_{15}H_{31}$ | β | 96 |
| Ib-49 | Cl | $CH_3$ | $-(CH_2)_2-CHCH_3-(CH_2)_2-$ | | 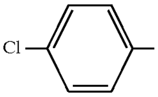 | β | 218 |
| Ib-50 | Cl | $CH_3$ | $-(CH_2)_2-CHCH_3-(CH_2)_2-$ | | 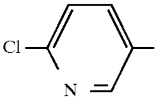 | β | 209 |

TABLE 9-continued

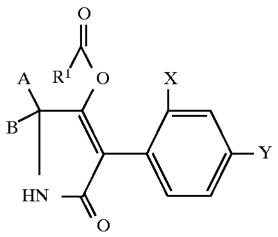

(Ib)

| Ex. No. | X | Y | A | B | $R^1$ | Isomer | M.p. °C. |
|---|---|---|---|---|---|---|---|
| Ib-51 | $CH_3$ | Cl | $-(CH_2)_3-CHCH_3-CH_2-$ | | n-$C_{15}H_{31}$ | β | 84 |
| Ib-52 | Cl | $CH_3$ | $-(CH_2)_3-CHCH_3-CH_2-$ | | n-$H_9C_4$—CH($C_2H_5$)— | β | 120 |
| Ib-53 | Cl | $CH_3$ | $-(CH_2)_3-CHCH_3-CH_2-$ | | i-$C_4H_9$ | β | 154 |
| Ib-54 | Cl | $CH_3$ | $-(CH_2)_3-CHCH_3-CH_2-$ | | $H_5C_2-O-CH_2$ | β | 166 |
| Ib-55 | Cl | $CH_3$ | $-(CH_2)_3-CHCH_3-CH_2-$ | | 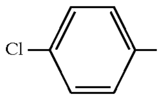 | β | 214 |
| Ib-56 | Cl | $CH_3$ | $-(CH_2)_3-CHCH_3-CH_2-$ | | 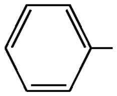 | β | 212 |
| Ib-57 | Cl | $CH_3$ | $-(CH_2)_3-CHCH_3-CH_2-$ | | n-$C_{15}H_{31}$ | β | 78 |
| Ib-58 | $CH_3$ | Cl | $-(CH_2)_2-O-(CH_2)_2-$ | | $H_5C_2-O-CH_2$ | — | 182 |

Example (Ic-1)

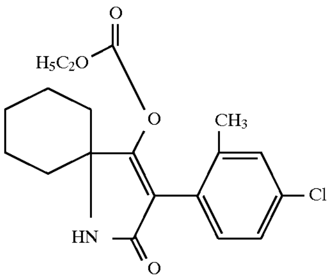

Ic-1

2.1 ml of triethylamine are added to 4.36 g of the compound of Example Ia-1 in 70 ml of dry methylene chloride, and 1.5 ml of ethyl chloroformate in 5 ml of dry methylene chloride are added at 0° to 10° C. The reaction solution is washed twice using 50 ml of 0.5N sodium hydroxide solution and dried over magnesium sulfate, and the solvent is distilled off. 4.1 g (75% of theory) remain, m.p. 184° C.

The following compounds are obtained analogously and in accordance with the general preparation instructions:

TABLE 10

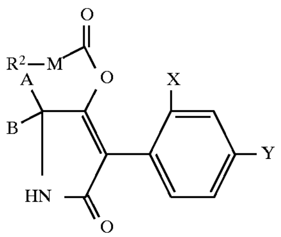

(Ic)

| Ex. No. | X | Y | A | B | M | $R^3$ | Isomer | M.p. °C. |
|---|---|---|---|---|---|---|---|---|
| Ic-2 | Cl | $CH_3$ | $(CH_2)_2-CHCH_3-(CH_2)_2-$ | | O | $C_2H_5$ | β | 218 |
| Ic-3 | Cl | $CH_3$ | $(CH_2)_2-CHCH_3-(CH_2)_2-$ | | O | i-$C_3H_7$ | β | 215 |

TABLE 10-continued

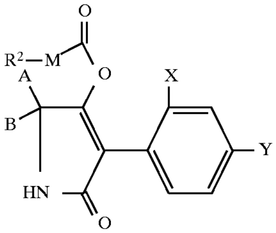

(Ic)

(Ic)

| Ex. No. | X | Y | A | B | M | $R^3$ | Isomer | M.p. °C. |
|---|---|---|---|---|---|---|---|---|
| Ic-4 | Cl | $CH_3$ | $(CH_2)_3-CHCH_3-CH_2-$ | | O | $C_2H_5$ | β | 173 |
| Ic-5 | Cl | $CH_3$ | $(CH_2)_2-CHOCH_3-(CH_2)_2-$ | | O | $C_2H_5$ | β | 163 |
| Ic-6 | Cl | $CH_3$ | $(CH_2)_2-CHOCH_3-(CH_2)_2-$ | | O | s-$C_4H_9$ | β | 124 |
| Ic-7 | $CH_3$ | Cl | $(CH_2)_2-CHCH_2(CH_2)_2-$ | | O | $C_2H_5$ | β | 188 |
| Ic-8 | $CH_3$ | Cl | $(CH_2)_3-CHCH_3-CH_2-$ | | O | $C_2H_5$ | β | 168 |
| Ic-9 | Cl | $CH_3$ | $-(CH_2)_5-$ | | O | $C_2H_5$ | — | 168 |
| Ic-10 | Cl | $CH_3$ | $CH_3$ | $CH_3$ | O | $C_2H_5$ | — | 162 |
| Ic-11 | Cl | $CH_3$ | $-(CH_2)_2-O-(CH_2)_2-$ | | O | $C_2H_5$ | — | >220 |
| Ic-12 | Cl | $CH_3$ | $-(CH_2)_2-O-(CH_2)_2-$ | | O | s-$C_4H_9$ | — | 169 |
| Ic-13 | Cl | $CH_3$ | i-$C_3H_7$ | $CH_3$ | O | $C_2H_5$ | — | 192 |
| Ic-14 | Cl | $CH_3$ | i-$C_3H_7$ | $CH_3$ | O | s-$C_4H_9$ | — | 173 |
| Ic-15 | Cl | $CH_3$ | 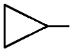 | $CH_3$ | O | $C_2H_5$ | — | 179 |
| Ic-16 | Cl | $CH_3$ | 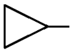 | $CH_3$ | O | s-$C_4H_9$ | — | 174 |
| Ic-17 | Cl | $CH_3$ | 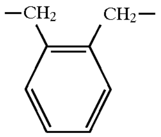 | | O | $C_2H_5$ | — | 174 |
| Ic-18 | $CH_3$ | Cl | $-(CH_2)_2-CHCH_3-CH_2-$ | | S | i-$C_3H_7$ | — | 205–207 |
| Ic-19 | $CH_3$ | Cl | $-(CH_2)_2-CHOCH_3-(CH_2)_2-$ | | O | $C_2H_5$ | β | 141 |
| Ic-20 | $CH_3$ | Cl | $-(CH_2)_2-CHOCH_3-(CH_2)_2-$ | | O | s-$C_4H_9$ | β | 154 |
| Ic-21 | $CH_3$ | Cl | $-(CH_2)_2-O-(CH_2)_2-$ | | O | $C_2H_5$ | — | >220 |
| Ic-22 | $CH_3$ | Cl | 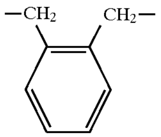 | | O | $C_2H_5$ | — | 206 |
| Ic-23 | $CH_3$ | Cl | i-$C_3H_7$ | $CH_3$ | O | $C_2H_5$ | — | 159 |
| Ic-24 | $CH_3$ | Cl | i-$C_3H_7$ | $CH_3$ | O | s-$C_4H_9$ | — | 172 |
| Ic-25 | $CH_3$ | Cl | $CH_3$ | $CH_3$ | O | $C_2H_5$ | — | 172 |
| Ic-26 | $CH_3$ | Cl | $-(CH_2)_2-CHCH_3-(CH_2)_2-$ | | O | $CH_3$ | β | 178 |
| Ic-27 | $CH_3$ | Cl | $-(CH_2)_2-CHCH_3-(CH_2)_2-$ | | O | i-$C_4H_9$ | β | 194 |
| Ic-28 | $CH_3$ | Cl | $-(CH_2)_2-CHCH_3-(CH_2)_2-$ | | O | i-$C_3H_7$ | β | 184 |
| Ic-29 | $CH_3$ | Cl | $-(CH_2)_2-CHCH_3-(CH_2)_2-$ | | O | s-$C_4H_9$ | β | 211 |
| Ic-30 | $CH_3$ | Cl | $-(CH_2)_2-CHCH_3-(CH_2)_2-$ | | O | 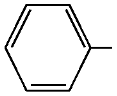 | β | 200 |
| Ic-31 | $CH_3$ | Cl | $-(CH_2)_2-CHCH_3-(CH_2)_2-$ | | O | 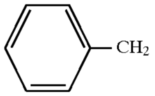 | β | 219 |
| Ic-32 | $CH_3$ | Cl | $-(CH_2)_3-CHCH_3-CH_2-$ | | O | $CH_3$ | β | 217 |
| Ic-33 | $CH_3$ | Cl | $-(CH_2)_3-CHCH_3-CH_2-$ | | O | i-$C_3H_7$ | β | 186 |
| Ic-34 | $CH_3$ | Cl | $-(CH_2)_3-CHCH_3-CH_2-$ | | O | s-$C_4H_9$ | β | 185 |
| Ic-35 | $CH_3$ | Cl | $-(CH_2)_3-CHCH_3-CH_2-$ | | O | i-$C_4H_9$ | β | 191 |

TABLE 10-continued

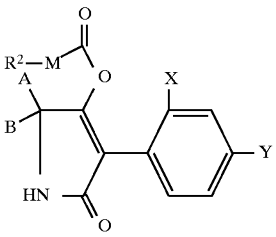

(Ic)

(Ic)

| Ex. No. | X | Y | A | B | M | $R^3$ | Isomer | M.p. °C. |
|---|---|---|---|---|---|---|---|---|
| Ic-36 | $CH_3$ | Cl | $-(CH_2)_3-CHCH_3-CH_2-$ | | O | 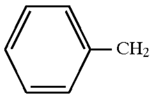 | β | 196 |
| Ic-37 | Cl | $CH_3$ | 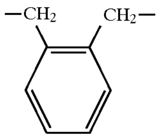 | | O | i-$C_3H_7$ | — | 205 |
| Ic-38 | Cl | $CH_3$ | 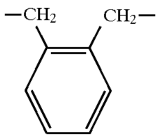 | | O | i-$C_4H_9$ | — | 135 |
| Ic-39 | Cl | $CH_3$ | $-(CH_2)_2-O-(CH_2)_2-$ | | O | $CH_3$ | — | 209 |
| Ic-40 | Cl | $CH_3$ | $-(CH_2)_2-O-(CH_2)_2-$ | | O | i-$C_3H_7$ | — | 208 |
| Ic-41 | Cl | $CH_3$ | $-(CH_2)_2-O-(CH_2)_2-$ | | O | i-$C_4H_9$ | — | 202 |
| Ic-42 | Cl | $CH_3$ | $-(CH_2)_2-O-(CH_2)_2-$ | | O | 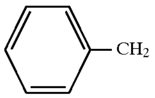 | — | 209 |
| Ic-43 | $CH_3$ | Cl | $-(CH_2)_2-O-(CH_2)_2-$ | | O | $CH_3$ | — | 218 |
| Ic-44 | $CH_3$ | Cl | $-(CH_2)_2-O-(CH_2)_2-$ | | O | i-$C_3H_7$ | — | 207 |
| Ic-45 | $CH_3$ | Cl | $-(CH_2)_2-O-(CH_2)_2-$ | | O | i-$C_4H_9$ | — | 211 |
| Ic-46 | $CH_3$ | Cl | $-(CH_2)_2-O-(CH_2)_2-$ | | O | 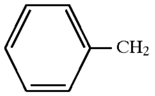 | — | 174 |
| Ic-47 | Cl | $CH_3$ | $-(CH_2)_2-CHCH_3-(CH_2)_2-$ | | O | t-$C_4H_9-CH_2$ | β | 213 |
| Ic-48 | Cl | $CH_3$ | $-(CH_2)_2-CHCH_3-(CH_2)_2-$ | | O | s-$C_4H_9$ | β | 164 |
| Ic-49 | Cl | $CH_3$ | $-(CH_2)_2-CHCH_3-(CH_2)_2-$ | | O | i-$C_4H_9$ | β | 167 |
| Ic-50 | Cl | $CH_3$ | $-(CH_2)_2-CHCH_3-(CH_2)_2-$ | | O | 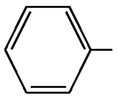 | β | 220 |
| Ic-51 | Cl | $CH_3$ | $-(CH_2)_3-CHCH_3-CH_2-$ | | O | i-$C_3H_7$ | β | 203 |
| Ic-52 | Cl | $CH_3$ | $-(CH_2)_3-CHCH_3-CH_2-$ | | O | i-$C_4H_9$ | β | 179 |
| Ic-53 | Cl | $CH_3$ | $-(CH_2)_3-CHCH_3-CH_2-$ | | O | s-$C_4H_9$ | β | 158 |

Example Id-1

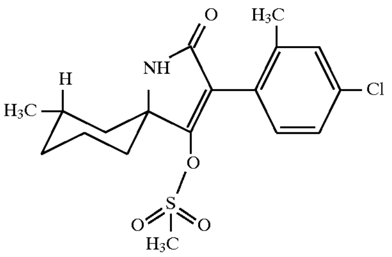

1.4 ml of triethylamine are added to 3.05 g of the compound of Example Ia-8 in 70 ml of dry methylene chloride, and 1.15 ml of methanesulfonyl chloride in 5 ml of dry methylene chloride are added at 0° to 10° C. The reaction solution is washed twice using 50 ml of 0.5N sodium hydroxide solution and dried over magnesium sulfate, and the solvent is distilled off. 3 g (78% of theory) remain, m.p. 198° C.

Example Ie-1

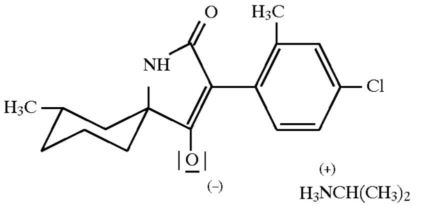

3.06 g (10 mmol) of the compound Ia-8 are suspended in 50 ml of anhydrous methylene chloride, and 1.02 ml (12 mmol) of anhydrous isopropylamine are added. After 15 minutes, the solvent is evaporated in vacuo. 3.6 g (98% of theory) of the compound Ie-1 of m.p. 152° C. are obtained.

Example Ig-1

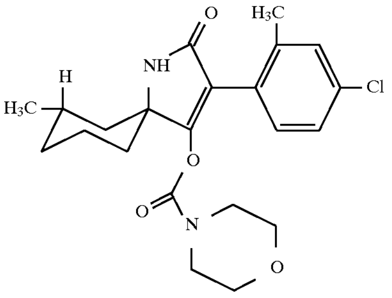

2.28 g of diazabicycloundecene are added to 4.59 g of the compound of Example Ia-8 in 50 ml of dry tetrahydrofuran, and 1.76 ml of morpholinecarbamoyl chloride in 5 ml of dry tetrahydrofuran are added at 0° to 10° C., and the mixture is subsequently refluxed for 3 hours. The reaction solution is washed twice using 50 ml of 0.5N sodium hydroxide solution and dried over sodium sulfate, and the solvent is distilled off. 2.6 g (47% of theory) remain, m.p. 182° C.

PREPARATION OF THE STARTIMG COMPOUNDS

Example (II-1)

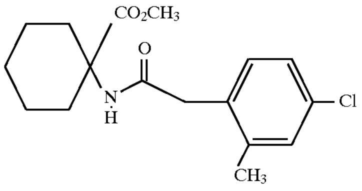

14.5 g (75 mmol) of methyl 1-amino-cyclohexanecarboxylate hydrochloride are introduced into 180 ml of absolute tetrahydrofuran, 21 ml of triethylamine are added, 15.2 g (75 mmol) of 4-chloro-2-methyl-phenylacetyl chloride in 20 ml of absolute tetrahydrofuran are added dropwise at 0° to 10° C., and stirring is continued for 1 hour at room temperature. The reaction mixture is poured into 500 ml of ice-water+200 ml of HCl, and the product which has precipitated is, filtered off with suction and dried. After recrystallization from methyl tert-butyl ether/n-hexane, 16 g (65% of theory) of the product shown above are obtained, melting point 151° C.

Example (II-2)

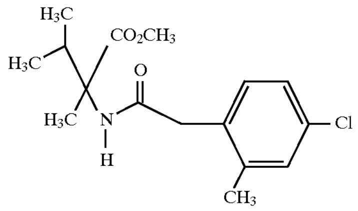

70.4 g (0.253 mol) of N-(2-chloro-4-methylphenylacetyl) -2-amino-2,3-dimethyl-butyronitrile in 500 ml of methylene chloride are added dropwise to 124.4 g (1.27 mol) of concentrated sulfuric acid in such a way that the solution is at a moderate boil. After two hours, 176 ml of absolute methanol are added dropwise, and the mixture is refluxed for 6 hours. The reaction mixture is poured onto 1.25 kg of ice and extracted using methylene chloride. The combined methylene chloride phases are washed using saturated sodium hydrogen carbonate solution and dried, the solvent is evaporated in vacuo, and the residue is recrystallized from methyl tert-butyl ether/n-hexane.

In this manner, 69.6 g (88% of theory) of the compound II-2 of m.p. 96° C. are obtained.

The examples shown in Table 11 are obtained analogously to Examples (II-1) and (II-2).

TABLE 11

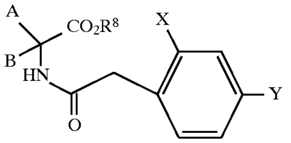

(II)

| Ex. No. | X | Y | A | B | $R^3$ | Isomer | (II) M.p. °C. |
|---|---|---|---|---|---|---|---|
| II-3 | Cl | $CH_3$ | $-(CH_2)_5-$ | | $CH_3$ | — | 102 |
| II-4 | Cl | $CH_3$ | $-(CH_2)_2-CHCH_2-(CH_2)_2-$ | | $CH_3$ | β | 124 |
| II-5 | Cl | $CH_3$ | $-(CH_2)_3-CHCH_3-CH_2-$ | | $CH_3$ | β | 127 |
| II-6 | Cl | $CH_3$ | $-(CH_2)_2-CHOCH_3-(CH_2)_2-$ | | $CH_3$ | β | 106 |
| II-7 | $CH_3$ | Cl | $-(CH_2)_2-CHCH_3-(CH_2)_2-$ | | $CH_3$ | β | 161 |
| II-8 | $CH_3$ | Cl | $-(CH_2)_3-CHCH_2-CH_2-$ | | $CH_3$ | β | 136 |
| II-9 | $CH_3$ | Cl | $-(CH_2)_2-CHOCH_3-(CH_2)_2-$ | | $CH_3$ | β | 124 |
| II-10 | $CH_3$ | Cl | $CH_3$ | $CH_3$ | $CH_3$ | — | 169 |
| II-11 | $CH_3$ | Cl | $i-C_3H_7$ | $CH_3$ | $CH_3$ | — | 126 |
| II-12 | $CH_3$ | Cl | $-(CH_2)_2-O-(CH_2)_2-$ | | $CH_3$ | — | 117 |
| II-13 | $CH_3$ | Cl | 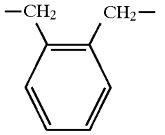 | | $CH_3$ | — | 169 |
| II-14 | $CH_3$ | Cl | 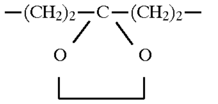 | | $CH_3$ | — | 115 |
| II-15 | Cl | $CH_3$ | $CH_3$ | $CH_3$ | $CH_3$ | — | 101 |
| 11-16 | Cl | $CH_3$ | 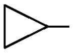 | $CH_3$ | $CH_3$ | — | 118 |
| II-17 | Cl | $CH_3$ | $-(CH_2)_3-O-(CH_2)_2-$ | | $CH_3$ | — | 137 |
| II-18 | Cl | $CH_3$ | 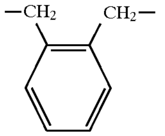 | | $CH_3$ | — | 168 |
| II-19 | Cl | $CH_3$ | $-(CH_2)_2-CHCH_3-CHCH_3-CH_2-$ | | $CH_3$ | β | 143 |
| II-20 | Cl | $CH_3$ | 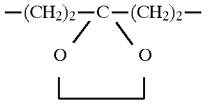 | | $CH_3$ | — | 115 |

Example (XVII-1)

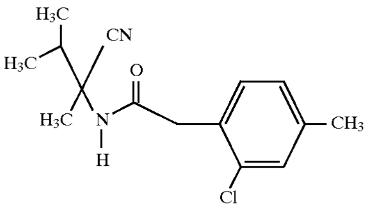

33.6 g (0.3 mol) of 2-amino-2,3-dimethyl-butyronitrile are introduced into 450 ml of absolute tetrahydrofuran, 42 ml of triethylamine are added, and 60.9 g of 2-chloro-4-methyl-phenylacetyl chloride are added dropwise at 0° to 10° C. Stirring is continued for one hour at room temperature, the batch is stirred into 1.3 1 of ice-water and 200 ml of 1N HCl, and the precipitate is filtered off with suction, dried and recrystallized from methyl tertbutyl ether/n-hexane. In this manner, 70.4 g (84% of theory) of the product shown above of m.p. 112° C. are obtained.

The compounds of the formula (XVII) listed in Table 12 are obtained analogously.

TABLE 12

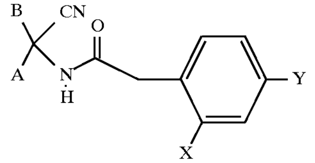

(XVII)

| Ex. No. | X | Y | A | B | (XVII) M.p. |
|---|---|---|---|---|---|
| XVII-2 | Cl | $CH_3$ | $-(CH_2)_2-O-(CH_2)_2-$ | | 156 |

TABLE 12-continued

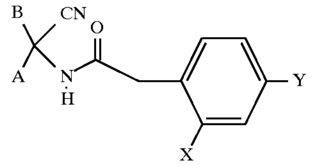

(XVII)

(XVII)

| Ex. No. | X | Y | A | B | M.p. |
|---|---|---|---|---|---|
| XVII-3 | Cl | $CH_3$ | 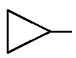 | $CH_3$ | 169 |
| XVII-4 | Cl | $CH_3$ | 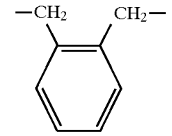 | | 121 |
| XVII-5 | $CH_3$ | Cl | $-(CH_2)_2-O-(CH_2)_2-$ | | 112 |
| XVII-6 | $CH_3$ | Cl | i-$C_3H_7$ | $CH_3$ | 136 |
| XVII-7 | $CH_3$ | Cl | 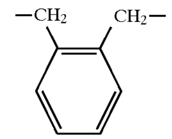 | | 112 |

USE EXAMPLES

Example A

Phaedon larvae test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (Phaedon cochleariae) while the leaves are still moist.

After the specified periods of time, the destruction in % is determined. 100% means that all the beetle larvae have been killed; 0% means that none of the beetle larvae have been killed.

In this test, a destruction rate of 100% was shown, after 7 days, for example by the compounds of Preparation Examples Ia-4 and Ia-5 at an exemplary active compound concentration of 0.01%.

Example B

Plutella test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (Plutella maculipennis) while the leaves are still moist.

After the specified periods of time, the destruction in % is determined. 100% means that all the caterpillars have been killed; 0% means that none of the caterpillars have been killed.

In this test, a destruction rate of 100% was shown, after 7 days, for example by the compounds of Preparation Examples Ia-4 and Ia-7 at an exemplary active compound concentration of 0.01%.

A destruction rate of 100% was shown, after 3 days, for example by the compounds of Preparation Examples Ib-9 and Ib-11 at an exemplary active compound concentration of 0.01%.

A destruction rate of 100% was shown by the compound of Preparation Examples Ia-7 (0.01%, 7 days), Ib-8 (0.01%, 3 days) and Ic-7 (0.01%, 3 days) at the active compound concentrations and after the periods indicated in brackets.

Example C

Nephotettix test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Rice seedlings (*Oryza sativa*) are treated by being dipped into the preparation of active compound of the desired concentration and are infested with the green rice leafhopper (*Nephotettix cincticeps*) while the seedlings are still moist.

After the specified periods of time, the destruction in % is determined. 100% means that all leafhoppers have been killed; 0% means that none of the leafhoppers have been killed.

In this test, a destruction rate of 100% was shown, after 6 days, for example by the compounds of Preparation Examples Ia-4, Ia-5, Ib-8, Ib-9 and Ib-1 at an exemplary active compound concentration of 0.01%.

Example D

Myzus test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) which are severely infested with the green peach aphid (Myzus persicae) are treated by being dipped into the preparation of active compound of the desired concentration.

After the specified periods of time, the destruction in % is determined. 100% means that all the aphids have been killed; 0% means that none of the aphids have been killed.

In this test, a degree of destruction of at least 70% was shown, after 6 days, for example by the compounds of Preparation Examples Ia-4, Ia-7 and Ia-8 at an exemplary active compound concentration of 0.01%.

A destruction rate of 90% was shown, after 6 days, for example by the compound of Preparation Example Ib-11 at an exemplary active compound concentration of 0.1%.

Example E

Panonychus test

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with emulsifier-water to the desired concentrations.

Plum trees (*Prunus domestica*) approximately 30 cm high which are severely infested with all development stages of the fruit tree red spider mite (*Panonychus ulmi*) are sprayed with a preparation of the active compound of the desired concentration.

After the specified periods of time, the destruction in % is determined. 100% means that all the spider mites have been killed; 0% means that none of the spider mites have been killed.

In this test, a degree of destruction of at least 95% was shown, after 7 days, for example by the compounds of Preparation Examples Ia-8, Ib-8, Ib-9, Ic-7, Ib-10, Ib-11, Ic-8, Ia-4 and Ia-5 at an exemplary active compound concentration of 0.02%.

Example F

Tetranychus test (OP resistant/spray treatment)

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with emulsifier-water to the desired concentrations.

Bean plants (*Phaseolus vulgaris*) which are severely infected with all development stages of the greenhouse red spider mite (*Tetranychus urticae*) are sprayed with a preparation of active compound of the desired concentration.

After the specified periods of time, the destruction in % is determined. 100% means that all the spider mites have been killed; 0% means that none of the spider mites have been killed.

In this test, a degree of destruction of at least 95% was shown, after 7 days, for example by the compounds of Preparation Examples Ia-7, Ia-8, Ib-8, Ib-9, Ic-7, Ib-10, Ib-11, Ic-8, Ia-4 and Ia-5 at an exemplary active compound concentration of 0.02%.

Example G

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil, and after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)

100%=total destruction

In this test, for example the compound according to the preparation example (Ic-14) was very well tolerated by Beta vulgaris at an exemplary amount of 250 g/ha and showed a degree of damage of at least 95% to the following test plants: *Alopecurus myosuroides, Digitaria sanguinalis, Echinochloa colonum, Lolium perenne* and *Setaria viridis.*

We claim:

1. An acyl-amino ester of the formula

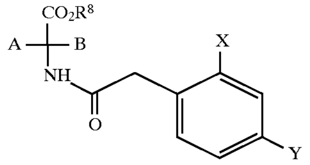

(II)

in which

A represents hydrogen, alkyl, alkenyl, alkoxyalkyl or alkylthioalkyl, each of which is optionally substituted by substituents selected from the group consisting of halogen, cycloalkyl optionally substituted aryl, and optionally substituted arylalkyl wherein the optional substituents are substituents selected from the group consisting of halogen, alkyl, halogenoalkyl, alkoxy and nitro, B represents hydrogen, alkyl or alkoxyalkyl, or A and B together with the carbon atom to which they are bonded represent a saturated or unsaturated, unsubstituted or substituted 5 or 6 member cycle, X represents halogen or alkyl, Y represents halogen or alkyl, and $R^8$ represents alkyl, provided that one X and Y represents halogen and the other represents alkyl.

2. A compound according to claim 1, in which

A represents hydrogen, or $C_1$–$C_{12}$-alkyl, $C_3$–$C_8$-alkenyl, $C_1$–$C_{10}$-alkoxy-$C_1$–$C_8$-alkyl, $C_1$–$C_8$-polyalkoxy-$C_1$–$C_8$-alkyl or $C_1$–$C_{10}$-alkylthio-$C_1$–$C_6$-alkyl, each of which is optionally substituted by substituents selected from the group consisting of halogen, or cycloalkyl having 3 to 8 ring atoms which is optionally substituted by halogen, $C_1$–$C_4$-alkyl or $C_1$–$C_4$-alkoxy or represents aryl, or aryl-$C_1$–$C_6$-alkyl, each or which is optionally substituted by substituents selected from the group consisting of halogen, $C_1$–$C_6$-alkyl, $C_1$–$C_6$-halogenoalkyl, $C_1$–$C_6$-alkoxy and nitro, B represents hydrogen, $C_1$–$C_{12}$-alkyl or $C_1$–$C_8$-alkoxyalkyl, or A, B and the carbon atom to which they are bonded represent a saturated or unsaturated unsubstituted or substituted 5 or 6 member cycle which is optionally monosubstituted or polysubstituted by substituents selected from the group consisting of $C_1$–$C_{10}$-alkyl, $C_3$–$C_{10}$-cycloalkyl, $C_1$–$C_6$-halogenoalkyl, $C_1$–$C_{10}$-alkoxy, $C_1$–$C_{10}$-alkylthio, halogen or phenyl, or A, B and the carbon atom to which they are bonded represent a saturated or unsaturated, unsubstituted or substituted 5 or 6 member cycle which is substituted by substituents selected from the group consisting of alkylenediyl alkylenedioxy and alkylenedithio wherein said alkylenediyl, alkylenedioxy or alkylenedithio together with the carbon atom to which it is bonded forms a further five- to eight-membered cycle, or A, B and the carbon atom to which they are bonded represent a saturated or unsaturated, substituted or unsubstituted 5 or 6 member cycle which is optionally substituted by substituents selected from the group consisting of $C_1$–$C_6$-alkyl, $C_1$–$C_6$-alkoxy and halogen X represents halogen or $C_1$–$C_6$-alkyl, and Y represents halogen or $C_1$–$C_6$-alkyl.

3. A compound according to claim 2, in which

A represents hydrogen, or $C_1$–$C_{10}$-alkyl, $C_3$–$C_6$-alkenyl, $C_1$–$C_8$-alkoxy-$C_1$–$C_6$-alkyl, $C_1$–$C_6$-polyalkoxy-$C_1$–$C_6$-alkyl or $C_1$–$C_8$-alkylthio-$C_1$–$C_6$-alkyl, each of which is optionally substituted by substituents selected from the group consisting of fluorine or chlorine, or cycloalkyl having 3 to 7 ring atoms which is optionally substituted by substituents selected from the group consisting of fluorine, chlorine, $C_1$–$C_3$-alkyl and $C_1$–$C_3$-alkoxy, or represents phenyl, furanyl, pyridyl, imidazolyl, triazolyl, pyrazolyl, indolyl, thiazolyl, thienyl or phenyl-$C_1$–$C_4$-alkyl, each of which is optionally substituted by substituents selected from the group consisting of fluorine, chlorine, bromine, $C_1$–$C_4$-alkyl, $C_1$–$C_4$-halogenoalkyl, $C_1$–$C_4$-alkoxy and nitro, B represents hydrogen, $C_1$–$C_{10}$-alkyl or $C_1$–$C_6$-alkoxyalkyl, or A, B and the carbon atom to which they are bonded represent saturated or unsaturated $C_3$–$C_9$-spirocycle and a saturated or unsaturated, substituted or unsubstituted 5 or 6 member cycle which is optionally monosubstituted or polysubstituted by substituents selected from the group consisting of $C_1$–$C_6$-alkyl, $C_3$–$C_8$-cycloalkyl, $C_1$–$C_3$-haloalkyl, $C_1$–$C_6$-alkoxy, $C_1$–$C_6$-alkylthio, fluorine, chlorine and phenyl, or A, B and the carbon atom to which they are bonded represent a saturated or unsaturated, substituted or unsubstituted 5 or 6 member cycle which is substituted by substituents selected from the group consisting of alkylenediyl alkylenedioxy and alkylenedithio wherein said alkylenediyl, alkylenedioxy or alkylenedithio together with the carbon atom to which it is bonded forms a further five- to seven-membered cycle, or A, B and the carbon atom to which they are bonded represent a saturated or unsaturated, substituted or unsubstituted 5 or 6member cycle which is optionally substituted by substituents selected from the group consisting of $C_1$–$C_3$-alkyl, $C_1$–$C_3$-alkoxy, fluorine, chlorine and bromine X represents fluorine, chlorine, bromine or $C_1$–$C_4$-alkyl, and Y represents fluorine, chlorine, bromine or $C_1$–$C_4$-alkyl.

4. An acyl-amino acid ester according to claim 1, wherein

A represents hydrogen; alkyl alkenyl, alkoxyalkyl or alkylthioalkyl, each of which is optionally substituted by substituents selected from the group consisting of halogen; cycloalkyl;

optionally substituted aryl; and optionally substituted arylalkyl, wherein the optionally substituents are halogen, alkyl, halogenoalkyl, alkoxy or nitro, B represents hydrogen, alkyl or alkoxyalkyl, or A and B together with the carbon atoms to which they are bonded a saturated, unsubstituted or substituted 5 or 6 member cycle X represents halogen or alkyl, Y represents halogen or alkyl, and $R^8$ represents alkyl.

5. An acyl-amino acid ester according to claim 4, wherein

B represents alkoxyalkyl or

A and B together with the carbon atoms to which they are bonded a saturated, unsubstituted or substituted 5 or 6 member cycle.

6. A compound of the formula

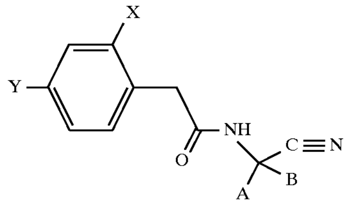

(XVII)

in which

A represents hydrogen, or alkyl, alkenyl, alkoxyalkyl or alkylthioalkyl, each of which is optionally substituted by halogen, cycloalkyl optionally substituted aryl, and optionally substituted arylalkyl wherein the optional substituents are halogen, alkyl, halogenoalkyl, alkoxy or nitro, B represents hydrogen, alkyl or alkoxyalkyl, or A and B together with the carbon atom to which they are bonded represent a saturated or unsaturated, unsubstituted or substituted 5 or 6 member cycle, X represents halogen or alkyl, Y represents halogen or alkyl, and provided that one of X and Y represents halogen and the other represents alkyl.

7. A compound according to claim 6, wherein

A represents hydrogen; alkyl, alkenyl, alkoxyalkyl or alkylthioalkyl, each of which is optionally substituted by substituents selected from the group consisting of halogen; cycloalkyl;

optionally substituted aryl; and optionally substituted arylalkyl, wherein the optionally substituents are halogen, alkyl, halogenoalkyl, alkoxy or nitro, B represents hydrogen, alkyl or alkoxyalkyl, or A and B together with the carbon atoms to which they are bonded a saturated, unsubstituted or substituted 5 or 6 member cycle X represents halogen or alkyl, Y represents halogen or alkyl, and $R^8$ represents alkyl.

* * * * *

UNITED STATES PATENT AND TRADEMARK OFFICE
CERTIFICATE OF CORRECTION

PATENT NO : 5, 847, 211

DATED : December 8, 1998

INVENTOR(S) : Reiner Fischer, et al.

It is certified that error appears in the above-identified patent and that said Letters Patent is hereby corrected as shown below:

Title Page, [57], Abstract

Delete "

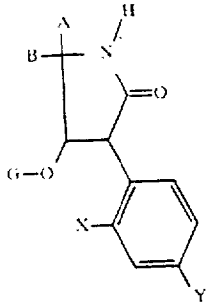

"

and substitute --

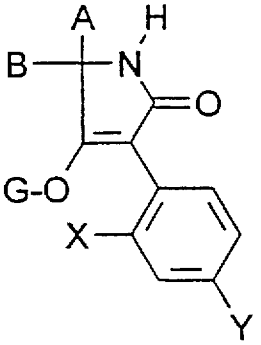

--

Signed and Sealed this

Eighth Day of June, 1999

Attest:

Q. TODD DICKINSON

Attesting Officer

*Acting Commissioner of Patents and Trademarks*